United States Patent
Pardridge et al.

(10) Patent No.: US 11,028,156 B2
(45) Date of Patent: *Jun. 8, 2021

(54) METHODS AND COMPOSITIONS FOR INCREASING IDURONATE 2-SULFATASE ACTIVITY IN THE CNS

(71) Applicant: ARMAGEN, INC., Calabasas, CA (US)

(72) Inventors: William M. Pardridge, Pacific Palisades, CA (US); Ruben J. Boado, Agoura Hills, CA (US)

(73) Assignee: ARMAGEN, INC., Calabasas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/982,990

(22) Filed: May 17, 2018

(65) Prior Publication Data
US 2018/0251535 A1 Sep. 6, 2018
US 2019/0185551 A2 Jun. 20, 2019

Related U.S. Application Data

(63) Continuation of application No. 14/305,402, filed on Jun. 16, 2014, now Pat. No. 10,011,651, which is a continuation of application No. 12/901,481, filed on Oct. 8, 2010, now Pat. No. 8,834,874.

(60) Provisional application No. 61/256,049, filed on Oct. 29, 2009, provisional application No. 61/250,378, filed on Oct. 9, 2009.

(51) Int. Cl.
| | |
|---|---|
| *A61K 38/00* | (2006.01) |
| *C07K 16/18* | (2006.01) |
| *C07K 16/28* | (2006.01) |
| *C12N 9/16* | (2006.01) |
| *A61K 39/00* | (2006.01) |

(52) U.S. Cl.
CPC .......... *C07K 16/18* (2013.01); *C07K 16/2869* (2013.01); *C12N 9/16* (2013.01); *A61K 38/00* (2013.01); *A61K 2039/505* (2013.01); *C07K 2317/565* (2013.01); *C07K 2317/92* (2013.01); *C07K 2319/30* (2013.01); *C07K 2319/33* (2013.01); *C12Y 301/06013* (2013.01)

(58) Field of Classification Search
None
See application file for complete search history.

(56) References Cited

U.S. PATENT DOCUMENTS

| | | | |
|---|---|---|---|
| 4,801,575 A | 1/1989 | Pardridge | |
| 4,902,505 A | 2/1990 | Pardridge et al. | |
| 4,946,778 A | 8/1990 | Ladner et al. | |
| 5,154,924 A | 10/1992 | Friden | |
| 5,180,820 A | 1/1993 | Barde et al. | |
| 5,182,107 A | 1/1993 | Friden | |
| 5,229,500 A | 7/1993 | Barde et al. | |
| 5,438,121 A | 8/1995 | Barde et al. | |
| 5,453,361 A | 9/1995 | Yancopoulos et al. | |
| 5,527,288 A | 6/1996 | Gross et al. | |
| 5,527,527 A | 6/1996 | Friden | |
| 5,562,903 A | 10/1996 | Co et al. | |
| 5,610,279 A | 3/1997 | Brockhaus et al. | |
| 5,618,920 A | 4/1997 | Robinson et al. | |
| 5,656,284 A | 8/1997 | Balkin | |
| 5,672,683 A | 9/1997 | Friden et al. | |
| 5,693,762 A | 12/1997 | Queen et al. | |
| 5,824,782 A | 10/1998 | Hoelzer et al. | |
| 5,837,231 A | 11/1998 | Low et al. | |
| 5,848,991 A | 12/1998 | Gross et al. | |
| 5,977,307 A | 11/1999 | Friden et al. | |
| 5,997,501 A | 12/1999 | Gross et al. | |
| 6,015,662 A | 1/2000 | Hackett, Jr. et al. | |
| 6,041,775 A | 3/2000 | Century | |
| 6,060,069 A | 5/2000 | Hill et al. | |
| 6,153,190 A | 11/2000 | Young et al. | |
| 6,165,476 A | 12/2000 | Strom et al. | |
| 6,165,783 A | 12/2000 | Weiss et al. | |
| 6,201,105 B1 | 3/2001 | Smith et al. | |
| 6,248,262 B1 | 6/2001 | Kubotera et al. | |
| 6,284,262 B1 | 9/2001 | Place | |
| 6,287,792 B1 | 9/2001 | Pardridge et al. | |
| 6,322,808 B1 | 11/2001 | Trautman et al. | |
| 6,329,508 B1 | 12/2001 | Friden | |
| 6,348,210 B1 | 2/2002 | Gale | |
| 6,361,760 B1 | 3/2002 | Murata et al. | |
| 6,372,250 B1 | 4/2002 | Pardridge | |
| 6,375,975 B1 | 4/2002 | Modi | |
| 6,531,309 B1 | 3/2003 | Hu et al. | |
| 6,541,610 B1 | 4/2003 | Smith | |
| 6,582,945 B1 | 6/2003 | Raso | |
| 6,583,272 B1 | 6/2003 | Bailon | |
| 6,709,833 B2 | 3/2004 | Fukui et al. | |
| 6,743,427 B1 | 6/2004 | Schenk | |
| 6,858,206 B2 | 2/2005 | Kakkis | |

(Continued)

FOREIGN PATENT DOCUMENTS

| | | |
|---|---|---|
| EP | 0613007 A2 | 8/1994 |
| EP | 0613007 A3 | 10/1995 |

(Continued)

OTHER PUBLICATIONS

Arai, R. et al. Design of the linkers which effectively separate domains of a bifunctional fusion protein. Protein Eng. Aug. 2001;14(8):529-32.

(Continued)

*Primary Examiner* — Yunsoo Kim
(74) *Attorney, Agent, or Firm* — Wilson Sonsini Goodrich & Rosati

(57) ABSTRACT

Provided herein are methods and compositions for treating a subject suffering from a deficiency in iduronate 2-sulfatase in the CNS. The methods include systemic administration of a bifunctional fusion antibody comprising an antibody that crosses the blood brain barrier (BBB) and an iduronate 2-sulfatase.

14 Claims, 20 Drawing Sheets
Specification includes a Sequence Listing.

(56) References Cited

U.S. PATENT DOCUMENTS

| | | |
|---|---|---|
| 7,053,202 B2 | 5/2006 | O'Keefe et al. |
| 7,078,376 B1 | 7/2006 | Thompson |
| 7,214,658 B2 | 5/2007 | Tobinick et al. |
| 7,226,758 B2 | 6/2007 | Lin et al. |
| 7,294,704 B2 | 11/2007 | Simon et al. |
| 7,309,687 B1 | 12/2007 | Brines et al. |
| 7,341,720 B2 | 3/2008 | Stefano |
| 7,388,079 B2 | 6/2008 | Pardridge et al. |
| 7,700,097 B2 | 4/2010 | Braslawsky et al. |
| 7,741,446 B2 | 6/2010 | Pardridge et al. |
| 7,744,879 B2 | 6/2010 | Shusta et al. |
| 7,807,409 B2 | 10/2010 | Kopetzki |
| 7,981,417 B2 | 7/2011 | Shusta et al. |
| 8,053,569 B2 | 11/2011 | Pardridge et al. |
| 8,084,026 B2 | 12/2011 | Glaser et al. |
| 8,124,073 B2 | 2/2012 | Stefano |
| 8,124,095 B2 | 2/2012 | Pardridge et al. |
| 8,142,781 B2 | 3/2012 | Pardridge et al. |
| 8,486,399 B2 | 7/2013 | Pardridge et al. |
| 8,497,246 B2 | 7/2013 | Pardridge et al. |
| 8,603,473 B2 | 12/2013 | Glaser et al. |
| 8,715,661 B2 | 5/2014 | Pardridge et al. |
| 8,741,260 B2 | 6/2014 | Pardridge et al. |
| 8,753,610 B2 | 6/2014 | Pardridge et al. |
| 8,759,297 B2 | 6/2014 | Pardridge et al. |
| 8,834,874 B2 | 9/2014 | Pardridge et al. |
| 8,853,353 B2 | 10/2014 | Beliveau et al. |
| 8,906,379 B2 | 12/2014 | Stefano |
| 8,920,801 B2 | 12/2014 | Pardridge et al. |
| 8,974,791 B2 | 3/2015 | Pardridge et al. |
| 9,533,055 B2 | 1/2017 | Pardridge et al. |
| 10,011,651 B2 | 7/2018 | Pardridge et al. |
| 2002/0052311 A1 | 5/2002 | Solomon et al. |
| 2002/0137684 A1 | 9/2002 | Tchistiakova et al. |
| 2002/0169109 A1 | 11/2002 | Plata-Salaman et al. |
| 2003/0129186 A1 | 7/2003 | Beliveau et al. |
| 2003/0165853 A1 | 9/2003 | Partridge et al. |
| 2004/0043446 A1 | 3/2004 | Defrees et al. |
| 2004/0072291 A1 | 4/2004 | Carr et al. |
| 2004/0101904 A1 | 5/2004 | Pardridge et al. |
| 2004/0102369 A1 | 5/2004 | Wu et al. |
| 2004/0229250 A1 | 11/2004 | Figura et al. |
| 2004/0248197 A1 | 12/2004 | Holtzman et al. |
| 2005/0006823 A1 | 1/2005 | Merrick |
| 2005/0026823 A1 | 2/2005 | Zankel et al. |
| 2005/0142141 A1 | 6/2005 | Pardridge |
| 2005/0163782 A1 | 7/2005 | Glaser et al. |
| 2005/0163783 A1 | 7/2005 | Braslawsky et al. |
| 2006/0228348 A1 | 10/2006 | Stefano |
| 2007/0031402 A1 | 2/2007 | Zhang et al. |
| 2007/0081992 A1 | 4/2007 | Pardridge et al. |
| 2007/0082380 A1 | 4/2007 | Pardridge et al. |
| 2007/0275882 A1 | 11/2007 | Meijer et al. |
| 2007/0280940 A1 | 12/2007 | Winkles et al. |
| 2008/0003211 A1 | 1/2008 | Fogh et al. |
| 2008/0019984 A1 | 1/2008 | Shusta et al. |
| 2008/0051564 A1 | 2/2008 | Pardridge et al. |
| 2008/0152645 A1 | 6/2008 | Pardridge et al. |
| 2008/0170994 A1 | 7/2008 | Pardridge et al. |
| 2008/0171055 A1 | 7/2008 | Pardridge et al. |
| 2008/0226658 A1 | 9/2008 | Stefano |
| 2008/0292639 A1 | 11/2008 | Shen et al. |
| 2008/0292704 A1 | 11/2008 | Arnason et al. |
| 2009/0041758 A1 | 2/2009 | Glaser et al. |
| 2009/0047338 A1 | 2/2009 | Swamy et al. |
| 2009/0053219 A1 | 2/2009 | Pardridge et al. |
| 2009/0068206 A1 | 3/2009 | Pardridge et al. |
| 2009/0156498 A1 | 6/2009 | Pardridge et al. |
| 2009/0162380 A1 | 6/2009 | Glaser et al. |
| 2009/0238789 A1 | 9/2009 | Guyon et al. |
| 2009/0270267 A1 | 10/2009 | Akiyama et al. |
| 2009/0304696 A1 | 12/2009 | Lawson et al. |
| 2010/0077498 A1 | 3/2010 | Pardridge et al. |
| 2010/0098693 A1 | 4/2010 | Pardridge et al. |
| 2010/0172919 A1 | 7/2010 | Grimm et al. |
| 2010/0175141 A1 | 7/2010 | Collins et al. |
| 2010/0183577 A1 | 7/2010 | Stern et al. |
| 2010/0209425 A1 | 8/2010 | Shusta et al. |
| 2010/0261647 A1 | 10/2010 | Pardridge et al. |
| 2010/0290985 A1 | 11/2010 | Pardridge et al. |
| 2011/0021590 A1 | 1/2011 | Duggan |
| 2011/0110935 A1 | 5/2011 | Pardridge et al. |
| 2011/0262460 A1 | 10/2011 | Shusta et al. |
| 2011/0318327 A1 | 12/2011 | Concino et al. |
| 2012/0014936 A1 | 1/2012 | Natoli et al. |
| 2012/0094934 A1 | 4/2012 | Collard et al. |
| 2012/0141507 A1 | 6/2012 | Stefano |
| 2012/0232021 A1 | 9/2012 | Martini et al. |
| 2013/0039888 A1 | 2/2013 | McCarty et al. |
| 2013/0095092 A1 | 4/2013 | Quinn et al. |
| 2013/0130292 A1 | 5/2013 | Szalay et al. |
| 2013/0142794 A1 | 6/2013 | Pardridge et al. |
| 2013/0287773 A1 | 10/2013 | Pardridge et al. |
| 2013/0295077 A1 | 11/2013 | Concino et al. |
| 2013/0323221 A1 | 12/2013 | Radin |
| 2014/0037621 A1 | 2/2014 | Tsurushita et al. |
| 2014/0187502 A1 | 7/2014 | Martini et al. |
| 2014/0193409 A1 | 7/2014 | Pardridge et al. |
| 2014/0288273 A1 | 9/2014 | Pardridge et al. |
| 2014/0294822 A1 | 10/2014 | Pardridge et al. |
| 2015/0023956 A1 | 1/2015 | Pardridge et al. |
| 2015/0064184 A1 | 3/2015 | Pardridge |
| 2015/0203586 A1 | 7/2015 | Pardridge et al. |
| 2015/0258180 A1 | 9/2015 | Mahuran et al. |
| 2015/0320844 A1 | 11/2015 | Stefano et al. |
| 2016/0137994 A1 | 5/2016 | Ito et al. |
| 2016/0152719 A1 | 6/2016 | Pardridge |
| 2016/0208006 A1 | 7/2016 | Pardridge et al. |
| 2016/0208009 A1 | 7/2016 | Umana et al. |
| 2017/0066832 A1 | 3/2017 | Pardridge |
| 2017/0114152 A1 | 4/2017 | Pardridge |

FOREIGN PATENT DOCUMENTS

| | | |
|---|---|---|
| EP | 2051734 A2 | 4/2009 |
| EP | 2182980 A2 | 5/2010 |
| EP | 2408474 A2 | 1/2012 |
| EP | 2485761 A1 | 8/2012 |
| EP | 2785378 A1 | 10/2014 |
| JP | H06228199 A | 8/1994 |
| JP | 2006511516 A | 4/2006 |
| JP | 2014116085 A | 6/2014 |
| JP | 2016529759 A | 9/2016 |
| WO | WO-9802421 A1 | 1/1998 |
| WO | WO-9900150 A2 | 1/1999 |
| WO | WO-9900951 A1 | 1/1999 |
| WO | WO-9900150 A3 | 4/1999 |
| WO | WO-9966951 A2 | 12/1999 |
| WO | WO-0015759 A1 | 3/2000 |
| WO | WO-0037502 A2 | 6/2000 |
| WO | WO-0051621 A1 | 9/2000 |
| WO | WO-0145730 A2 | 6/2001 |
| WO | WO-03074081 A1 | 9/2003 |
| WO | WO-2004003019 A2 | 1/2004 |
| WO | WO-2004050016 A2 | 6/2004 |
| WO | WO-2004072275 A2 | 8/2004 |
| WO | WO-2004108071 A2 | 12/2004 |
| WO | WO-2006081171 A1 | 8/2006 |
| WO | WO-2007022416 A2 | 2/2007 |
| WO | WO-2007044323 A2 | 4/2007 |
| WO | WO-2007022416 A3 | 5/2007 |
| WO | WO-2008022349 A2 | 2/2008 |
| WO | WO-2009018122 A2 | 2/2009 |
| WO | WO-2007044323 A3 | 5/2009 |
| WO | WO-2009070597 A2 | 6/2009 |
| WO | WO-2010003101 A2 | 1/2010 |
| WO | WO-2010108048 A2 | 9/2010 |
| WO | WO-2011044542 A1 | 4/2011 |
| WO | WO-2012075037 A1 | 6/2012 |
| WO | WO-2012085622 A1 | 6/2012 |
| WO | WO-2012177997 A1 | 12/2012 |

(56) References Cited

FOREIGN PATENT DOCUMENTS

| WO | WO-2013081706 A1 | 6/2013 |
|----|------------------|--------|
| WO | WO-2015009961 A1 | 1/2015 |
| WO | WO-2015012944 A1 | 1/2015 |

OTHER PUBLICATIONS

Argos, An investigation of oligopeptides linking domains in protein tertiary structures and possible candidates for general gene fusion., 1990, J Mol. Biol. 211:943-58, doi:10.1016/0022-2836(90)90085-Z.
Barbon, Christine M. et al. AAV*-Mediated Hepatic Expression of Acid Sphingomyelinase Corrects the Metabolic Defect in the Visceral Organs of a Mouse Model of Niemann-Pick Disease. Molecular Therapy, 12(3):431-440 (Sep. 2005).
Bird et al. Single-chain antigen-binding proteins. Science 242:423-442 (1988).
Bradbury, AM et al. Neurodegenerative lysosomal storage disease in European Burmese cats with hexosaminidase beta-subunit deficiency. Mol Genet Metab. May 2009;97(1):53-9. [Epub Feb. 23, 2009].
Bu, Jie et al. Merits of Combination Cortical, Subcortical, and Cerebellar Injections for the Treatment of Niemann-Pick Disease Type A. Mol Ther. Oct. 2012; 20(10): 1893-1901.
Camp, L.A. et al. Molecular cloning and expression of palmitoyl-protein thioesterase. J. Biol. Chem. 269(37):2312-23219 (Sep. 16, 1994).
Crasto, C.J. Linker: A program to generate linker sequences for fusion proteins. Protein Engineering, 13(5): 309-312 (2000).
Dearborn, J.T. et al. Histochemical localization of palmitoyl protein thioesterase-1 activity. Mol. Genet. Metab. 117(2):210-216 (Feb. 2016) [ E-Pub Nov. 11, 2015].
Dewji, N.N. Purification and characterization of beta-N-acetylhexosaminidase I2 from human liver. Biochem J. Feb. 15, 1986; 234(1): 157-162.
Fraldi, et al. Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.
George, et al. An analysis of protein domain linkers: their classification and role in protein folding. Protein Eng. Nov. 2002;15(11):871-9.
Hobert, J. And Dawson, G. Neuronal ceroid lipofuscinoses therapeutic strategies: Past, Present and Future. Biochimia et Biophysica Acta (BBA)—Molecular Basis of Disease, 1762(10):945-953 (Oct. 2006).
Hu, J. et al. Intravenous high-dose enzyme replacement therapy with recombinant palmitoyl-protein thioesterase reduces visceral lysosomal storage and modestly prolongs survival in a preclinical mouse model of infantile neuronal ceroid lipofuscinosis. Mol Genet Metab. Sep. 2012;107(1-2):213-21. E-Pub May 22, 2012.
Jeyakumar, M. et al. Neural stem cell transplantation benefits a monogenic neurometabolic disorder during the symptomatic phase of disease. Stem Cells. Sep. 2009; 27(9): 2362-2370.
Lu, J.Y. et al. Human recombinant palmitoyl-protein thioesterase-1 (PPT1) for preclinical evaluation of enzyme replacement therapy for infantile neuronal ceroid lipofuscinosis. Mol. Genet. Metab. 99(4):374-378 (Apr. 2010) [E-Pub Dec. 5, 2009].
Meng, XL et al. Induced pluripotent stem cells derived from mouse models of lysosomal storage disorders. Proc. Natl. Acad. Sci USA, 107(17):7886-7891 (Apr. 27, 2010).
Miranda, SR et al. Infusion of recombinant human acid sphingomyelinase into niemann-pick disease mice leads to visceral, but not neurological, correction of the pathophysiology. FASEB J. Oct. 2000;14(13):1988-1995.
Myerowitz, R. et al. Human beta-hexosaminidase alpha chain: coding sequence and homology with the beta chain. Proc Natl Acad Sci U S A. Dec. 1985; 82(23): 7830-7834.
Novo, J.B. et al. Generation of a Chinese Hamster Ovary Cell line Producing Recombinant Human Glucocerebrosidase. J Biomed Biotechnol. 2012; 2012: 875383.
Pardridge, W.M. and Boado, R.J. Reengineering biopharmaceuticals for targeted delivery across the blood-brain barrier. Methods Enzymol. 503:269-292 (2012).
Sands, et al. Enzyme replacement therapy for murine mucopolysaccharidosis type VII. J Clin Invest. Jun. 1994; 93(6): 2324-2331.
Schuchman, E.H. et al. Human acid sphingomyelinase. Isolation, nucleotide sequence and expression of the full-length and alternatively spliced cDNAs. J Biol Chem. May 5, 1991;266(13):8531-9.
Sleat, D.E. et al. Aminoglycoside-mediated suppression of nonsense mutations in late infantile neuronal ceroid lipofuscinosis. Eur. J. Paediatr. Neurol. 5 Suppl. A: 57-62 (2001).
U.S. Appl. No. 14/192,792 Notice of Allowance dated Aug. 6, 2018.
U.S. Appl. No. 14/281,803 Final Office Action dated Aug. 15, 2018.
U.S. Appl. No. 15/357,894 Non-Final Office Action dated Jul. 3, 2018.
U.S. Appl. No. 15/397,649 Notice of Allowance dated Sep. 20, 2018.
Van Diggelen, O.P., et al. A new fluorimetric enzyme assay for the diagnosis of Niemann-Pick A/B, with specificity of natural sphingomyelinase substrate. J. Inherit Metab. Dis. 2005 ;28(5):733-741.
Van Diggelen, O.P., et al A rapid fluorogenic palmitoyl-protein thioesterase assay: pre- and postnatal diagnosis of INCL. Mol. Genet. Metab. 66(4):240-244 (Apr. 1999).
Von Specht, B.U. et al. Enzyme replacement in Tay-Sachs disease. Neurology. Jun. 1979;29(6):848-54.
Advisory action dated Jun. 13, 2014 for U.S. Appl. No. 13/141,682.
Aharoni, et al. Directed evolution of mammalian paraoxonases PON1 and PON3 for bacterial expression and catalytic specialization. Proc Natl Acad Sci U S A. Jan. 13, 2004;101(2):482-7. Epub Dec. 26, 2003.
Ai, et al., 2003. Intraputamenal Infusion of GDNF in Aged Rhesus Monkeys: Distribution and Dopaminergic Effects. The Journal of Comparative Neurology 461: 250-261.
Airavaara, et al. Effects of repeated morphine on locomotion, place preference and dopamine in heterozygous glial cell line-derived neurotrophic factor knockout mice. Genes Brain Behav. Apr. 2007;6(3):287-98.
Akiyama, et al. Enzyme augmentation therapy enhances the therapeutic efficacy of bone marrow transplantation in mucopolysaccharidosis type II mice. Mol Genet Metab. Feb. 2014;111(2):139-46. doi: 10.1016/j.ymgme.2013.09.013. Epub Sep. 21, 2013.
Al Sawaf, et al. Neurological findings in Hunter disease: pathology and possible therapeutic effects reviewed. J Inherit Metab Dis. Aug. 2008:31(4):473-80.
Albayrak, et al. Effect of transient focal ischemia on blood-brain barrier permeability in the rat: Correlation to Cell Injury. Acta Neuropathol 1997;94:158-63.
Albeck, et al. A non-invasive transport system for GDNF across the blood-brain barrier. NeuroReport. Jul. 7, 1997; 8(9-10):2293-2298.
Alberts, et al. Molecular Biology of the Cell. 3rd Edition. Garland Publishing Inc. New York. 1994; pp. 1206-1207.
Altschul, et al. Optimal sequence alignment using affine gap costs. Bulletin of Mathematical Biology. 1986; 48(5-6):603-16.
Altschul, et al. Basic local alignment search tool. Journal of Molecular Biology 215.3 (1990): 403-410.
Altschul et al. Gapped BLAST and PSI-BLAST: a new generation of protein database search programs. Nucleic Acids Res 25:3389-3402 (1977).
Amgen www.amgen.com Accessed Dec. 16, 2005.
Arndt, et al. Generation of a highly stable, internalizing anti-CD22 single-chain Fv fragment for targeting non-Hodgkin's lymphoma. Int J Cancer. Dec. 10, 2003;107(5):822-829.
Aronovich et al., "Molecular Genetic Defect Underlying α-L-Iduronidase pseudodeficiency," Am. Journ. Hum. Genet. 58: 75-85 (1996).
Auclair, et al. Repeated intrathecal injections of recombinant human 4-sulphatase remove dural storage in mature mucopolysaccharidosis VI cats primed with a short-course tolerisation regimen.

(56) References Cited

OTHER PUBLICATIONS

Mol Genet Metab. Feb. 2010;99(2):132-41. doi: 10.1016/j.ymgme. 2009.10.002. Epub Oct. 13, 2009.
"Australian Application No. 2013206657 Examination Report dated Apr. 25, 2016".
Australian Patent Application No. 2012346448 dated Sep. 8, 2016.
Ausubel, et al. Current Protocols in Molecular Biology. John Wiley & Sons, New York, 1995 supplement.
Bachis, et al. 2003. Brain-Derived Neurotropic Factor Inhibits Human Immunodeficiency Virus-1/gp 120-Mediated Cerebellar Granule Cell Death by Preventing gp 120 Internalization. The Journal of Neuroscience 23 (13): 5712-22.
Baloh, et al. Functional mapping of receptor specificity domains of glial cell line-derived neurotrophic factor (GDNF) family ligands and production of GFRalpha1 RET-specific agonists. J Biol Chem. Feb. 4, 2000;275(5):3412-20.
Barth et al. Boron neutron capture therapy of brain tumors: an emerging therapeutic modality. Neurosurgery. Mar. 1999;44(3):433-50; discussion 450-1.
Batzer et al. Enhanced evolutionary PCR using oligonucleotides with inosine at the 3'-terminus. Nucleic Acid Res 19:5081 (1991).
Beck, et al. 1994. Brain-Derived Neurotropic Factor Protects Against Ischemic Cell Damage in Rat Hippocampus. Journal of Cerebral Blood Flow and Metabolism 14: 689-92.
Begley et al., "Lysosomal storage diseases and the blood-brain barrier," Current Pharmaceutical Design, vol. 14, No. 16, pp. 1566-1580 (2008).
Benito, et al. Beta-galactosidase enzymatic activity as a molecular probe to detect specific antibodies. J Biol Chem. Aug. 30, 1996;271(35):21251-6.
Bickel; et al., "In vivo demonstration of subcellular localization of anti-transferrin receptor monoclonal antibody-colloidal gold conjugate in brain capillary endothelium", J Histochem Cytochem, Nov. 1994, 42(11), 1493-7.
Bifare, et al. 2005. Brain-Derived Neurotropic Factor Protects against Multiple Forms of Brain Injury in Bacterial Meningitis. The Journal of Infectious Diseases 191: 40-45.
Biffi, A. et al. Correction of metachromatic leukodystrophy in the mouse model by transplantation of genetically modified hematopoietic stem cells. J. Clin. Invest., 113(8); p. 1118-1129 (2004).
Biogen Idec www.idecpharma.com/site/home.html Accessed Dec. 16, 2005.
Boado, et al. Agt-181: expression in CHO cells and pharmacokinetics, safety, and plasma iduronidase enzyme activity in Rhesus monkeys. Oct. 2009; 144(2):135-41.
Boado, et al. Blood-brain barrier molecular trojan horse enables imaging of brain uptake of radioiodinated recombinant protein in the rhesus monkey. Bioconjug Chem. Oct. 16, 2013;24(10):1741-9. doi: 10.1021/bc400319d. Epub Oct. 3, 2013.
Boado, et al. CHO cell expression, long-term stability, and primate pharmacokinetics and brain uptake of an IgG-paroxonase-1 fusion protein. Biotechnol Bioeng. Jan. 2011;108(1):186-96.
Boado, et al. Drug delivery of antisense molecules to the brain for treatment of Alzheimer's disease and cerebral AIDS. J Pharm Sci. Nov. 1998;87(11):1308-15.
Boado et al., "Drug targeting of erythropoietin across the primate blood-brain barrier with an IgG molecular Trojan horse," Journal of Pharmacology and Experimental Therapeutics, vol. 333, No. 3, Jun. 1, 2010; 961-969.
Boado, et al. Engineering and expression of a chimeric transferrin receptor monoclonal antibody for blood-brain barrier delivery in the mouse. Biotechnol Bioeng. Mar. 1, 2009;102(4):1251-8.
Boado, et al. Fusion Antibody for Alzheimer's Disease with Bi-Directional Transport Across the Blood-Brain Barrier and Abeta Fibril Disaggregation. Bioconjug Chem. 2007;18(2):447-55.
Boado, et al. GDNF fusion protein for targeted-drug delivery across the human blood-brain barrier. Biotechnol Bioeng. Jun. 1, 2008;100(2):387-96.
Boado, et al. Genetic engineering, expression, and activity of a fusion protein of a human neurotrophin and a molecular Trojan horse for delivery across the human blood-brain barrier. Biotechnology and Bioengineering. 2007;97:1376-1386.
Boado et al., "Genetic engineering of a lysosomal enzyme fusion protein for targeted delivery across the human blood-brain barrier," Biotechnology and Bioengineering, vol. 99, No. 2, pp. 475-484 (2008).
Boado et al., "Genetic Engineering of IgG-glucuronidase fusion proteins," J. Drug Targeting 18(3):205-11 (2010).
Boado, et al. Glycemic control and chronic dosing of rhesus monkeys with a fusion protein of iduronidase and a monoclonal antibody against the human insulin receptor. Drug Metab Dispos. Oct. 2012;40(10):2021-5. doi: 10.1124/dmd.112.046375. Epub Jul. 20, 2012.
Boado, et al. Humanization of anti-human insulin receptor antibody for drug targeting across the human blood-brain barrier. Biotechnology and Bioengineering. 2007;96:381-391.
Boado et al., "IgG-single chain Fv fusion protein therapeutic for Alzheimer's disease: Expression in CHO cells and pharmacokinetics and brain delivery in the rhesus monkey," Biotechnology and Bioengineering, vol. 105, No. 3, pp. 627-635 (2010).
Boado et al., "Pharmacokinetics and brain uptake of a genetically engineered bifunctional fusion antibody targeting the mouse transferrin receptor," Molecular Pharmaceutics, vol. 7, No. 1, pp. 237-244 (2010).
Boado, et al. Reversal of lysosomal storage in brain of adult MPS-I mice with intravenous Trojan horse-iduronidase fusion protein. Mol Pharm. Aug. 1, 2011;8(4):1342-50. Epub Jun. 17, 2011.
Boado, et al. Selective targeting of a TNFR decoy receptor pharmaceutical to the primate brain as a receptor-specific IgG fusion protein. J Biotechnol. Mar. 2010;146(1-2):84-91.
Boado, Ruben J. et al. Glycemic Control and Chronic Dosing of Rhesus Monkeys with a Fusion Protein of Iduroniadase and a Monoclonal Antibody Against the Human Insulin Receptor Drug Metabolism and Disposition vol. 40, No pp. 2021-2025 (2012).
Board of Patent Appeals and Interferences (BPAI) Decision dated Jul. 22, 2010 from U.S. Appl. No. 11/061,956.
Bosslet, et al. Molecular and functional characterisation of a fusion protein suited for tumour specific prodrug activation. Br J Cancer. Feb. 1992;65(2):234-8.
Bosslet, et al. Tumor-selective prodrug activation by fusion protein-mediated catalysis. Cancer Res. Apr. 15, 1994;54(8):2151-9.
Braun, et al. Metabolic correction and cross-correction of mucopolysaccharidosis type II (Hunter syndrome) by retroviral-mediated gene transfer and expression of human iduronate-2-sulfatase. Proc Natl Acad Sci 1993;90:11830-11834.
Brines, et al. Erythropoietin crosses the blood-brain barrier to protect against experimental brain injury, Proc Natl Acad Sci USA. 2000; 97:10526-10531.
Brummell, et al. Probing the combining site of an anti-carbohydrate antibody by saturation-mutagenesis: role of the heavy-chain CDR3 residues. Biochemistry. 1993; 32(4):1180-7.
Buchli, et al. Inhibition of Nogo: a key strategy to increase regeneration, plasticity and functional recovery of the lesioned central nervous system. Ann Med. 2005;37(8):556-67.
Burgess, et al. Possible dissociation of the heparin-binding and mitogenic activities of heparin-binding (acidic fibroblast) growth factor-1 from its receptor-binding activities by site-directed mutagenesis of a single lysine residue. J Cell Biol. Nov. 1990;111(5 Pt 1):2129-38.
Canadian Application No. 2,694,762 Office Action dated Apr. 7, 2016.
Canadian Patent Application No. 2,748,889 Office Action dated Oct. 19, 2016.
Carnicella, et al. GDNF is a fast-acting potent inhibitor of alcohol consumption and relapse. Proc Natl Acad Sci U S A. Jun. 10, 2008;105(23):8114-9.
Casset, et al. A peptide mimetic of an anti-CD4 monoclonal antibody by rational design. Biochem Biophys Res Commun. Jul. 18, 2003;307(1):198-205.
Cassol et al. Stability of dried blood spot specimens for detection of human immunodeficiency virus DNA by polymerase chain reaction. J Clin Microbiol. 30(12):3039-3042 (1992).

(56) References Cited

OTHER PUBLICATIONS

Chen, et al. Cotranslational folding and calnexin binding during glycoprotein synthesis. Proc Natl Acad Sci U S A. Jul. 3, 1995;92(14):6229-33.
Chen, et al. In vitro scanning saturation mutagenesis of all the specificity determining residues in an antibody binding site. Protein Engineering. 1999; vol. 12, No. 4, 349-56.
Cheng, et al. 1997. Marked Age-dependent Neuroprotection by Brain-derived Neurotropic Factor Against Neonatal Hypoxic-Ischemic Brain Injury. Annals of Neurology 41 (4): 521-29.
Cheng, et al. 2004. Neuroprotection for Ischemic Stroke: Two Decades of Success and Failure. The Journal of the American Society for Experimental Neuro Therapeutics 1: 36-45.
"Cheng, SH et al. Gene therapy progress and prospects: gene therapy of lysosomal storage disorders, Gene Therapy 10:1275-1281 (2003)".
Chothia et al. Canonical structures for the hypervariable regions of immunoglobulins. J Mol Biol. 196(4):901-917 (1987).
Christian, et al. The distribution of D2/D3 receptor binding in the adolescent rhesus monkey using small animal PET imaging. Neuroimage. Feb. 15, 2009;44(4):1334-44. doi: 10.1016/j.neuroimage.2008.10.020. Epub Oct. 29, 2008.
Chudler, Eric H.Brain Facts and Figures, from Eric H. Chudler's Neuroscience for Kids: faculty.washington.edu/chudler/facts.html. Retreived from Internet on Jun. 6, 2016, 14 pages.
Chung et al. Antibodies against West Nile Virus nonstructural protein NS1 prevent lethal infection through Fc gamma receptor-dependent and -independent mechanisms. J Virol. Feb. 2006;80(3):1340-51.
Colman et al. Effects of amino acid sequence changes on antibody-antigen interactions. Research in Immunology 145(1):33-36 (1994).
Coloma, et al. 1997. Design and production of novel tetravalent bispecific antibodies. Nat Biotechnol Feb;15(2):159-63.
Coloma, et al. 1999. Transport Across the Primate Blood-Brain Barrier of a Genetically Engineered Chimeric Monoclonal Antibody to the Human Insulin Receptor. Pharmaceutical Research 17 (3): 266-274.
Coloma, et al. The hinge as a spacer contributes to covalent assembly and is required for function of IgG. J Immunol. Jan. 15, 1997;158(2):733-40.
Corchero, et al. The position of the heterologous domain can influence the solubility and proteolysis of beta-galactosidase fusion proteins in E. coli. J Biotechnol. Jul. 31, 1996;48(3):191-200.
Cosma, et al. The multiple sulfatase deficiency gene encodes an essential and limiting factor for the activity of sulfatases. Cell. May 16, 2003;113(4):445-56.
Cowen, et al. 2004. Neuropeptides: implications for alcoholism. Journal of Neurochemistry 89: 273-85.
Crow, et al. Biochemical and histopathological studies on patients with mucopolysaccharidoses, two of whom had been treated by fibroblast transplantation. J Clin Pathol. 1983:36(4):415-30.
Dawson, et al. A comparative assessment of the efficacy and side-effect liability of the neuroprotective compounds in experimental stroke. 2001. Brain Research 892: 344-50.
De Graaf, M. et al., "Expression of scFvs and scFv Fusion Proteins in Eukaryotic Cells." Mol. Biol. 2002; 178:379-387.
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Deakin, et al. Enzymatically active paraoxonase-1 is located at the external membrane of producing cells and released by a high affinity, saturable, desorption mechanism. J Biol Chem. Feb. 8, 2002;277(6):4301-8. Epub Nov. 28, 2001.
Deane, et al. IgG-assisted age-dependent clearance of Alzheimer's amyloid beta peptide by the blood-brain barrier neonatal Fc receptor. J Neurosci. 2005; 25(50):11495-503.
Deguchi, et al. Retention of biologic activity of human epidermal growth factor following conjugation to a blood-brain barrier drug delivery vector via an extended poly(ethylene glycol) linker. Bioconjug Chem. Jan.-Feb. 1999;10(1):32-7.
Dierks, et al. Conversion of cysteine to formylglycine in eukaryotic sulfatases occurs by a common mechanism in the endoplasmic reticulum. Febs Lett. Feb. 13, 1998;423(1):61-5.
Dierks, et al. Sequence determinants directing conversion of cysteine to formylglycine in eukaryotic sulfatases. EMBO J. Apr. 15, 1999;18(8):2084-91.
Dreier, et al. Recombinant immunocytokines targeting the mouse transferrin receptor: construction and biological activities. Bioconjug Chem. Jul.-Aug. 1998;9(4):482-9.
Duchnowska, et al. Central nervous system metastases in breast cancer patients administered trastuzumab. Cancer Treat Rev. Jun. 2005;31(4):312-8.
Duffy, et al. 1987. Blood-brain barrier transcytosis of insulin in developing rabbits. Brain Research 420: 32-38.
Duffy, et al. 1988. Human blood-brain barrier insulin-like growth factor receptor. Metabolism. Feb;37(2):136-40.
Durrington, et al. Paraoxonase and atherosclerosis. Arterioscler Thromb Vasc Biol. Apr. 2001;21(4):473-80.
Ehrenreich, et al. Erythropoietin therapy for acute stroke is both safe and beneficial. Mol Med. Aug. 2002;8(8):495-505.
Eketjall, et al. Distinct structural elements in GDNF mediate binding to GFRalpha1 and activation of the GFRalpha1-c-Ret receptor complex. EMBO J. Nov. 1, 1999;18(21):5901-10.
Elliott, et al. Control of rHuEPO biological activity: the role of carbohydrate. Exp Hematol. Dec. 2004;32(12):1146-55.
EP06825389.7 Search Report dated Feb. 23, 2010.
EP07841110.5 Search Report and opinion dated Dec. 2, 2010.
EP08796594.3 Search Report and opinion dated Mar. 16, 2012.
Eslamboli, et al. Continuous Low-Level Glial Cell Line-Derived Neurotrophic Factor Delivery Using Recombinant Adeno-Associated Viral Vectors Provides Neuroprotection and Induces Behavioral Recovery in a Primate Model of Parkinson's Disease. J. Neurosci. 2005:25:769-77.
European Application No. 11733492.0 Office Action dated Feb. 9, 2016.
European Application No. 16171496 Extended European Search Report dated Oct. 31, 2016.
European Application No. 16171496.9 Extended European Search Report dated Feb. 10, 2017.
European Office Action dated Oct. 16, 2014 for EP Application No. 06825389.7.
European search report and search opinion dated Sep. 21, 2015 for EP Application No. 12854380.8.
European search report and search opinion dated Dec. 20, 2012 for EP Application No. 10754139.
European search report dated Mar. 1, 2013 for EP Application No. 10822810.7.
European search report dated Jul. 15, 2013 for EP Application No. 11733492.
Ferber, D. Bridging the blood-brain barrier: new methods improve the odds of getting drugs to the brain cells that need them. PLoS Biol. Jun. 2007;5(6):e169: 1191-1194.
Fillebeen, et al. Receptor-mediated transcytosis of lactoferrin through the blood-brain barrier. J Biol Chem. Mar. 12, 1999;274(11):7011-17.
Flomen, et al. Determination of the organisation of coding sequences within the iduronate sulphate sulphatase (IDS)gene. Hum. Mol. Genet. 1993;2(1):5-10.
Forough, et al. Differential transforming abilities of non-secreted and secreted forms of human fibroblast growth factor-1. J Biol Chem. Feb. 5, 1993;268(4):2960-8.
Franco, et al. A cluster of sulfatase genes on Xp22.3: mutations in chondrodysplasia punctata (CDPX) and implications for warfarin embryopathy. Cell. Apr. 7, 1995;81(1):15-25.
Frenkel, et al. Modulation of Alzheimer's beta-amyloid neurotoxicity by site-directed single-chain antibody. J Neuroimmunol. Jul. 1, 2000;106(1-2):23-31.
Friden, et al. Blood-brain barrier penetration and in vivo activity of an NGF conjugate. Science. Jan. 15, 1993;259(5093):373-77.

(56) References Cited

OTHER PUBLICATIONS

Fu, et al. Neuroprotection in stroke in the mouse with intravenous erythropoietin-Trojan horse fusion protein. Brain Res. Jan. 19, 2011;1369:203-7. Epub Oct. 31, 2010.
Fukuchi, et al. Amelioration of amyloid load by anti-Abeta single-chain antibody in Alzheimer mouse model. Biochem Biophys Res Commun. May 26, 2006;344(1):79-86.
Fukuda et al. In vitro evolution of single-chain antibodies using mRNA display. Nucleic Acids Research, 2006; 34(19):e127.
Gardner, CJ et al. Growth, final height and endocrine sequelae in a UK population of patients with Hurler syndrome (MPS1H). J. Inherit Metab Dis. 34(2):489-97 (Apr. 2011).
Gehrmann, et al. Biochemical properties of recombinant human beta-glucuronidase synthesized in baby hamster kidney cells. Biochem J. 1994 Aug 1;301 ( Pt 3):821-8.
Gennaro, 2000. Remington: The Science and Practice of Pharmacy. 20 ed. (WAS: Remington's Pharmaceutical Sciences, Gennaro, AR, ed., 20th edition, 2000: Williams and Wilkins PA, USA).
Gillies, et al. Bi-functional cytokine fusion proteins for gene therapy and antibody-targeted tratment of cancer. 2002, Cancer Immunology and Immunotherapy, vol. 51, pp. 449-460.
Gografe, Sylvia I. et al. Mouse Model of Sanfilippo Syndrome Type B: Relation of Phenotypic Features to Background Strain. Comparative Medicine 53(6): 622-632 (Dec. 2003).
Golden, et al. Human blood-brain barrier leptin receptor. Binding and endocytosis in isolated human brain microvessels. J Clin Invest. Jan. 1, 1997;99(1):14-8.
Grasso, et al. Neuroprotection by erythropoietin administration after experimental traumatic brain injury. Brain Res. Nov. 28, 2007:1182:99-105.
Green-Sadan, et al. Transplantation of glial cell line-derived neurotrophic factor-expressing cells into the striatum and nucleus accumbens attenuates acquisition of cocaine self-administration in rats. Eur J Neurosci. Oct. 2003:18(7):2093-8.
Habgood, et al. Changes in blood-brain barrier permeability to large and small molecules following traumatic brain injury in mice. EurJ Neurosci. Jan. 2007;25(1):231-8.
Haisma, et al. Construction and characterization of a fusion protein of single-chain anti-CD20 antibody and human beta-glucuronidase for antibody-directed enzyme prodrug therapy. Blood. Jul. 1, 1998;92(1):184-90.
Hansson et al. Prediction of Alzheimer's disease using the CSF Abeta42/Abeta40 ratio in patients with mild cognitive impairment. Dement Geriatr Cogn Disord. 2007;23(5):316-20.
Hasselbalch, Steen G. et al. No Effect of Insulin on Glucose Blood-Brain Barrier Transport and Cerebral Metabolism in Humans, Diabetes, 48:1915-1921 (Oct. 1999).
He, et al. Autoregulation of glial cell line-derived neurotrophic factor expression: implications for the long-lasting actions of the anti-addiction drug, Ibogaine. FASEB J. Nov. 2006;20(13):E1820-E1827; 2420-22.
He, et al. Glial cell line-derived neurotrophic factor mediates the desirable actions of the anti-addiction drug ibogaine against alcohol consumption. J Neurosci. Jan. 19, 2005;25(3):619-28.
He, et al. Identification and characterization of the molecular lesion causing mucopolysaccharidosis type I in cats. Mol Genet Metab. 1999; 67(2):106-12.
Henikoff et al. Amino acid substitution matrices from protein blocks. PNAS USA 89:10915-10919 (1989).
Henikoff, et al. Predicting the effects of amino Acid substitutions on protein function. Annu Rev Genomics Hum Genet. 2006;7:61-80.
Hetman, et al. Neuroprotection by Brain-derived Neurotropic Factor Is Mediated by Extracellular Signal-regulated Kinase and Phoshatidylinositol 3-Kinase. The J of Bio Chem. 1999. 274 (32): 22569-80.
Holliger, et al. Engineered antibody fragments and the rise of single domains. Nat Biotechnol. Sep. 2005;23(9):1126-36.
Hoshaw, et al. Central administration of IGF-I and BDNF leads to long-lasting antidepressant-like effects. Brain Res. 2005. 1037: 204-8.

Hui et al., "Tumor Necrosis Factor Receptor-IgG Fusion Protein for Targeted Drug Delivery across the Human Blood-Brain Barrier," Mol. Pharm. vol. 6, No. 5, pp. 1536-1543 (2009).
Huston et al. Protein engineering of antibody binding sites: recovery of specific activity in an anti-digoxin single-chain Fv analogue produced in *Escherichia coli*. PNAS USA 85(16):5879-5883 (1988).
Ibanez et al. An extended surface of binding to Trk tyrosine kinase receptors in NGF and BDNF allows the engineering of a multifunctional pan-neurotrophin. EMBO J 12(6):2281-2293 (1993).
Ibanez, Structure-function relationships in the neurotrophin family. J Neurobiol. Nov. 1994;25(11):1349-61.
International Preliminary Report on Patentability and Written Opinion for International Application No. PCT/US2014/047082 dated Jan. 19, 2016.
International Preliminary Report on Patentability and Written Opinion dated Jan. 26, 2016 in PCT/US2014/038660.
International Preliminary Report on Patentability dated Jun. 1, 2010 for PCT/US2008/084718.
International search report and written opinion dated Feb. 22, 2011 for PCT/US2010/052113.
International search report and written opinion dated Feb. 22, 2013 for PCT/US2012/054520.
International search report and written opinion dated Feb. 27, 2009 for PCT/US2008/071121.
International search report and written opinion dated Apr. 8, 2011 for PCT/US2011/21418.
International search report and written opinion dated Jul. 1, 2008 for PCT/US2006/038587.
International search report and written opinion dated Sep. 7, 2010 for PCT/US2010/027882.
International search report and written opinion dated Sep. 16, 2008 for PCT/US2007/076316.
International search report and written opinion dated Oct. 29, 2014 for PCT/US2014/038660.
International search report and written opinion dated Dec. 15, 2014 for PCT Application No. PCT/US2014/047082.
Iwasaki, et al. Protective effect of interleukin-3 and erythropoietin on motor neuron death after neonatal axotomy. Neurol Res. Oct. 2002;24(7):643-6.
Japanese Application No. 2011-23913 Office Action dated Feb. 23, 2016.
Japanese Application No. 2014-043117 Office Action dated Apr. 7, 2016.
Japanese Application No. 2014544731 Office Action dated Jun. 14, 2016.
Japanese Patent Application No. 2014116085 Office Action dated Aug. 3, 2016.
Japanese Patent Application No. 2014-116085 Office Action dated Jan. 19, 2016.
Jefferies, et al. Analysis of lymphopoietic stem cells with a monoclonal antibody to the rat transferrin receptor. Immunology. Feb. 1985;54(2):333-41.
Jeffrey, et al. 26-10 Fab-digoxin complex: Affinity and specificity due to surface complementarity. Proc Natl. Acad. Sci USA. 1993; 90(21):10310-10314.
Jethwa, et al. 2005. Neuromedin U has a physiological role in the regulation of food intake and partially mediates the effects of leptin. American Journal of Physiology—Endocrinology and Metabolism 289: E301-E305.
Jiang, et al. BDNF Variation and Mood Disorders: A Novel Functional Promoter Polymorphism and Val66Met are Associated with Anxiety but Have Opposing Effects. 2005. Neuropsychopharmacology 30:1353-61.
Jones, et al. Determination of Tumor Necrosis Factor Binding Protein Disulfide Structure: Deviation of the Fourth Domain Structure from the TNFR/NGFR Family Cysteine-Rich Region Signature Biochemistry. 1997; 36: 14914-23.
Josse, et al. Identification of residues essential for human paraoxonase (PON1) arylesterase/organophosphatase activities. Biochemistry. Mar. 2, 1999;38(9):2816-25.
Josse, et al. Oligomeric states of the detergent-solubilized human serum paraoxonase (PON1). J Biot Chem. Sep. 6, 2002;277(36):33386-97.

(56) References Cited

OTHER PUBLICATIONS

Josse, et al. The active site of human paraoxonase (PON1). J Appl Toxicol. Dec. 2001;21 Suppl 1:S7-11.
Juul, et al. Erythropoietin concentrations in cerebrospinal fluid of nonhuman primates and fetal sheep following high-dose recombinant erythropoietin, Biol. Neonate. 2004;85:138-144.
Kabat et al. Sequences of Proteins of Immunological Interest. NIH Pub. No. 91/3242. Public Health Service, National Institutes of Health. 1:647-669 (1991).
Kakkis, et al. Overexpression of the human lysosomal enzyme alpha-L-iduronidase in Chinese hamster ovary cells. Protein Expr Purif. 1994; 5(3):225-32.
Karlin et al. Applications and statistics for multiple high-scoring segments in molecular sequences. PNAS USA 90:5873-5787 (1993).
Kashmiri, et al. SDR grafting—a new approach to antibody humanization. Methods. May 2005;36(1):25-34.
Kastin, et al. Glial cell line-derived neurotrophic factor does not enter normal mouse brain. Neuroscience Letters. 2003;340:239-41.
Kido, et al. 2000. Neuroprotective effects of brain-derived neurotropic factor in eyes with NMDA-induced neuronal death. Brain Research 884:59-67.
Kim, et al., Continuous Brain-derived Neurotropic Factor (BDNF) Infusion After Methylprednisolone Treatment in Severe Spinal Cord Injury. Journal of Korean Medical Science 2004;19: 113-22.
Kim, et al. Decreased paraoxonase-1 activity is a risk factor for ischemic stroke in Koreans. Biochem Biophys Res Commun. Dec. 7, 2007;364(1):157-62.
Kim, et al. N-terminal domains of native multidomain proteins have the potential to assist de novo folding of their downstream domains in vivo by acting as solubility enhancers. Protein Sci. Apr. 2007;16(4):635-43.
Kim et al. Protective effects of glial cell line-derived neurotrophic factor on hippocampal neurons after traumatic brain injury in rats. Journal of Neurosurgery 95:674-679 (2001).
Kitagawa, et al. Reduction of Ischemic Brain Injury by Topical Application of Glial Cell Line-Derived Neurotrophic Factor After Permanent Middle Cerebral Artery Occlusion in Rats. Stroke. 1998;29:1417-22.
Knaust, "Residues Critical for Formylglycine Formation and/or Catalytic Activity of Arylsulfatase A," Biochemistry, 37:13941-13946 (1998).
Kobayashi, et al. Intracerebral Infusion of Glial Cell Line-Derived Neurotrophic Factor Promotes Striatal Neurogenesis After Stroke in Adult Rats Stroke. 2006;37:2361-67.
Koehne, et al. Vascular endothelial growth factor and erythropoietin concentrations in cerebrospinal fluid of children with hydrocephalus. Childs Nerv Syst. Apr. 2002;18(3-4):137-41.
Krewson, et al. Distribution of nerve growth factor following direct delivery to brain interstitium. Brain Research 680: 196-206 (1995).
Kurbacher, et al. Continuous Low-Dose GM-CSF as Salvage Therapy in Refractory Recurrent Breast or Female Genital Tract Carcinoma. Oncology, 19(4) Supp 2: 23-26 (Apr. 2005).
Kurihara, et al. Imaging Brain Tumors by Targeting Peptide Radiopharmaceuticals through the Blood-Brain Barrier. Cancer Research 59: 6159-63 (1999).
Lai, et al. Structural determinants of Trk receptor specificities using BDNF-based neurotrophin chimeras. J Neurosci Res. Dec. 1, 1996;46(5):618-29.
Lang, et al. Randomized controlled trial of intraputamenal glial cell line-derived neurotrophic factor infusion in Parkinson disease. Annals of Neurology. 2006;59:459-66.
Lapchak, et al. Glial cell line-derived neurotrophic factor attenuates behavioural deficits and regulates nigrostriatal dopaminergic and peptidergic markers in 6-hydroxydopamine-lesioned adult rats: comparison of intraventricular and intranigral delivery. Neuroscience. 1997;78:61-72.
Lappi, et al. Expression and activities of a recombinant basic fibroblast growth factor-saporin fusion protein. J Biol Chem. Apr. 29, 1994;269(17):12552-8.

Lazar, et al. Transforming growth factor alpha: mutation of aspartic acid 47 and leucine 48 results in different biological activities. Mol Cell Biol. Mar. 1988;8(3):1247-52.
Lee, et al. Drug targeting to the brain using avidin-biotin technology in the mouse; (blood-brain barrier, monoclonal antibody, transferrin receptor, Alzheimer's disease). J Drug Target. 2000;8(6):413-24.
Lee, et al., Imaging Brain Amyloid of Alzheimer Disease In Vivo in Transgenic Mice With an Aβ Peptide Radiopharmaceutical. Journal of Cerebral Blood Flow and Metabolism 2002;22: 223-31.
Lenz, et al. Stoichiometric and catalytic scavengers as protection against nerve agent toxicity: a mini review. Toxicology. Apr. 20, 2007;233(1-3):31-9.
Lewin, B. Genes IV. Oxford University Press. 1990. p. 810.
Li, et al. Genetically engineered brain drug delivery vectors: cloning, expression and in vivo application of an anti-transferrin receptor single chain antibody-streptavidin fusion gene and protein. Protein Eng. Sep. 1999;12(9):787-96.
Lin, et al. GDNF: a glial cell line-derived neurotrophic factor for midbrain dopaminergic neurons. Science. 1993;260:1130-32.
Lin, et al. Structure-function relationships in glucagon: properties of highly purified des-His-1-, monoiodo-, and (des-Asn-28, Thr-29)(homoserine lactone-27)-glucagon. Biochemistry. Apr. 22, 1975;14(8):1559-63.
Liu, et al. Anti beta-amyloid (Abeta) SCFV inhibits Abeta aggregation and neurotoxicity (P4354). Neurobiology of Aging, Tarrytown, NY. 2004;25:S575-S576.
Liu, et al. Single chain variable fragments against beta-amyloid (Abeta) can inhibit Abeta aggregation and prevent abeta-induced neurotoxicity. Biochemistry. Jun. 8, 2004;43(22):6959-67.
Lu, et al. Cationic Liposome-Mediated GDNF Gene Transfer after Spinal Cord Injury. Journal of Neurotrauma. 2002;19:1081-1090.
Lu et al., "Expression in CHO Cells and Pharmacokinetics and Brain Uptake in the Rhesus Monkey of an IgG-Iduronate-2-Sulfatase Fusion Protein," Biotechnology and Bioengineering, vol. 108, No. 8, pp. 1954-1964 (2011).
Lu et al., "Genetic Engineering of a Bifunctional IgG fusion protein with iduronate-2-sulfatase," Bioconjugate Chemistry, 21(1) pp. 151-156 (2010).
Lukatela, et al. Crystal structure of human arylsulfatase A: the aldehyde function and the metal ion at the active site suggest a novel mechanism for sulfate ester hydrolysis. Biochemistry. Mar. 17, 1998;37(11):3654-64.
Ma, et al. Erythropoietin protects PC12 cells from beta-amyloid(25-35)-induced apoptosis via PI3K/Akt signaling pathway. Neuropharmacology. May-Jun. 2009;56(6-7):1027-34.
MacCallum et al. Antibody-antigen interactions: contact analysis and binding site topography. J Mol Biol. 262(5):732-745 (1996).
Manoutcharian, et al. Amyloid-beta peptide-specific single chain Fv antibodies isolated from an immune phage display library. J Neuroimmunol. 2003; 145(1-2):12-7.
Martell, et al. Efficacy of transferrin receptor-targeted immunotoxins in brain tumor cell lines and pediatric brain tumors. Cancer Res. Mar. 15, 1993;53(6):1348-53.
Martin et al. Crystal structure at 2.8 A of an FcRn/heterodimeric Fc complex: mechanism of pH-dependent binding. Mol Cell. Apr. 2001;7(4):867-77.
Marvin, et al. Recombinant approaches to IgG-like bispecific antibodies. Acta Pharmacol Sin. Jun. 2005;26(6):649-58.
Matis, et al. Erythropoietin in spinal cord injury. Eur Spine J. Mar. 2009;18(3):314-23.
McGrath, et al. Bifunctional fusion between nerve growth factor and a transferrin receptor antibody. J Neurosci Res. Jan. 15, 1997;47(2):123-33.
McLendon et al. Radiotoxicity of systemically administered 211At-labeled human/mouse chimeric monoclonal antibody: a long-term survival study with histologic analysis. Int J Radiat Oncol Biol Phys. Sep. 1, 1999;45(2):491-9.
Menzies, et al. Contributions of ions and albumin to the formations and resolution of ischemic brain edema. Journal of Neurosurgery 78: 257-266. (1993).
Messer, et al. Role for GDNF in biochemical and behavioral adaptations to drugs of abuse. Neuron. Apr. 2000;26(1):247-57.

(56) References Cited

OTHER PUBLICATIONS

Mori, et al. Differential expression patterns of TrkB ligands in the macaque monkey brain. Developmental Neuroscience 15: 2507-11 (2004).
Muenzer, et al. A phase II/III clinical study of enzyme replacement therapy with idursulfase in mucopolysaccharidosis II (Hunter syndrome). Genet Med Aug. 2006;8(8):465-73.
Muenzer, et al. Advances in the treatment of mucopolysaccharidosis type I. N Engl J Med. May 6, 2004;350(19):1932-4.
Nawashiro et al., "Neuroprotective effects of TNF binding protein in focal cerebral ischemia," Brain Research, vol. 778, No. 2, pp. 265-271 (1997).
NCBI GenBank Accession No. NM-000487 (Oct. 23, 2011).
NCBI Reference Sequence: NM-000202.5 *Homo sapiens* iduronate 2-sulfatase (IDS), transcript variant 1, mRNA. 1992. http://www.ncbi.nlm.nih.gov/nuccore/NM000202.5.
Needleman et al. A general method applicable to the search for similarities in the amino acid sequence of two proteins. J. Mol. Biol. 48:443-453 (1970).
Ng, et al. Paraoxonase-1 deficiency in mice predisposes to vascular inflammation, oxidative stress, and thrombogenicity in the absence of hyperlipidemia. Cardiovasc Pathol. Jul.-Aug. 2008;17(4):226-32.
Ng, et al. Predicting the effects of amino acid substitutions on protein function. Annual Review of Genomics and Human Genetics. 2006;7:61-80.
Notice of allowance dated Jan. 22, 2014 for U.S. Appl. No. 12/323,232.
Notice of allowance dated Jan. 28, 2010 for U.S. Appl. No. 11/841,623.
Notice of Allowance dated Mar. 20, 2013 for U.S. Appl. No. 13/609,099.
Notice of allowance dated Apr. 1, 2011 for U.S. Appl. No. 11/245,546.
Notice of Allowance dated Apr. 2, 2013 for U.S. Appl. No. 11/841,594.
Notice of allowance dated May 20, 2014 for U.S. Appl. No. 12/901,481.
Notice of allowance dated Aug. 9, 2011 for U.S. Appl. No. 11/245,710.
Notice of allowance dated Aug. 12, 2014 for U.S. Appl. No. 14/194,463.
Notice of allowance dated Sep. 23, 2013 for U.S. Appl. No. 12/756,093.
Notice of allowance dated Sep. 25, 2013 for U.S. Appl. No. 13/862,250.
Notice of allowance dated Oct. 7, 2013 for U.S. Appl. No. 12/323,232.
Notice of allowance dated Oct. 28, 2011 for U.S. Appl. No. 12/688,842.
Notice of allowance dated Oct. 31, 2011 for U.S. Appl. No. 11/245,546.
Notice of allowance dated Dec. 13, 2013 for U.S. Appl. No. 13/862,250.
Notice of allowance dated Dec. 16, 2013 for U.S. Appl. No. 12/756,093.
Notice of allowance dated Dec. 19, 2014 for U.S. Appl. No. 12/179,806.
Notice of allowance dated Dec. 23, 2013 for U.S. Appl. No. 11/841,541.
Nutt, et al., Randomized, double-blind trial of glial cell line-derived neurotropic factor (GDNF) in PD. Neurology 2003;60: 69-73.
Ober, et al. Differences in promiscuity for antibody-FcRn interactions across species: implications for therapeutic antibodies. Int Immunol. Dec. 2001;13(12):1551-9.
Office action dated Jan. 9, 2013 for U.S. Appl. No. 12/901,481.
Office action dated Jan. 15, 2008 for U.S. Appl. No. 11/245,710.
Office action dated Jan. 15, 2009 for U.S. Appl. No. 11/841,623.
Office action dated Jan. 23, 2009 for U.S. Appl. No. 11/245,546.
Office action dated Feb. 2, 2010 for U.S. Appl. No. 11/245,710.
Office action dated Feb. 10, 2006 for U.S. Appl. No. 10/307,165.
Office action dated Feb. 16, 2011 for U.S. Appl. No. 11/893,281.
Office action dated Feb. 16, 2011 for U.S. Appl. No. 12/150,983.
Office action dated Feb. 22, 2006 for U.S. Appl. No. 10/307,276.
Office action dated Mar. 1, 2007 for U.S. Appl. No. 10/307,165.
Office action dated Mar. 7, 2011 for U.S. Appl. No. 12/558,348.
Office action dated Mar. 10, 2010 for U.S. Appl. No. 12/179,806.
Office action dated Mar. 18, 2011 for U.S. Appl. No. 12/574,571.
Office action dated Mar. 26, 2010 for U.S. Appl. No. 11/841,594.
Office action dated Mar. 26, 2010 for U.S. Appl. No. 12/323,232.
Office action dated Apr. 6, 2011 for U.S. Appl. No. 11/245,710.
Office action dated Apr. 8, 2014 for U.S. Appl. No. 13/141,682.
Office action dated Apr. 9, 2007 for U.S. Appl. No. 10/307,276.
Office action dated Apr. 13, 2007 for U.S. Appl. No. 11/245,710.
Office action dated Apr. 24, 2013 for U.S. Appl. No. 12/179,806.
Office action dated May 6, 2014 for U.S. Appl. No. 14/144,460.
Office action dated May 6, 2015 for U.S. Appl. No. 14/281,803.
Office action dated May 9, 2008 for U.S. Appl. No. 11/061,956.
Office action dated May 12, 2010 for U.S. Appl. No. 11/893,281.
Office action dated May 13, 2011 for U.S. Appl. No. 12/688,842.
"Office action dated May 19, 2015 for U.S. Appl. No. 13/141,682."
Office action dated May 23, 2006 for U.S. Appl. No. 11/061,956.
Office action dated Jun. 3, 2008 for U.S. Appl. No. 11/245,710.
Office action dated Jun. 17, 2009 for U.S. Appl. No. 11/841,541.
Office action dated Jun. 27, 2011 for U.S. Appl. No. 11/245,546.
Office action dated Jun. 30, 2014 for U.S. Appl. No. 12/179,806.
Office action dated Jul. 1, 2010 for U.S. Appl. No. 11/245,546.
Office action dated Jul. 2, 2008 for U.S. Appl. No. 11/245,546.
Office action dated Jul. 2, 2009 for U.S. Appl. No. 11/245,710.
Office action dated Jul. 19, 2006 for U.S. Appl. No. 10/307,276.
Office action dated Jul. 20, 2012 for U.S. Appl. No. 12/756,093.
Office action dated Jul. 31, 2009 for U.S. Appl. No. 12/179,806.
Office action dated Aug. 15, 2013 for U.S. Appl. No. 13/141,682.
Office action dated Aug. 17, 2007 for U.S. Appl. No. 10/307,165.
Office action dated Aug. 18, 2006 for U.S. Appl. No. 10/307,165.
Office action dated Aug. 20, 2009 for U.S. Appl. No. 12/323,232.
Office action dated Sep. 15, 2010 for U.S. Appl. No. 12/150,983.
Office action dated Sep. 20, 2007 for U.S. Appl. No. 11/245,710.
Office action dated Sep. 24, 2009 for U.S. Appl. No. 11/841,623.
Office action dated Oct. 12, 2010 for U.S. Appl. No. 11/245,710.
Office action dated Oct. 13, 2009 for U.S. Appl. No. 11/893,281.
Office action dated Oct. 15, 2007 for U.S. Appl. No. 11/245,710.
Office action dated Oct. 18, 2011 for U.S. Appl. No. 11/245,546.
Office action dated Oct. 20, 2009 for U.S. Appl. No. 11/245,546.
Office action dated Oct. 20, 2014 for U.S. Appl. No. 13/141,682.
Office action dated Oct. 22, 2013 for U.S. Appl. No. 12/901,481.
Office action dated Oct. 29, 2007 for U.S. Appl. No. 10/307,276.
Office action dated Oct. 30, 2009 for U.S. Appl. No. 11/841,594.
Office action dated Nov. 1, 2012 for U.S. Appl. No. 11/841,594.
Office action dated Nov. 4, 2013 for U.S. Appl. No. 12/179,806.
Office action dated Nov. 8, 2007 for U.S. Appl. No. 11/245,546.
Office action dated Nov. 10, 2008 for U.S. Appl. No. 11/245,710.
Office action dated Nov. 13, 2006 for U.S. Appl. No. 11/245,710.
Office action dated Nov. 13, 2007 for U.S. Appl. No. 11/061,956.
Office action dated Nov. 26, 2012 for U.S. Appl. No. 13/609,099.
Office action dated Nov. 26, 2014 for U.S. Appl. No. 14/144,460.
Office action dated Dec. 14, 2011 for U.S. Appl. No. 12/574,571.
Office action dated Dec. 16, 2009 for U.S. Appl. No. 11/841,541.
Office action dated Dec. 21, 2006 for U.S. Appl. No. 11/061,956.
Office action dated Mar. 26, 2013 for U.S. Appl. No. 11/841,541.
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Orcutt, et al. A modular IgG-scFv bispecific antibody topology. Protein Eng Des Sel. Apr. 2010;23(4):221-8. doi: 10.1093/protein/gzp077. Epub Dec. 17, 2009.
Osbourn, et al. Directed selection of MIP-1 alpha neutralizing CCR5 antibodies from a phage display human antibody library. Nat Biotechnol. Aug. 1998;16(8):778-81.
Padlan, et al. Identification of specificity-determining residues in antibodies. FASEB J. 1995; 9(1):133-9.
Padlan, et al. Structure of an antibody-antigen complex: crystal structure of the HyHEL-10 Fab-lysozyme complex. Proc Natl Acad Sci U S A. Aug. 1989;86(15):5938-42.
Padridge, William M. Blood-brain drug targeting enables neuroprotection in brain ischemia following delayed intravenous administration of neurothrophins, Advances in Experimental Medicine and Biology, 543:397-430 (Jan. 1, 2002).

(56) References Cited

OTHER PUBLICATIONS

Paragh, et al. Ciprofibrate increases paraoxonase activity in patients with metabolic syndrome. Br J Clin Pharmacol. Jun. 2006;61(6):694-701.
Pardridge, Biopharmaceutical drug targeting to the brain. Journal of Drug Targeting, 18(3): 157-167 (2010).
Pardridge, The Blood-Brain Barrier: Bottleneck in Brain Drug Development. NeuroRx: The Journal of the American Society for Experimental NeuroTherapeutics 2: 3-14 (2005).
Pardridge. "Blood-brain barrier delivery of protein and non-viral gene therapeutics with molecular Trojan horses," Journal of Controlled Release, vol. 122, No. 3, pp. 345-348 (2007).
Pardridge., Blood-Brain Barrier Drug Targeting: The Future of Brain Drug Development. Molecular Interventions, 3 (2003): 90-105.
Pardridge, Brain drug targeting: The future of brain drug development. Cambridge University Press (2001).
Pardridge, Drug Targeting to the Brain. Pharm Res 24:1733-44 (2007).
Pardridge, et al. Human insulin receptor monoclonal antibody undergoes high affinity binding to human brain capillaries in vitro and rapid transcytosis through the blood-brain barrier in vivo in the primate. Pharm Res. 12(6):807-16 (1995).
Pardridge et al., "Biologic TNF[alpha]-inhibitors that cross the human blood-brain barrier," Bioengineered Bugs. vol. 1, No. 4, pp. 231-234 (2010).
Pardridge, et al. Combined Use of Carboxyl-Directed Protein Pegylation and Vector-Mediated Blood-Brain Barrier Drug Delivery System Optimizes Brain Uptake of Brain-Derived Neurotrophic Factor Following Intravenous Administration. Pharmaceutical Research 15 (4): 576-582 (1998).
Pardridge et al. Drug and gene targeting to the brain with molecular Trojan horses. Nat Rev Drug Discov., 1.2 (2002): 131-9.
Pardridge, et al. Drug Transport across the blood-brain barrier. Journal of Cerebral Blood Flow & Metabolism. 32; 1959-1972(2012).
Pardridge, et al. Human Blood-Brain Barrier Transferrin Receptor. Metabolism 36: 892-95 (1987).
Pardridge, et al. Transport of histone through the blood-brain barrier. J Pharmacol Exp Ther. Dec;251(3):821-6. (1989).
Pardridge, et al. Transport of Human Recombinant Brain-Derived Neurotrophic Factor (BDNF) Through the Rat Blood-Brain Barrier in Vivo Using Vector-Mediated Peptide Drug Delivery. Pharmaceutical Research 11 (5): 738-46 (1994).
Pardridge, Neuroprotection in stroke: is it time to consider large-molecule drugs? Drug Discovery Today 6: 751-53 (2001).
Pardridge, Neurotrophins, neuroprotection and the blood-brain barrier. Current Opinion in Investigational Drugs 3 (12): 1753-57 (2002).
Pardridge, "Re-engineering biopharmaceuticals for delivery to brain with molecular Trojan horses," Bioconjugate Chemistry, vol. 19, No. 7, pp. 1327-1338 (2008).
Pardridge, The Blood-Brain Barrier and Neurotherapeutics. NeuroRx: The Journal of the American Society for Experimental NeuroTherapeutics 2 (1): 1-2 (2005).
Pardridge, Tyrosine Hydroxylase Replacement in Experimental Parkinson's Disease with Transvascular Gene Therapy. NueuoRx: Journal of the American Society for Experimental NeuroTherapeutics. 2(1):129-138. (2005).
Park, et al. Production and characterization of fusion proteins containing transferrin and nerve growth factor. J Drug Target. 1998;6(1):53-64.
Patel, et al. Intraputamenal infusion of glial cell line-derived neurotrophic factor in PD: A two-year outcome study. Annals of Neurology. 2005;57:298-302.
Paul. Fundamental Immunology, 3rd Edition, Chapter 9, pp. 292-295 (1993).
Pearson, et al. Improved Tools for Biological Sequence Comparison. Proc. Nat'l Acad. Sci. USA. 85 (1988): 2444-48.
Pearson, Rapid and sensitive sequence comparison with FASTP and FASTA. Meth. Enzymol. 1990;183:63-98.

Pencea, et al. Infusion of Brain-Derived Neurotrophic Factor into the Lateral Ventricle of the Adult Rat Leads to New Neurons in the Parenchyma of the Striatum, Septum, Thalamus, and Hypothalamus. The Journal of Neuroscience 2001 21 (17): 6706-17.
Penichet, et al. An antibody-avidin fusion protein specific for the transferrin receptor serves as a delivery vehicle for effective brain targeting: initial applications in anti-HIV antisense drug delivery to the brain. J Immunol. Oct. 15, 1999;163(8):4421-26.
Peppel; et al., "A tumor necrosis factor (TNF) receptor-IgG heavy chain chimeric protein as a bivalent antagonist of TNF activity.", J Exp Med, Dec. 1, 1991, 174(6), 1483-9.
Pluckthun. Chapter 11: Antibodies from *Escherichia coli*. In the Pharmacology of Monoclonal Antibodies. 113:269-315 (1994).
Polito et al., "IDS Crossing of the Blood-Brain Barrier Corrects CNS Defects in MPSII Mice," Amer. Journ. Human Genetics, vol. 85, No. 2, pp. 296-301 (2009).
Olson, et al. Role of growth factors in degeneration and regeneration in the central nervous system; clinical experiences with NGF in Parkinson's and Alzheimer's diseases. J. Neurol. 241:S12-S15 (1994).
Pregi, et al. TNF-alpha-induced apoptosis is prevented by erythropoietin treatment on SH-SY5Y cells. Exp Cell Res. Feb. 1, 2009;315(3):419-31. Epub Nov. 20, 2008.
Preston, et al. 1997. Evidence for pore-like opening of the blood-brain barrier following forebrain ischemia in rats. Brain Research 761: 4-10.
Prince, et al. Lipoprotein receptor binding, cellular uptake, and lysosomal delivery of fusions between the receptor-associated protein (RAP) and alpha-L-iduronidase or acid alpha-glucosidase. J Biol Chem. Aug. 13, 2004;279(33):35037-46. Epub May 31, 2004.
Qi, et al. Binding and cytotoxicity of conjugated and recombinant fusion proteins targeted to the gonadotropin-releasing hormone receptor. Cancer Res. Mar. 15, 2004;64(6):2090-5.
Raghavan, et al. Analysis of the pH dependence of the neonatal Fc receptor/immunoglobulin G interaction using antibody and receptor variants. Biochemistry. Nov. 14, 1995;34(45):14649-57.
Ratliff-Schaub, et al. 2005. Randomized controlled trial of transdermal secretion on behavior of children with autism. Autism 9 (3): 256-65.
Reiber, et al. Protein transfer at the blood cerebrospinal fluid barrier and the quantitation of the humoral immune response within the central nervous system. Clin Chim Acta. Mar. 30, 1987;163(3):319-28.
Rempel, et al. A homology model for human α-L-Iduronidase: Insights into human disease. Mol. Genetics and Met. 2005; 85:28-37.
Robinson, et al. The structures of the neurotrophin 4 homodimer and the brain-derived neurotrophic factor / neurotrophin 4 heterodimer reveal a common Trk-binding site. Protein Science 1999 8: 2589-97.
Rochu, et al. Human paraoxonase: a promising approach for pretreatment and therapy of organophosphorus poisoning. Toxicology. Apr. 20, 2007;233(1-3):47-59.
Rohrback, et al. Therapeutic antibodies and antibody fusion proteins. Biotechnol Genet Eng Rev. 2003;20:137-63.
Rossolini et al. Use of deoxyinosine-containing primers vs degenerate primers for polymerase chain reaction based on ambiguous sequence information. Mol Cell Probes 8(2):91-98 (1994).
Rudikoff, et al. Single amino acid substitution altering antigen-binding specificity. Proc Natl Acad Sci U S A. Mar. 1982;79(6):1979-83.
Ruiz-Leon, et al. Induction of Tyrosine Kinase Receptor B by Retinoic Acid Allows Brain-Derived Neurotrophic Factor-Induced Amyloid Precursor Protein Gene Expression in Human SHSY5Y Neuroblastoma Cells. Neuroscience 120;2003:1019-26.
Rybak, et al. Humanization of immunotoxins. Proc Natl Acad Sci U S A. Apr. 15, 1992;89(8):3165-9.
Sakanaka, et al. In vivo evidence that erythropoietin protects neurons from ischemic damage. Proc Natl Acad Sci U S A. Apr. 14, 1998;95(8):4635-40.
Sakane, et al. Carboxyl-directed Pegylation of Brain-derived Neurotrophic Factor Markedly Reduces Systemic Clearance with Minimal Loss of Biologic Activity. Pharmaceutical Research 1997 14(8):1085-1091.

(56) References Cited

OTHER PUBLICATIONS

Sampson et al. Unarmed, tumor-specific monoclonal antibody effectively treats brain tumors. Proc Natl Acad Sci U S A. Jun. 20, 2000;97(13):7503-8.
Sardiello, et al. Sulfatases and sulfatase modifying factors: an exclusive and promiscuous relationship. Hum Mol Genet. Nov. 1, 2005;14(21):3203-17. Epub Sep. 20, 2005.
Sariola, et al. Novel functions and signalling pathways for GDNF. J Cell Sci. Oct. 1, 2003;116(Pt 19):3855-62.
Schabitz, et al. Intraventricular Brain-Derived Neurotrophic Factor Reduces Infarct Size After Focal Cerebral Ischemia in Rats. Journal of Cerebral Blood Flow and Metabolism 1997;17: 500-6.
Schlachetzki, et al. Expression of the neonatal Fc receptor (FcRn) at the blood-brain barrier. J Neurochem. Apr. 2002;81(1):203-6.
Schlachetzki, et al. Gene therapy of the brain: the trans-vascular approach. Neurology. Apr. 27, 2004;62(8):1275-81.
Schoonjans, R. et al., "Fab Chains as an Efficient Heterodimerization Scaffold for the Production of Recombinant Bispecific and Trispecific Antibody Derivatives." The Journal of Immunology, 2000, 165 (12): 7050-7057.
Schuchman, et al. Human alpha-L-iduronidase: Purification and properties of the high uptake (higher molecular weight) and the low uptake (processed) forms. J. Bioi. Chem. 1984; 259(5):3132-3140.
Schwartz, et al. A superactive insulin: [B10-aspartic acid]insulin(human). Proc Natl Acad Sci U S A. Sep. 1987;84(18):6408-11.
Scott, et al. Human alpha-L-iduronidase: cDNA isolation and expression. Proc Natl Acad Sci U S A. Nov. 1, 1991;88(21):9695-9.
Sellers, On the theory and computation of evolutionary distances. SIAM Journal on Applied Mathematics. 1974;26:787.
Selmayr, et al. Induction of tumor immunity by autologous B lymphoma cells expressing a genetically engineered idiotype. Gene Ther. May 1999;6(5):778-84.
Sevin, C. et al. Intracerebral adeno-associated virus-mediated gene transfer in rapidly progressive forms of metachromatic leukodystrophy. Human Molecular Genetics 15(1); 53-64 (2006).
Shanafelt, et al. Identification of critical amino acid residues in human and mouse granulocyte-macrophage colony-stimulating factor and their involvement in species specificity. J Biol Chem. Jul. 25, 1991;266(21):13804-10.
Shin, et al. Transferrin-antibody fusion proteins are effective in brain targeting, Proceedings of the Natinal Academy of Sciences, 1995. vol. 92, pp. 2820-2824.
Shipley, et al. The role of glycosylation and phosphorylation in the expression of active human beta-glucuronidase. J Biol Chem. Jun. 5, 1993;268(16):12193-8.
Sidhu, Navdeep S. Structure of sulfamidase provides insight into the molecular pathology of mucopolysaccharidosis IIIA. Acta Cryst. (2014). D70, 1321-1335.
Sifuentes, et al. A follow-up study of MPS I patients treated with laronidase enzyme replacement therapy for 6 years. Mol Genet Metab. Feb. 2007;90(2):171-80. Epub Sep. 29, 2006.
Siren, et al., Erythropoetin prevents neuronal apoptosis after cerebral ischemia and metabolic stress. Proc Natl Acad Sci U S A. Mar. 27, 2001;98(7):4044-9.
Sivakumur et al., Bone marrow transplantation in mucopolysaccharidosis type IIIA: A comparison of an early treated patient with his untreated sibling. J. Inher. Metab. Dis., 22(849):849-850 (1999).
Skolnick, et al. From genes to protein structure and function: novel applications of computational approaches in the genomic era. Trends Biotechnol. Jan. 2000;18(1):34-9. Review.
Smith, et al. Comparison of Biosequences. Advances in Applied Mathematics. 1981;2: 482-489.
Soukharev, et al. A fluorogenic substrate for detection of organophosphatase activity. Anal Biochem. Apr. 1, 2004;327(1):140-8.
Spina, et al., Brain-Derived Neurotrophic Factor Protects Dopamine Neurons Against 6-Hydroxydopamine and N-Methyl-4-Phenylpyridinium Ion Toxicity: Involvement of the Glutathione System. Journal of Neurochemistry1992;59 (1): 99-106.
Strauss, et al., Brain-derived neurotrophic factor variants are associated with childhood-onset mood disorder: confirmation in a Hungarian sample. Molecular Psychiartry 2005;10: 861-67.
Stroobants, S. et al. Intracerebroventricular enzyme infusion corrects central nervous system pathology and dysfunction in a mouse model of metachromatic leukodystrophy.Human Molecular Genetics 20(4); 2760-2769 (2011).
Sukegawa-Hayasaka, et al. Effect of Hunter disease (mucopolysaccharidosis type II) mutations on molecular phenotypes of iduronate-2-sulfatase; enzymatic activity, protein processing and structural analysis. J Inherit Metab Dis 2006;29:755-761.
Sumbria; et al., "Brain protection from stroke with intravenous TNFα decoy receptor-Trojan horse fusion protein", J Cereb Blood Flow Metab, Oct. 2012, 32(10), 1933-8.
Sun et al. Comparison of the capability of GDNF, BDNF, or both, to protect nigrostriatal neurons in a rat model of Parkinson's disease. Brain Research 1052(2);119-29 (Aug. 9, 2005).
Takahashi, et al., Inhibition of cell growth and tumorigenesis of human glioblastoma cells by a neutralizing antibody against human basic fibroblast growth factor. Federation of European Biochemical Societies 1991;288 (1,2): 65-71.
The BDNF Study Group (Phase III). A controlled trial of recombinant methionyl human BDNF in ALS. Neurology 1999;52: 1427-33.
Thoenen, et al. Neurotrophins: from enthusiastic expectations through sobering experiences to rational therapeutic approaches. Nature Neuroscience Supplement 5;2002:1046-50.
Thompson, et al. Improved binding of a bivalent single-chain immunotoxin results in increased efficacy for in vivo T-cell depletion. Protein Eng. Dec. 2001;14(12):1035-41.
Tobinick et al., "Perispinal etanercept for neuroinflammatory disorders," Drug Discovery Today, vol. 14, No. 3-4, pp. 168-177 (2009).
Tomatsu, et al. Murine model (GaIns(tm(C76S)slu)) of MPS IVA with missense mutation at the active site cystein conserved among sulfatase proteins. Mol Genet Metab. Jul. 2007;91(3):251-8.
Tougou, et al. Paraoxonase has a major role in the hydrolysis of prulifloxacin (NM441), a prodrug of a new antibacterial agent. Drug Metab Dispos. Apr. 1998;26(4):355-9.
Traunecker, et al. Highly efficient neutralization of HIV with recombinant CD4-immunoglobulin molecules. Nature, 339(6219);68-70 (May 4, 1989).
Triguero et al. Capillary depletion method for quantification of blood-brain barrier transport of circulating peptides and plasma proteins. J Neurochem. 1990; 54(6):1882-8.
Tsukahara, et al. The Role of Brain-derived Neurotrophic Factor in Transient Forebrain Ischemia in the Rat Brain. Neurosurgery 34 (2);1994:323-31.
Udupa, KB. Functional significance of erythropoietin receptor on tumor cells. World J. Gastroenterol. 12(46):7460-7462 (Dec. 14, 2006).
Um, et al. A "classical" homodimeric erythropoietin receptor is essential for the antiapoptotic effects of erythropoietin on differentiated neuroblastoma SH-SY5Y and pheochromocytoma PC-12 cells. Cell Signal. Mar. 2007;19(3):634-45.
Unger, et al. Recombinant α-iduronidase: characterization of the purified enzyme and correction of mucopolysaccharidosis type I fibroblasts. Biochem J. 1994; 384:43-49.
U.S. Appl. No. 13/141,682 Final Office Action dated Nov. 10, 2015.
U.S. Appl. No. 13/141,682 Non-Final Office Action dated Mar. 30, 2016.
U.S. Appl. No. 13/141,682 Notice of Allowance dated Aug. 22, 2016.
U.S. Appl. No. 14/144,460, filed Dec. 30, 2013.
U.S. Appl. No. 14/144,460 Final Office Action dated Nov. 9, 2016.
U.S. Appl. No. 14/144,460 Non-Final Office Action dated Apr. 21, 2016.
U.S. Appl. No. 14/144,460 Non-Final Office Action dated Apr. 4, 2018.
U.S. Appl. No. 14/192,792 Non-Final Office Action dated Feb. 20, 2018.
U.S. Appl. No. 14/192,792 Office Action dated Apr. 14, 2017.
U.S. Appl. No. 14/192,792 Office Action dated Aug. 23, 2016.

(56) References Cited

OTHER PUBLICATIONS

U.S. Appl. No. 14/281,803 Non-Final Office Action dated Nov. 16, 2017.
U.S. Appl. No. 14/281,803, filed May 19, 2014.
U.S. Appl. No. 14/281,803 Final Office Action dated Apr. 28, 2017.
U.S. Appl. No. 14/281,803 Office Action dated Jun. 30, 2016.
U.S. Appl. No. 14/305,402, filed Jun. 16, 2014.
U.S. Appl. No. 14/305,402 Non-Final Office Action dated Jul. 6, 2017.
U.S. Appl. No. 14/305,402 Notice of Allowability dated May 15, 2018.
U.S. Appl. No. 14/305,402 Notice of Allowance dated Feb. 28, 2018.
"U.S. Appl. No. 14/305,402 Office Action dated Jan. 3, 2017".
U.S. Appl. No. 14/538,721 Non-Final Office Action dated Apr. 13, 2017.
"U.S. Appl. No. 14/594,047 Final Office Action dated Jun. 2, 2016".
U.S. Appl. No. 14/594,047 Final Office Action dated Oct. 18, 2017.
U.S. Appl. No. 14/594,047 Office Action dated Jan. 18, 2017.
U.S. Appl. No. 14/606,239 Office Action dated Jun. 10, 2016.
U.S. Appl. No. 14/906,259 Non-final Office Action dated May 4, 2017.
U.S. Appl. No. 14/994,067 Final Office Action dated Oct. 31, 2017.
U.S. Appl. No. 14/994,067 Non-Final Office Action dated Jan. 17, 2017.
U.S. Appl. No. 15/397,649 Non-Final Office Action dated Mar. 1, 2018.
U.S. Appl. No. 14/144,460 Office Action dated Aug. 17, 2015.
U.S. Appl. No. 14/192,792 Final Office Action dated Oct. 30, 2015.
U.S. Appl. No. 14/192,792.Office Action dated Jul. 17, 2015.
U.S. Appl. No. 14/538,721 Office Action dated Dec. 3, 2015.
U.S. Appl. No. 14/538,721 Office Action dated Sep. 8, 2016.
U.S. Appl. No. 14/594,047 Advisory Office Action dated Oct. 17, 2016.
U.S. Appl. No. 14/594,047 Office Action dated Aug. 26, 2015.
U.S. Appl. No. 14/606,239 Notice of Allowability dated Oct. 21, 2016.
U.S. Appl. No. 14/606,239 Notice of Allowance dated Oct. 3, 2016.
Vahabzadeh, A. et al. Effects of changes in rat brain glucose on serotonergic and noradrenergic neurons. Eur. J. Neurosci. 7(2):175-9 (Feb. 1, 1995).
Voznyi, et al. A fluorimeteric enzyme assay for the diagnosis of MPS II (Hunter disease). J Inherit Metab Dis. 2001;24:675-80.
Walker, F. et al., Specific binding of radioiodinated granulocyte-macrophage colony-stimulating factor to hemopoietic cells. The EMBO Journal 4(4); pp. 933-939 (1985).
Wang, et al. Identification of the key amino acids of glial cell line-derived neurotrophic factor family receptor alphal involved in its biological function. J Biol Chem. Jan. 2, 2004;279(1):109-16.
Ward, E.S. Binding activities of a repertoire of single immunoglobulin variable domains secreted from *Escherichia coli*. Nature. Oct. 12, 1989;341(6242):544-546.
Warrington, et al. Human monoclonal antibodies reactive to oligodendrocytes promote remyelination in a model of multiple sclerosis. Proc Natl Acad Sci U S A. Jun. 6, 2000;97(12):6820-5.
Weich, et al. Interleukin-3/erythropoietin fusion proteins: in vitro effects on hematopoietic cells. Exp Hematol. May 1993;21(5):647-55.
Whetstone, et al. Blood-spinal cord barrier after spinal cord injury: relation to revascularization and wound healing. J Neurosci Res. Oct. 15, 2003;74(2):227-39.
Whittaker, et al. Characterization of the functional insulin binding epitopes of the full-length insulin receptor. J Biol Chem. 2005;280(22):20932-6.
Wiesenhofer, et al. Glial cell line-derived neurotrophic factor (GDNF) and its receptor (GFR-α1) are strongly expressed in human gliomas. Acta Neuropathol. (Berl). 2000;99:131-37.

Wraith, et al. Enzyme replacement therapy for mucopolysaccharidosis I: a randomized, double-blinded, placebo-controlled, multinational study of recombinant human alpha-L-iduronidase (laronidase). J Pediatr. May 2004;144(5):581-8.
Wraith, et al. Mucopolysaccaridosis type II (Hunter syndrome): a clinical review and recommendations for treatment in the era of enzyme replacement therapy. Eur J Pediatr. Mar. 2008;167(3):267-77.
Wraith, J. Enzyme replacement therapy in mucopolysaccharidosis type I: progress and emerging difficulties. J Inherit Metab Dis. Apr. 2001;24(2):245-50.
Wu, et al. Drug targeting of a peptide radiopharmaceutical through the primate blood-brain barrier in vivo with a monoclonal antibody to the human insulin receptor. J Clin Invest. Oct. 1, 1997;100(7):1804-12.
Wu, et al. Neuroprotection in Experimental Stroke with Targeted Neurotrophins. NeuroRX: The Journal of the American Society for Experimental NeuroTherapeutics. 2005;2(1):120-128.
Wu, et al. Neuroprotection with noninvasive neurotrophin delivery to the brain. Proc Natl Acad Sci U S A. Jan. 5, 1999;96(1):254-9.
Wu, et al. Simultaneous targeting of multiple disease mediators by a dual-variable-domain immunoglobulin. Nat Biotechnol. Nov. 2007;25(11):1290-7. Epub Oct. 14, 2007.
Xenocostas, Anargyros et al., The pharmacokinetics of erythropoietin in the cerebrospinal fluid after intravenous administration of recombinant human erythropoietin. European Journal of Clinical Pharmacology, 61(3): 189-195 (Mar. 2005).
Xue, et al. Intrastriatal administration of erythropoietin protects dopaminergic neurons and improves neurobehavioral outcome in a rat model of Parkinson's disease. Neuroscience. May 25, 2007;146(3):1245-58.
Yamashita, et al. Post-Occlusion Treatment with BDNF Reduces Infarct Size in a Model of Permanent Occlusion of the Middle Cerebral Artery in Rat. Metabolic Brain Disease 12 (4);1997:271-80.
Yan, et al. 1994. Distribution of Intracerebral Ventricularly Administered Neurotrophins in Rat Brain and Its Correlation with Trk Receptor Expression. Experimental Neurology 127: 23-36.
Yan, et al. 2007 Enduring vulnerability to reinstatement of methamphetamine-seeking behavior in glial-cell-line-derived neurotrophic factor mutant mice. FASEB J. Jul;21(9):1994-2004.
Yip, et al. Three-dimensional structural interactions of insulin and its receptor. J Biol Chem. Jul. 25, 2003;278(30):27329-32.
Zhang, et al. 2001. Conjugation of brain-derived neurotrophic factor to a blood-brain barrier drug targeting system enables neuroprotection in regional brain ischemia following intrvenous injection of the neurotrophin. Brain Research 889: 49-56.
Zhang, et al. 2001. Neuroprotection in Transient Focal Brain Ischemia After Delayed Intravenous Administration of Brain-Derived Neurotrophic Factor Conjugated to a Blood-Brain Barrier Drug Targeting System. Stroke 32: 1378-84.
Zhang, et al. 2001. Rapid transferrin efflux from brain to blood across the blood-brain barrier. J Neurochem. Mar;76(5):1597-600.
Zhang, et al. 2003. Global Non-Viral Gene Transfer to the Primate Brain Following Intravenous Administration. Molecular Therapy 7 (1): 11-18.
Zhang, et al. Mediated efflux of IgG molecules from brain to blood across the blood-brain barrier. J Neuroimmunol. Mar. 1, 2001;114(1-2):168-72.
Zhou, et al. Brain penetrating IgG-erythropoietin fusion protein is neuroprotective following intravenous treatment in Parkinson's disease in the mouse. Brain Res. Mar. 25, 2011;1382:315-20. Epub Jan. 26, 2011.
Zhou; et al., "Neuroprotection with a brain-penetrating biologic tumor necrosis factor inhibitor.", J Pharmacol Exp Ther, Nov. 2011, 339(2), 618-23.
Zhou, et all. Brain-penetrating IgG-iduronate 2-sulfatase fusion protein for the mouse. Drug Metab Dispos. Feb. 2012;40(2):329-35. doi: 10.1124/dmd.111.042903. Epub Nov. 7, 2011.
Zito, et al. Sulphatase activities are regulated by the interaction of sulphatase-modifying factor 1 with SUMF2, EMBO Rep 2005;6(7):655-660.

(56) References Cited

OTHER PUBLICATIONS

Boado, R.J. A new generation of neurobiological drugs engineered to overcome the challenges of brain drug delivery. Drug News Perspect, 21(9):489-503 (Nov. 2008).
De Herder, Wouter W. et al. New therapeutic options for metastatic malignant insulinomas. Clinical Endocrinology (2011) 75; 277-284.
No Author. Precose Official FDA Information, side effects and uses. (Jan. 2008) pp. 1-12.
U.S. Appl. No. 14/538,721 Notice of Allowance dated Jan. 23, 2018.
Accusation by Medical Board of California dated Nov. 24, 2014 against Edward Tobinick before the Medical Board of California. Case No. 04/2012-224707.
Boado et al. IgG-enzyme fusion protein: pharmacokinetics and anti-drug antibody response in rhesus monkeys. Bioconjug Chem. 24(1):97-104 (2013).
Chen et al. Enhancement and destruction of antibody function U by somatic mutation: unequal occurrence is controlled by V gene combinatorial associations. The EMBO Journal 14(12):2784-2794 (1995).
Edwards et al. The remarkable flexibility of the human antibody repertoire; isolation of over one thousand different antibodies to a single protein. BLyS.J Mol Biol. 334(1):103-18 (2003).
European Patent Application No. 19150184 Extended European Search Report dated Dec. 13, 2019.
Genbank. anti-human CD40 12B4 chimeric kappa chain [synthetic construct]. ALO70203.1.
Japanese Patent Application No. 2018-089998 Office Action dated Dec. 10, 2019.
Kussie, et al. A single engineered amino acid substitution changes antibody fine specificity. J Immunol. Jan. 1, 1994;152(1):146-52.
Mahler et al. Induction and analysis of aggregates in a liquid IgG1-antibody formulation. Eur J Pharm Biopharm 59(3):407-17 (2005).
Office action dated Jan. 10, 2019 for U.S. Appl. No. 14/144,460.
Pagel et al., Comparison of a tetravalent single-chain antibody-streptavidin fusion protein and an antibody-streptavidin chemical conjugate for pretargeted anti-CD20 radioimmunotherapy of B-cell lymphomas. Blood. 108(1): 328-336 (2006).
PCT/US19/45547 International Search Report and Written Opinion dated Jan. 22, 2020.
PCT/US2019/045547 Invitation to Pay Additional Fees dated Oct. 29, 2019.
Sonoda et al. A Blood-Brain-Barrier-Penetrating Anti-human Transferrin Receptor Antibody Fusion Protein for Neuronopathic Mucopolysaccharidosis II. Mol Ther 26(5):1366-1374 (2018).
UniProtKB/Swiss-Prot: P22304. Iduronate 2-sulfatase precursor (Alpha-L-iduronate sulfate sulfatase) (Idursulfase) [Contains: Iduronate 2-sulfatase 42 kDa chain; Iduronate 2-sulfatase 14 kDa chain] (2007)/.
U.S. Appl. No. 14/594,047 Final Office Action dated Sep. 5, 2019.
U.S. Appl. No. 14/906,259 Non-final Office Action dated Mar. 18, 2019.
U.S. Appl. No. 15/357,894 Final Office Action dated Mar. 29, 2019.
U.S. Appl. No. 14/144,460 Final Office Action dated Sep. 30, 2019.
U.S. Appl. No. 14/281,803 Final Office Action dated Dec. 23, 2019.
U.S. Appl. No. 15/357,894 Non-Final Office Action dated Feb. 13, 2020.
U.S. Appl. No. 14/281,803 Office Action dated May 22, 2019.
Antibody Structure, retrieved from https://wmv.bioatla.com/appendix/antibody-strucutre/ (2020).
Bhagavan et al., Chapter 4—Three Dimensional Structure of Proteins and Disorders of Protein Misfolding. Essentials of Biochemistry (Second Edition). Excerpt section: Covalent and Coordinate Covalent Bonds in Protein Structure: first paragraph. (2015).
Boado et al., Bi-functional IgG-lysosomal enzyme fusion proteins for brain drug delivery. Scientific Reports 9: 18632 (2019).
Boado et al., Comparison of Blood-Brain Barrier Transport of Glial-Derived Neurotrophic Factor (GDNF) and an IgG-GDNF Fusion Protein in the Rhesus Monkey. Drug Metab Dispos 37(12): 2299-2304 (2009).
Condori et al., Enzyme replacement for GM1-gangliosidosis: Uptake, lysosomal activation, and cellular disease correction using a novel β-galactosidase:RTB lectin fusion. Mol Genet Metab. 117(2):199-209 (2016).
Dinatale et al., Heparan N-sulfatase: in vitro mutagenesis of potential N-glycosylation sites. Biochem Biophys Res Commun 280(5):1251-1257 (2001).
Fraldi et al., SUMF1 enhances sulfatase activities in vivo in five sulfatase deficiencies. Biochem J. 403(Pt 2): 305-312 (2007).
Gliddon et al., Purification and characterization of recombinant murine sulfamidase. Mol Genet Metab 83(3):239-245 (2004).
Hemsley et al., Examination of intravenous and intra-CSF protein delivery for treatment of neurological disease. Eur J Neurosci 29(6):1197-1214 (2009).
Jolly et al., Intracisternal enzyme replacement therapy in lysosomal storage diseases: routes of absorption into brain. Neuropathol Appl Neurobiol. 37(4):414-422 (2011).
Karpova et al., A fluorimetric enzyme assay for the diagnosis of Sanfilippo disease type A (MPS IIIA). J Inherit Metab Dis 19(3):278-285 (1996).
Marsh et al., 4-Methylumbelliferyl alpha-N-acetylglucosaminidase activity for diagnosis of Sanfilippo B disease. Clin Genet 27(3): 258-262 (1985).
Montfort et al., Expression and functional characterization of human mutant sulfamidase in insect cells. Mol Genet Metab 83(3):246-251 (2004).
PCT/US2020/012549 International Search Report and Written Opinion dated Apr. 21, 2020.
Scott et al. Cloning of the sulphamidase gene and identification of mutations in Sanfilippo A syndrome. Nat. Genet. 11:465-467 (1995).
Urayama et al., Mannose 6-phosphate receptor-mediated transport of sulfamidase across the blood-brain barrier in the newborn mouse. Mol Ther 16(7):1261-1266 (2008).
U.S. Appl. No. 14/594,047 Non-Final Office Action dated Apr. 30, 2020.
U.S. Appl. No. 16/264,343 Non-Final Office Action dated Jun. 5, 2020.
Valstar et al., Mucopolysaccharidosis type IIIA: clinical spectrum and genotype-phenotype correlations. Ann Neurol 68(6):876-887 (2010).
Weber et al. Cloning and expression of the gene involved in Sanfilippo B syndrome (mucopolysaccharidosis III B). Hum Mol Genet. 5:771-777 (1996).
Xue et al., LINKER: a web server to generate peptide sequences with extended conformation. Nucleic Acids Res. 32: W562-W565 (2004).
Zhao et al., The molecular basis of Sanfilippo syndrome type B. Proc Natl Acad Sci U S A 93(12):6101-6105 (1996).
U.S. Appl. No. 15/357,894 Final Office Action dated Dec. 21, 2020.
U.S. Appl. No. 16/828,557 Non-Final Office Action dated Nov. 6, 2020.

Figure 1

Amino Acid Sequence of HIR Ab HC (SEQ ID NO:7)

MDWTWRVFCLLAVAPGAHSQVQLQQSGPELVKPGALVKISCKASGYTFTNYDIHWVKQRP
GQGLEWIGWIYPGDGSTKYNEKFKGKATLTADKSSSTAYMHLSSLTSEKSAVYFCAREWA
YWGQGTLVTVSAASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFF
LYSKLTVDKSRWQQGNVFSCSVMHEALHNHYTQKSLSLSPGS

Figure 2

Amino Acid Sequence of HIR Ab LC (SEQ ID NO:8)

METPAQLLFLLLLWLPDTTGDIQMTQSPSSLSASLGERVSLTCRASQDIGGNLYWLQQGP
DGTIKRLIYATSSLDSGVPKRFSGSRSGSDYSLTISSLESEDFVDYYCLQYSSSPWTFGG
GTKMEIKR*TVAAPSVFIFPPSDEQLKSGTASVVCLLNNFYPREAKVQWKVDNALQSGNSQ*
*ESVTEQDSKDSTYSLSSTLTLSKADYEKHKVYACEVTHQGLSSPVTKSFNRGEC*

Figure 3

| HIR Ab HC CDRs | | |
|---|---|---|
| CDR1 | GYTFTNYDIH | SEQ ID NO:1 |
| CDR2 | WIYPGDGSTKYNEKFKG | SEQ ID NO:2 |
| CDR3 | EWAY | SEQ ID NO:3 |
| HIR Ab LC CDRs | | |
| CDR1 | RASQDIGGNLY | SEQ ID NO:4 |
| CDR2 | ATSSLDS | SEQ ID NO:5 |
| CDR3 | LQYSSSPWT | SEQ ID NO:6 |

Figure 4

Amino Acid Sequence of IDS (minus signal peptide)
(SEQ ID NO:9)

SETQANSTTDALNVLLIIVDDLRPSLGCYGDKLVRSPNIDQLASHSLLFQNAFAQQAVCAPSRVS
FLTGRRPDTTRLYDFNSYWRVHAGNFSTIPQYFKENGYVTMSVGKVFHPGISSNHTDDSPYSWSF
PPYHPSSEKYENTKTCRGPDGELHANLLCPVDVLDVPEGTLPDKQSTEQAIQLLEKMKTSASPFF
LAVGYHKPHIPFRYPKEFQKLYPLENITLAPDPEVPDGLPPVAYNPWMDIRQREDVQALNISVPY
GPIPVDFQRKIRQSYFASVSYLDTQVGRLLSALDDLQLANSTIIAFTSDHGWALGEHGEWAKYSN
FDVATHVPLIFYVPGRTASLPEAGEKLFPYLDPFDSASQLMEPGRQSMDLVELVSLFPTLAGLAG
LQVPPRCPVPSFHVELCREGKNLLKHFRFRDLEEDPYLPGNPRELIAYSQYPRPSDIPQWNSDKP
SLKDIKIMGYSIRTIDYRYTVWVGFNPDEFLANFSDIHAGELYFVDSDPLQDHNMYNDSQGGDLF
QLLMP

Figure 5

Amino Acid Sequence of HIR Ab-IDS HC (SEQ ID NO:10)

MDWTWRVFCLLAVAPGAHSQVQLQQSGPELVKPGALVKISCKASGYTFTNYDIHWVKQRPGQGLE
WIGWIYPGDGSTKYNEKFKGKATLTADKSSSTAYMHLSSLTSEKSAVYFCAREWAYWGQGTLVTV
SAASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKS
LSLSPGSSSETQANSTTDALNVLLIIVDDLRPSLGCYGDKLVRSPNIDQLASHSLLFQNAFAQQ
AVCAPSRVSFLTGRRPDTTRLYDFNSYWRVHAGNFSTIPQYFKENGYVTMSVGKVFHPGISSNHT
DDSPYSWSFPPYHPSSEKYENTKTCRGPDGELHANLLCPVDVLDVPEGTLPDKQSTEQAIQLLEK
MKTSASPFFLAVGYHKPHIPFRYPKEFQKLYPLENITLAPDPEVPDGLPPVAYNPWMDIRQREDV
QALNISVPYGPIPVDFQRKIRQSYFASVSYLDTQVGRLLSALDDLQLANSTIIAFTSDHGWALGE
HGEWAKYSNFDVATHVPLIFYVPGRTASLPEAGEKLFPYLDPFDSASQLMEPGRQSMDLVELVSL
FPTLAGLAGLQVPPRCPVPSFHVELCREGKNLLKHFRFRDLEEDPYLPGNPRELIAYSQYPRPSD
IPQWNSDKPSLKDIKIMGYSIRTIDYRYTVWVGFNPDEFLANFSDIHAGELYFVDSDPLQDHNMY
NDSQGGDLFQLLMP

Figure 16

Nucleotide Sequence of HIR Ab-IDS LC (SEQ ID NO:13)

GCCGCCACCATGGAGACCCCCGCCCAGCTGCTGTTCCTGTTGCTGCTTTGGCTTCCAGATACTACCGGCG
ACATCCAGATGACCCAGTCTCCATCCTCCTTATCTGCCTCTCTGGGAGAAAGAGTCAGTCTCACTTGTCG
GGCAAGTCAGGACATTGGTGGTAACTTATACTGGCTTCAGCAGGGACCAGATGGAACTATTAAACGCCTG
ATCTACGCCACATCCAGTTTAGATTCTGGTGTCCCCAAAAGGTTCAGTGGCAGTAGGTCTGGGTCAGATT
ATTCTCTCACCATCAGCAGCCTTGAGTCTGAAGATTTTGTAGACTATTACTGTCTACAGTATTCTAGTTC
TCCGTGGACGTTCGGTGGAGGCACAAAGCTGGAAATAAAACGAACTGTGGCTGCACCATCTGTCTTCATC
TTCCCGCCATCTGATGAGCAGTTGAAATCTGGAACTGCCTCTGTTGTGTGCCTGCTGAATAACTTCTATC
CCAGAGAGGCCAAAGTACAGTGGAAGGTGGATAACGCCCTCCAATCGGGTAACTCCCAGGAGAGTGTCAC
AGAGCAGGACAGCAAGGACAGCACCTACAGCCTCAGCAGCACCCTGACGCTGAGCAAAGCAGACTACGAG
AAACACAAAGTCTACGCCTGCGAAGTCACCCATCAGGGCCTGAGCTCGCCCGTCACAAAGAGCTTCAACA
GGGGAGAGTGTTAG

Figure 17

Nucleotide Sequence of HIR Ab-IDS HC (SEQ ID NO:14)

```
GCCGCCACCATGGACTGGACCTGGAGGGTGTTCTGCCTGCTTGCAGTGGCCCCCGGAGCCCACAGCCAGG
TTCAGCTGCAGCAGTCTGGACCTGAGCTGGTGAAGCCTGGGGCTTTAGTGAAGATATCCTGCAAGGCTTC
TGGTTACACCTTCACAAACTACGATATACACTGGGTGAAGCAGAGGCCTGGACAGGGACTTGAGTGGATT
GGATGGATTTATCCTGGAGATGGTAGTACTAAGTACAATGAGAAATTCAAGGGCAAGGCCACACTGACTG
CAGACAAATCCTCCAGCACAGCCTACATGCACCTCAGCAGCCTGACTTCTGAGAAATCTGCAGTCTATTT
CTGTGCAAGAGAGTGGGCTTACTGGGGCCAAGGGACTCTGGTCACTGTCTCTGCAGCTAGCACCAAGGGC
CCATCGGTCTTCCCCCTGGCACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGTGGACAAGAAAGTTG
AGCCCAAATCTTGTGACAAAACTCACACATGCCCACCGTGCCCAGCACCTGAACTCCTGGGGGGACCGTC
AGTCTTCCTCTTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACCGTCCT
GCACCAGGACTGGCTGAATGGCAAGGAGTACAAGTGCAAGGTCTCCAACAAAGCCCTCCCAGCCCCCATC
GAGAAAACCATCTCCAAAGCCAAAGGGCAGCCCCGAGAACCACAGGTGTACACCCTGCCCCCATCCCGGG
ATGAGCTGACCAAGAACCAGGTCAGCCTGACCTGCCTGGTCAAAGGCTTCTATCCCAGCGACATCGCCGT
GGAGTGGGAGAGCAATGGGCAGCCGGAGAACAACTACAAGACCACGCCTCCCGTGCTGGACTCCGACGGC
TCCTTCTTCCTCTACAGCAAGCTCACCGTGGACAAGAGCAGGTGGCAGCAGGGGAACGTCTTCTCATGCT
CCGTGATGCATGAGGCTCTGCACAACCACTACACGCAGAAGAGCCTCTCCCTGTCTCCtGGTAGTAGTTC
CTCCGAAACGCAGGCCAACTCGACCACAGATGCTCTGAACGTTCTTCTCATCATCGTGGATGACCTGCGC
CCCTCCCTGGGCTGTTATGGGGATAAGCTGGTGAGGTCCCCAAATATTGACCAACTGGCATCCCACAGCC
TCCTCTTCCAGAATGCCTTTGCGCAGCAAGCAGTGTGCGCCCCGAGCCGCGTTTCTTTCCTCACTGGCAG
GAGACCTGACACCACCCGCCTGTACGACTTCAACTCCTACTGGAGGGTGCACGCTGGAAACTTCTCCACC
ATCCCCCAGTACTTCAAGGAGAATGGCTATGTGACCATGTCGGTGGGAAAAGTCTTTCACCCTGGGATAT
CTTCTAACCATACTGATGATTCTCCGTATAGCTGGTCTTTTCCACCTTATCATCCTTCCTCTGAGAAGTA
TGAAAACACTAAGACATGTCGAGGGCCAGATGGAGAACTCCATGCCAACCTGCTTTGCCCTGTGGATGTG
CTGGATGTTCCCGAGGGCACCTTGCCTGACAAACAGAGCACTGAGCAAGCCATACAGTTGTTGGAAAAGA
TGAAAACGTCAGCCAGTCCTTTCTTCCTGGCCGTTGGGTATCATAAGCCACACATCCCCTTCAGATACCC
CAAGGAATTTCAGAAGTTGTATCCCTTGGAGAACATCACCCTGGCCCCCGATCCCGAGGTCCCTGATGGC
CTACCCCCTGTGGCCTACAACCCCTGGATGGACATCAGGCAACGGGAAGACGTCCAAGCCTTAAACATCA
GTGTGCCGTATGGTCCAATTCCTGTGGACTTTCAGCGGAAAATCCGCCAGAGCTACTTTGCCTCTGTGTC
ATATTTGGATACACAGGTCGGCCGCCTCTTGAGTGCTTTGGACGATCTTCAGCTGGCCAACAGCACCATC
ATTGCATTTACCTCGGATCATGGGTGGGCTCTAGGTGAACATGGAGAATGGGCCAAATACAGCAATTTTG
ATGTTGCTACCCATGTTCCCCTGATATTCTATGTTCCTGGAAGGACGGCTTCACTTCCGGAGGCAGGCGA
GAAGCTTTTCCCTTACCTCGACCCTTTTGATTCCGCCTCACAGTTGATGGAGCCAGGCAGGCAATCCATG
GACCTTGTGGAACTTGTGTCTCTTTTTCCCACGCTGGCTGGACTTGCAGGACTGCAGGTTCCACCTCGCT
GCCCCGTTCCTTCATTTCACGTTGAGCTGTGCAGAGAAGGCAAGAACCTTCTGAAGCATTTTCGATTCCG
TGACTTGGAAGAGGATCCGTACCTCCCTGGTAATCCCCGTGAACTGATTGCCTATAGCCAGTATCCCCGG
CCTTCAGACATCCCTCAGTGGAATTCTGACAAGCCGAGTTTAAAAGATATAAAGATCATGGGCTATTCCA
TACGCACCATAGACTATAGGTATACTGTGTGGGTTGGCTTCAATCCTGATGAATTTCTAGCTAACTTTTC
TGACATCCATGCAGGGGAACTGTATTTTGTGGATTCTGACCCATTGCAGGATCACAATATGTATAATGAT
TCCCAAGGTGGAGATCTTTTCCAGTTGTTGATGCCTTGA
```

Figure 18

Nucleotide Sequence of HIR Ab-IDS DHFR (SEQ ID NO:15)

GCCGCCACCATGGTTCGACCATTGAACTGCATCGTCGCCGTGTCCCAAAATATGGGGATTGGCAAGAACG
GAGACCTACCCTGGCCTCCGCTCAGGAACGAGTTCAAGTACTTCCAAAGAATGACCACAACCTCTTCAGT
GGAAGGTAAACAGAATCTGGTGATTATGGGTAGGAAAACCTGGTTCTCCATTCCTGAGAAGAATCGACCT
TTAAAGGACAGAATTAATATAGTTCTCAGTAGAGAACTCAAAGAACCACCACGAGGAGCTCATTTTCTTG
CCAAAAGTTTGGATGATGCCTTAAGACTTATTGAACAACCGGAATTGGCAAGTAAAGTAGACATGGTTTG
GATAGTCGGAGGCAGTTCTGTTTACCAGGAAGCCATGAATCAACCAGGCCACCTCAGACTCTTTGTGACA
AGGATCATGCAGGAATTTGAAAGTGACACGTTTTTCCCAGAAATTGATTTGGGGAAATATAAACTTCTCC
CAGAATACCCAGGCGTCCTCTCTGAGGTCCAGGAGGAAAAAGGCATCAAGTATAAGTTTGAAGTCTACGA
GAAGAAAGACTAA

Figure 19

Amino Acid Sequence of HIR Ab-IDS LC (SEQ ID NO:16)

METPAQLLFLLLLWLPDTTGDIQMTQSPSSLSASLGERVSLTCRASQDIGGNLYWLQQGPDGTIKRLIYA
TSSLDSGVPKRFSGSRSGSDYSLTISSLESEDFVDYYCLQYSSSPWTFGGGTKMEIKRTVAAPSVFIFPP
SDEQLKSGTASVVCLLNNFYPREAKVQWKVDNALQSGNSQESVTEQDSKDSTYSLSSTLTLSKADYEKHK
VYACEVTHQGLSSPVTKSFNRGEC

Figure 20

Amino Acid Sequence of HIR Ab-IDS DFHR (SEQ ID NO:17)

MVRPLNCIVAVSQNMGIGKNGDLPWPPLRNEFKYFQRMTTTSSVEGKQNLVIMGRKTWFSIPEKNRPLKD
RINIVLSRELKEPPRGAHFLAKSLDDALRLIEQPELASKVDMVWIVGGSSVYQEAMNQPGHLRLFVTRIM
QEFESDTFFPEIDLGKYKLLPEYPGVLSEVQEEKGIKYKFEVYEKKD

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Thr Phe Thr Asn Tyr Asp Ile His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ile Tyr Pro Gly Asp Gly Ser Thr Lys Tyr Asn Glu Lys Phe Lys
1               5                   10                  15

Gly

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Glu Trp Ala Tyr
1

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Asp Ile Gly Gly Asn Leu Tyr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Thr Ser Ser Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Gln Tyr Ser Ser Ser Pro Trp Thr
1               5

<210> SEQ ID NO 7
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110
```

Tyr Phe Cys Ala Arg Glu Trp Ala Tyr Trp Gly Gln Gly Thr Leu Val
            115                 120                 125

Thr Val Ser Ala Ala Ser Thr Lys Gly Pro Ser Val Phe Pro Leu Ala
130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
            165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Ser
    450                 455                 460

<210> SEQ ID NO 8
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Glu Thr Pro Ala Gln Leu Leu Phe Leu Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Gly Thr Lys Met Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 9
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110
```

```
His Pro Gly Ile Ser Ser Asn His Thr Asp Asp Ser Pro Tyr Ser Trp
            115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525
```

-continued

```
<210> SEQ ID NO 10
<211> LENGTH: 989
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Asp Trp Thr Trp Arg Val Phe Cys Leu Leu Ala Val Ala Pro Gly
1               5                   10                  15

Ala His Ser Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Lys Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365
```

```
Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Ser Ser Ser
    450                 455                 460

Ser Glu Thr Gln Ala Asn Ser Thr Thr Asp Ala Leu Asn Val Leu Leu
465                 470                 475                 480

Ile Ile Val Asp Asp Leu Arg Pro Ser Leu Gly Cys Tyr Gly Asp Lys
                485                 490                 495

Leu Val Arg Ser Pro Asn Ile Asp Gln Leu Ala Ser His Ser Leu Leu
            500                 505                 510

Phe Gln Asn Ala Phe Ala Gln Gln Ala Val Cys Ala Pro Ser Arg Val
        515                 520                 525

Ser Phe Leu Thr Gly Arg Arg Pro Asp Thr Thr Arg Leu Tyr Asp Phe
    530                 535                 540

Asn Ser Tyr Trp Arg Val His Ala Gly Asn Phe Ser Thr Ile Pro Gln
545                 550                 555                 560

Tyr Phe Lys Glu Asn Gly Tyr Val Thr Met Ser Val Gly Lys Val Phe
                565                 570                 575

His Pro Gly Ile Ser Ser Asn His Thr Asp Asp Ser Pro Tyr Ser Trp
            580                 585                 590

Ser Phe Pro Pro Tyr His Pro Ser Ser Glu Lys Tyr Glu Asn Thr Lys
        595                 600                 605

Thr Cys Arg Gly Pro Asp Gly Glu Leu His Ala Asn Leu Leu Cys Pro
    610                 615                 620

Val Asp Val Leu Asp Val Pro Glu Gly Thr Leu Pro Asp Lys Gln Ser
625                 630                 635                 640

Thr Glu Gln Ala Ile Gln Leu Leu Glu Lys Met Lys Thr Ser Ala Ser
                645                 650                 655

Pro Phe Phe Leu Ala Val Gly Tyr His Lys Pro His Ile Pro Phe Arg
            660                 665                 670

Tyr Pro Lys Glu Phe Gln Lys Leu Tyr Pro Leu Glu Asn Ile Thr Leu
        675                 680                 685

Ala Pro Asp Pro Glu Val Pro Asp Gly Leu Pro Pro Val Ala Tyr Asn
    690                 695                 700

Pro Trp Met Asp Ile Arg Gln Arg Glu Asp Val Gln Ala Leu Asn Ile
705                 710                 715                 720

Ser Val Pro Tyr Gly Pro Ile Pro Val Asp Phe Gln Arg Lys Ile Arg
                725                 730                 735

Gln Ser Tyr Phe Ala Ser Val Ser Tyr Leu Asp Thr Gln Val Gly Arg
            740                 745                 750

Leu Leu Ser Ala Leu Asp Asp Leu Gln Leu Ala Asn Ser Thr Ile Ile
        755                 760                 765

Ala Phe Thr Ser Asp His Gly Trp Ala Leu Gly Glu His Gly Glu Trp
    770                 775                 780
```

```
Ala Lys Tyr Ser Asn Phe Asp Val Ala Thr His Val Pro Leu Ile Phe
785                 790                 795                 800

Tyr Val Pro Gly Arg Thr Ala Ser Leu Pro Glu Ala Gly Glu Lys Leu
            805                 810                 815

Phe Pro Tyr Leu Asp Pro Phe Asp Ser Ala Ser Gln Leu Met Glu Pro
        820                 825                 830

Gly Arg Gln Ser Met Asp Leu Val Glu Leu Val Ser Leu Phe Pro Thr
            835                 840                 845

Leu Ala Gly Leu Ala Gly Leu Gln Val Pro Pro Arg Cys Pro Val Pro
850                 855                 860

Ser Phe His Val Glu Leu Cys Arg Glu Gly Lys Asn Leu Leu Lys His
865                 870                 875                 880

Phe Arg Phe Arg Asp Leu Glu Glu Asp Pro Tyr Leu Pro Gly Asn Pro
                885                 890                 895

Arg Glu Leu Ile Ala Tyr Ser Gln Tyr Pro Arg Pro Ser Asp Ile Pro
            900                 905                 910

Gln Trp Asn Ser Asp Lys Pro Ser Leu Lys Asp Ile Lys Ile Met Gly
        915                 920                 925

Tyr Ser Ile Arg Thr Ile Asp Tyr Arg Tyr Thr Val Trp Val Gly Phe
930                 935                 940

Asn Pro Asp Glu Phe Leu Ala Asn Phe Ser Asp Ile His Ala Gly Glu
945                 950                 955                 960

Leu Tyr Phe Val Asp Ser Asp Pro Leu Gln Asp His Asn Met Tyr Asn
                965                 970                 975

Asp Ser Gln Gly Gly Asp Leu Phe Gln Leu Leu Met Pro
            980                 985

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctccgaaac gcaggccaac tcg                                           23

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcaaggcatc aacaactgga aaagatc                                       27

<210> SEQ ID NO 13
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gccgccacca tggagacccc cgcccagctg ctgttcctgt tgctgctttg gcttccagat      60
actaccggcg acatccagat gacccagtct ccatcctcct tatctgcctc tctgggagaa    120
```

```
agagtcagtc tcacttgtcg ggcaagtcag gacattggtg gtaacttata ctggcttcag    180
cagggaccag atggaactat taaacgcctg atctacgcca catccagttt agattctggt    240
gtccccaaaa ggttcagtgg cagtaggtct gggtcagatt attctctcac catcagcagc    300
cttgagtctg aagattttgt agactattac tgtctacagt attctagttc ccgtggacg    360 ttcggtggag gcacaaagct ggaaataaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttag          714
```

<210> SEQ ID NO 14
<211> LENGTH: 2979
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 14

```
gccgccacca tggactggac ctggagggtg ttctgcctgc ttgcagtggc ccccggagcc     60
cacagccagg ttcagctgca gcagtctgga cctgagctgt gaagcctggg gctttagtg    120 aagatatcct gcaaggcttc tggttacacc ttcacaaact acgatataca ctgggtgaag    180
cagaggcctg gacagggact tgagtggatt ggatggattt atcctggaga tggtagtact    240
aagtacaatg agaaattcaa gggcaaggcc acactgactg cagacaaatc ctccagcaca    300
gcctacatgc acctcagcag cctgacttct gagaaatctg cagtctattt ctgtgcaaga    360
gagtgggctt actggggcca agggactctg gtcactgtct ctgcagctag caccaagggc    420
ccatcggtct tccccctggc accctcctcc aagagcacct ctgggggcac agcggccctg    480
ggctgcctgg tcaaggacta cttccccgaa ccggtgacgg tgtcgtggaa ctcaggcgcc    540
ctgaccagcg gcgtgcacac cttcccggct gtcctacagt cctcaggact ctactccctc    600
agcagcgtgg tgaccgtgcc ctccagcagc ttgggcaccc agacctacat ctgcaacgtg    660
aatcacaagc ccagcaacac caaggtggac aagaaagttg agcccaaatc ttgtgacaaa    720
actcacacat gcccaccgtg cccagcacct gaactcctgg ggggaccgtc agtcttcctc    780
ttccccccaa aacccaagga caccctcatg atctcccgga cccctgaggt cacatgcgtg    840
gtggtggacg tgagccacga agaccctgag gtcaagttca actggtacgt ggacggcgtg    900
gaggtgcata atgccaagac aaagccgcgg gaggagcagt acaacagcac gtaccgtgtg    960
gtcagcgtcc tcaccgtcct gcaccaggac tggctgaatg gcaaggagta caagtgcaag   1020
gtctccaaca aagccctccc agcccccatc gagaaaacca tctccaaagc caaagggcag   1080
ccccgagaac cacaggtgta caccctgccc ccatcccggg atgagctgac caagaaccag   1140
gtcagcctga cctgcctggt caaaggcttc tatcccagcg acatcgccgt ggagtgggag   1200
agcaatgggc agccggagaa caactacaag accacgcctc ccgtgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctcctg gtagtagttc ctccgaaacg caggccaact cgaccacaga tgctctgaac   1440
```

-continued

```
gttcttctca tcatcgtgga tgacctgcgc ccctccctgg gctgttatgg ggataagctg   1500
gtgaggtccc caaatattga ccaactggca tcccacagcc tcctcttcca gaatgccttt   1560
gcgcagcaag cagtgtgcgc cccgagccgc gtttctttcc tcactggcag gagacctgac   1620
accacccgcc tgtacgactt caactcctac tggagggtgc acgctggaaa cttctccacc   1680
atcccccagt acttcaagga gaatggctat gtgaccatgt cggtgggaaa agtctttcac   1740
cctgggatat cttctaacca tactgatgat ctccgtata gctggtcttt tccaccttat   1800
catccttcct ctgagaagta tgaaaacact aagacatgtc gagggccaga tggagaactc   1860
catgccaacc tgctttgccc tgtggatgtg ctggatgttc ccgagggcac cttgcctgac   1920
aaacagagca ctgagcaagc catacagttg ttggaaaaga tgaaaacgtc agccagtcct   1980
ttcttcctgg ccgttgggta tcataagcca cacatcccct tcagatacc caaggaattt   2040 cagaagttgt atcccttgga gaacatcacc ctggcccccg atcccgaggt ccctgatggc   2100
ctaccccctg tggcctacaa cccctggatg gacatcaggc aacgggaaga cgtccaagcc   2160
ttaaacatca gtgtgccgta tggtccaatt cctgtggact ttcagcggaa aatccgccag   2220
agctactttg cctctgtgtc atatttggat acacaggtcg gccgcctctt gagtgctttg   2280
gacgatcttc agctggccaa cagcaccatc attgcattta cctcggatca tgggtgggct   2340
ctaggtgaac atggagaatg ggccaaatac agcaattttg atgttgctac ccatgttccc   2400
ctgatattct atgttcctgg aaggacggct tcacttccgg aggcaggcga aagcttttc   2460 ccttacctcg accctttga ttccgcctca cagttgatgg agccaggcag gcaatccatg   2520
gaccttgtgg aacttgtgtc tctttttccc acgctggctg gacttgcagg actgcaggtt   2580
ccacctcgct gccccgttcc ttcatttcac gttgagctgt gcagagaagg caagaaccctt   2640 ctgaagcatt ttcgattccg tgacttggaa gaggatccgt acctccctgg taatcccgt   2700 gaactgattg cctatagcca gtatccccgg ccttcagaca tccctcagtg gaattctgac   2760
aagccgagtt taaagatat aaagatcatg ggctattcca tacgcaccat agactatagg   2820
tatactgtgt gggttggctt caatcctgat gaatttctag ctaactttc tgacatccat   2880 gcaggggaac tgtattttgt ggattctgac ccattgcagg atcacaatat gtataatgat   2940
tcccaaggtg gagatctttt ccagttgttg atgccttga                          2979
```

<210> SEQ ID NO 15
<211> LENGTH: 573
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
gccgccacca tggttcgacc attgaactgc atcgtcgccg tgtcccaaaa tatgggggatt     60 ggcaagaacg gagacctacc ctggcctccg ctcaggaacg agttcaagta cttccaaaga    120
atgaccacaa cctcttcagt ggaaggtaaa cagaatctgg tgattatggg taggaaaacc    180
tggttctcca ttcctgagaa gaatcgacct taaaggaca gaattaatat agttctcagt    240
agagaactca agaaccacc acgaggagct catttttcttg ccaaaagttt ggatgatgcc    300
ttaagactta ttgaacaacc ggaattggca agtaaagtag acatggtttg gatagtcgga    360
ggcagttctg tttaccagga agccatgaat caaccaggcc acctcagact ctttgtgaca    420
aggatcatgc aggaatttga agtgacacg ttttttcccag aaattgattt ggggaaatat    480
```

```
aaacttctcc cagaatacccc aggcgtcctc tctgaggtcc aggaggaaaa aggcatcaag    540
tataagtttg aagtctacga gaagaaagac taa                                  573
```

<210> SEQ ID NO 16
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Glu Thr Pro Ala Gln Leu Leu Phe Leu Leu Leu Trp Leu Pro
1               5                   10                  15

Asp Thr Thr Gly Asp Ile Gln Met Thr Gln Ser Pro Ser Ser Leu Ser
            20                  25                  30

Ala Ser Leu Gly Glu Arg Val Ser Leu Thr Cys Arg Ala Ser Gln Asp
        35                  40                  45

Ile Gly Gly Asn Leu Tyr Trp Leu Gln Gln Gly Pro Asp Gly Thr Ile
    50                  55                  60

Lys Arg Leu Ile Tyr Ala Thr Ser Ser Leu Asp Ser Gly Val Pro Lys
65                  70                  75                  80

Arg Phe Ser Gly Ser Arg Ser Gly Ser Asp Tyr Ser Leu Thr Ile Ser
                85                  90                  95

Ser Leu Glu Ser Glu Asp Phe Val Asp Tyr Tyr Cys Leu Gln Tyr Ser
            100                 105                 110

Ser Ser Pro Trp Thr Phe Gly Gly Gly Thr Lys Met Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 17
<211> LENGTH: 187
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Val Arg Pro Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Lys Tyr Phe Gln Arg Met Thr Thr Thr Ser Ser Val Glu Gly Lys Gln
        35                  40                  45
```

```
Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95

Ala Leu Arg Leu Ile Glu Gln Pro Glu Leu Ala Ser Lys Val Asp Met
                100                 105                 110

Val Trp Ile Val Gly Gly Ser Ser Val Tyr Gln Glu Ala Met Asn Gln
            115                 120                 125

Pro Gly His Leu Arg Leu Phe Val Thr Arg Ile Met Gln Glu Phe Glu
        130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp
                180                 185

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccacagatgc tctgaacgtt cttc                                              24

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser Gly Gly Gly Gly Ser Gly Gly Gly Gly Ser
1               5                   10                  15
```

METHODS AND COMPOSITIONS FOR INCREASING IDURONATE 2-SULFATASE ACTIVITY IN THE CNS

CROSS-REFERENCE TO RELATED APPLICATIONS

This application is a continuation of U.S. application Ser. No. 14/305,402 filed Jun. 16, 2014, which is a continuation of U.S. application Ser. No. 12/901,481 filed on Oct. 8, 2010, now U.S. Pat. No. 8,834,874 issued Sep. 16, 2014, which claims the benefit under 35 U.S.C. § 119(e) of U.S. Provisional Application No. 61/250,378, filed Oct. 9, 2009, and U.S. Provisional Application No. 61/256,049, filed Oct. 29, 2009, all of which are incorporated herein by reference in their entirety.

SEQUENCE LISTING

The Instant application contains a Sequence Listing which has been submitted electronically in ACSII format and is hereby incorporated by reference in its entirety. Said ASCII copy, created on Sep. 10, 2014 is named 28570-710.302_SL.txt and is 32,154 bytes in size.

BACKGROUND OF THE INVENTION

Type II mucopolysaccharidosis (MPS), also known as Hunter's syndrome, is an inherited metabolic disease caused by a defect in the enzyme iduronate 2-sulfatase (IDS), which functions to degrade mucopolysaccharides. An insufficient level of IDS causes a pathological buildup of heparan sulfate and dermatan sulfate in, e.g., the heart, liver, and central nervous system (CNS). Symptoms including neurodegeneration and mental retardation appear during childhood; and early death can occur due to organ damage in the brain. Typically, treatment includes intravenous enzyme replacement therapy with recombinant IDS. However, systemically administered recombinant IDS does not cross the blood brain barrier (BBB), and therefore has little impact on the effects of the disease in the CNS.

SUMMARY OF THE INVENTION

Described herein are methods and compositions for treating a subject suffering from an iduronate 2-sulfatase ("IDS") deficiency. The compositions provided herein comprise fusion antibodies comprising an IDS polypeptide fused to structure (e.g., antibody, immunoglobulin) capable of crossing the blood-brain barrier (BBB). In some embodiments, the structure that is capable of crossing the BBB crosses the BBB on an endogenous BBB receptor. In some embodiments, the endogenous BBB receptor is the insulin receptor, transferrin receptor, leptin receptor, lipoprotein receptor, and the IGF receptor. In some embodiments, the endogenous BBB receptor is the insulin receptor. In some embodiments, the methods allow delivery of IDS to the CNS by systemically administering a therapeutically effective amount of a bifunctional human insulin receptor antibody (e.g., HIR Ab)-IDS fusion antibody. In some embodiments, the HIR Ab-IDS fusion antibody binds to the extracellular domain of the insulin receptor and is transported across the blood brain barrier ("BBB") into the CNS, while retaining iduronate 2-sulfatase activity. In some embodiments, the HIR Ab binds to the endogenous insulin receptor on the BBB, and acts as a molecular Trojan horse to ferry the IDS into the brain. A therapeutically effective systemic dose of a HIR Ab-IDS fusion antibody for systemic administration is based, in part, on the specific CNS uptake characteristics of the fusion antibody from peripheral blood as described herein.

In some embodiments, the invention provides compositions containing an IDS covalently linked to a structure (e.g., immunoglobulin, antibody) that is capable of crossing the blood brain barrier (BBB), where the structure and the IDS each retains at least about 10, 20, 30, 40, 50, 60, 70, 80, 90, 95, 99, or 100% of its activity, compared to its activity as a separate entity. In some embodiments, the IDS retains at least about 10% of its activity compared to its activity as a separate entity. In some embodiments, the IDS retains at least 20% of its activity, compared to its activity as a separate entity. In some embodiments, the IDS retains at least 30% of its activity, compared to its activity as a separate entity. In some embodiments, the IDS retains at least 40% of its activity, compared to its activity as a separate entity. In some embodiments, the IDS retains at least 50% of its activity, compared to its activity as a separate entity. In some embodiments, the IDS retains at least 60% of its activity, compared to its activity as a separate entity.

In some embodiments, a fusion antibody comprising IDS is post-translationally modified by a sulfatase modifying factor type 1 (SUMF1). In some embodiments, the post-translational modification comprises a cysteine to formylglycine conversion. In some embodiments, a fusion antibody comprises a formylglycine residue.

In one aspect provided herein is a method for treating an IDS deficiency in the central nervous system of a subject in need thereof, comprising systemically administering to the subject a therapeutically effective dose of a fusion antibody having IDS activity. In some embodiments of this aspect: (i) the fusion antibody comprises the amino acid sequence of an immunoglobulin heavy chain, the amino acid sequence of an IDS, and the amino acid sequence of an immunoglobulin light chain; (ii) the fusion antibody binds to an extracellular domain of the human insulin receptor and catalyzes hydrolysis of the 2-sulfate groups of the L-iduronate 2-sulfate units of dermatan sulfate, heparan sulfate or heparin; and (iii) the amino acid sequence of the IDS is covalently linked to the carboxy terminus of the amino acid sequence of the immunoglobulin heavy chain. In some embodiments, the immunoglobulin heavy chain is an immunoglobulin heavy chain of IgG. In some embodiments, the immunoglobulin heavy chain is an immunoglobulin heavy chain of kappa class.

In some embodiments at least about 250,000 units of IDS activity are delivered to the brain, where 1 unit=1 nmol/hr using a fluorometric assay. In some embodiments, the therapeutically effective dose of the fusion antibody comprises at least about $2.5 \times 10^6$ units of IDS activity or at least about 50,000 units/Kg of body weight. In some embodiments the IDS specific activity of the fusion antibody is at least 30,000 units/mg. In some embodiments, systemic administration is parenteral, intravenous, subcutaneous, intra-muscular, trans-nasal, intra-arterial, transdermal, or respiratory. In some embodiments, at least about 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, 250,000 units of iduronate-2-sulfatase activity is delivered to the brain, normalized per 50 kg body weight. In some embodiments, at least about 25,000 units of iduronate-2-sulfatase activity is delivered to the brain, normalized per 50 kg body weight.

In some embodiments, the fusion antibody is a chimeric antibody.

In some embodiments, the immunoglobulin heavy chain of the fusion antibody comprises a CDR1 corresponding to the amino acid sequence of SEQ ID NO:1 with up to 4 single amino acid mutations, a CDR2 corresponding to the amino acid sequence of SEQ ID NO:2 with up to 6 single amino acid mutations, or a CDR3 corresponding to the amino acid sequence of SEQ ID NO:3 with up to 3 single amino acid mutations, wherein the single amino acid mutations are substitutions, deletions, or insertions.

In other embodiments, the immunoglobulin heavy chain of the fusion antibody comprises a CDR1 corresponding to the amino acid sequence of SEQ ID NO:1 with up to 3 single amino acid mutations, a CDR2 corresponding to the amino acid sequence of SEQ ID NO:2 with up to 6 single amino acid mutations, and a CDR3 corresponding to the amino acid sequence of SEQ ID NO:3 with up to 3 single amino acid mutations.

In other embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, or a CDR3 corresponding to the amino acid sequence of SEQ ID NO:3.

In further embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3.

In some embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, or a CDR3 corresponding to the amino acid sequence of SEQ ID NO:6 with up to 5 single amino acid mutations, wherein the single amino acid mutations are substitutions, deletions, or insertions.

In other embodiments, the immunoglobulin light chain of the fusion antibody comprises a CDR1 corresponding to the amino acid sequence of SEQ ID NO:4 with up to 3 single amino acid mutations, a CDR2 corresponding to the amino acid sequence of SEQ ID NO:5 with up to 5 single amino acid mutations, and a CDR3 corresponding to the amino acid sequence of SEQ ID NO:6 with up to 5 single amino acid mutations.

In other embodiments, the immunoglobulin light chain of the fusion antibody comprises a CDR1 corresponding to the amino acid sequence of SEQ ID NO:4, a CDR2 corresponding to the amino acid sequence of SEQ ID NO:5, or a CDR3 corresponding to the amino acid sequence of SEQ ID NO:6.

In further embodiments, the immunoglobulin light chain of the fusion antibody comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody comprises a CDR1 corresponding to the amino acid sequence of SEQ ID NO:1, a CDR2 corresponding to the amino acid sequence of SEQ ID NO:2, and a CDR3 corresponding to the amino acid sequence of SEQ ID NO:3; and the immunoglobulin light chain comprises a CDR1 corresponding to the amino acid sequence of SEQ ID NO:4, a CDR2 corresponding to the amino acid sequence of SEQ ID NO:5, and a CDR3 corresponding to the amino acid sequence of SEQ ID NO:6.

In some embodiments, the immunoglobulin heavy chain of the fusion antibody is at least 90% identical to SEQ ID NO:7 and the amino acid sequence of the light chain immunoglobulin is at least 90% identical to SEQ ID NO:8.

In some embodiments, the immunoglobulin heavy chain of the fusion antibody comprises SEQ ID NO:7 and the amino acid sequence of the light chain immunoglobulin comprises SEQ ID NO:8

In yet further embodiments, the IDS comprises an amino acid sequence at least 90% (e.g., 95%, or 100%) identical to SEQ ID NO:9.

In other embodiments, the amino acid sequence of the immunoglobulin heavy chain of the fusion antibody at least 90% identical to SEQ ID NO:7; the amino acid sequence of the light chain immunoglobulin is at least 90% identical to SEQ ID NO:8; and the amino acid sequence of the IDS is at least 95% identical to SEQ ID NO:9 or comprises SEQ ID NO:9.

In still other embodiments, the amino acid sequence of the immunoglobulin heavy chain of the fusion antibody comprises SEQ ID NO:8, the amino acid sequence of the immunoglobulin light chain comprises SEQ ID NO:8, and the amino acid sequence of the IDS comprises SEQ ID NO:9.

In some aspects, provided herein are pharmaceutical compositions comprising a therapeutically effective amount of a fusion antibody and a pharmaceutically acceptable excipient.

In some aspects, provided herein are isolated polynucleotides encoding a fusion antibody. In some embodiments, the isolated polynucleotide comprises the nucleic acid sequence of SEQ ID NO:14.

In some embodiments, provided herein are vectors comprising the isolated polynucleotides encoding a fusion antibody. In some embodiments, the vectors comprise the nucleic acid sequence of SEQ ID NO:14.

In some embodiments, provided herein are host cells comprising the vectors comprising the isolated polynucleotides encoding a fusion antibody. In some embodiments, the host cell is a Chinese Hamster Ovary (CHO).

In a further aspect provided herein is a method for treating an IDS deficiency in the central nervous system of a subject in need thereof, comprising systemically administering to the subject a therapeutically effective dose of a fusion antibody having IDS activity, wherein: (i) the fusion antibody comprises: (a) a fusion protein at least 95% identical to SEQ ID NO:10, and (b) an immunoglobulin light chain; and (ii) the fusion antibody binds to an extracellular domain of the human insulin receptor and catalyzes hydrolysis of linkages in dermatan or heparan sulfate.

In yet another aspect provided herein is a method for treating an IDS deficiency in the central nervous system of a subject in need thereof, comprising systemically administering to the subject a therapeutically effective dose of a fusion antibody having IDS activity, wherein:
(i) the fusion antibody comprises a fusion protein containing the amino acid sequence of an immunoglobulin heavy chain and an IDS or comprises a fusion protein containing the amino acid sequence of an immunoglobulin light chain and an IDS; the fusion antibody binds to the extracellular domain of the human insulin receptor; and the fusion antibody catalyzes hydrolysis of linkages in dermatan or heparan sulfate; and (ii) the amino acid sequence of the IDS is covalently linked to the carboxy terminus of the amino acid sequence of the immunoglobulin heavy chain or the immunoglobulin light chain.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, as follow:

FIG. 1. Amino acid sequence of an immunoglobulin heavy chain variable region from an exemplary human insulin receptor antibody directed against the extracellular domain of the human insulin receptor. The underlined sequences are a signal peptide, CDR1, CDR2, and CDR3, respectively. The heavy chain constant region, taken from human IgG1, is shown in italics.

FIG. 2. Amino acid sequence of an immunoglobulin light chain variable region from an exemplary human insulin receptor antibody directed against the extracellular domain of the human insulin receptor. The underlined sequences are a signal peptide, CDR1, CDR2, and CDR3, respectively. The constant region, derived from human kappa light chain, is shown in italics.

FIG. 3. A table showing the CDR1, CDR2, and CDR3 amino acid sequences from a heavy and light chain of an exemplary human insulin receptor antibody directed against the extracellular domain of the human insulin receptor.

FIG. 4. Amino acid sequence of human iduronate 2-sulfatase (IDS) (GenBank NP_000193), not including the initial 25 amino acid signal peptide (mature IDS).

FIG. 5. Amino acid sequence of a fusion of an exemplary human insulin receptor antibody heavy chain to mature human IDS. The underlined sequences are, in order, an IgG signal peptide, CDR1, CDR2, CDR3, and a peptide linker linking the carboxy terminus of the heavy chain to the amino terminus of the IDS. Sequence in italic corresponds to the heavy chain constant region, taken from human IgG1. The sequence in bold corresponds to human IDS.

FIG. 16. Nucleotide sequence of the immunoglobulin light chain (LC) region of an exemplary HIRMAb-IDS fusion antibody.

FIG. 17. Nucleotide sequence of the immunoglobulin heavy chain (HC) region of an exemplary HIRMAb-IDS fusion antibody.

FIG. 18. Nucleotide sequence of the DHFR region of an exemplary HIRMAb-IDS fusion antibody.

FIG. 19. Amino acid sequence of the immunoglobulin light chain (LC) region of an exemplary HIRMAb-IDS fusion antibody.

FIG. 20. Amino acid sequence of the DHFR region of an exemplary HIRMAb-IDS fusion antibody.

DETAILED DESCRIPTION OF THE INVENTION

Introduction

Figure 6:
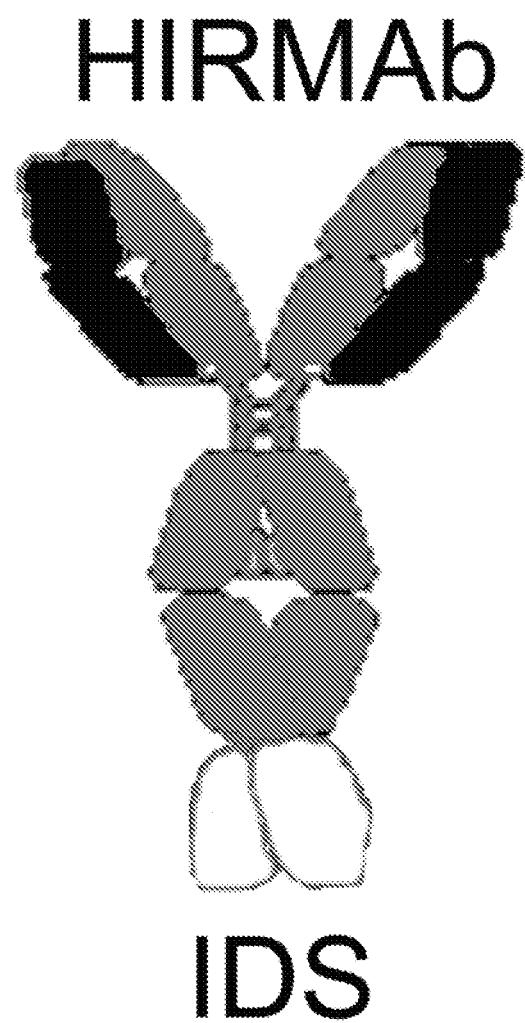
FIG. 6. An exemplary HIR Ab-IDS fusion antibody is formed by fusion of the amino terminus of the mature IDS to the carboxyl terminus of the CH3 region of the heavy chain of the HIR Ab FIG. 7. Schematic depiction of a "molecular trojan horse" strategy in which the fusion antibody comprises an antibody to the extracellular domain of the human insulin receptor (IR), which acts as a molecular Trojan horse (TH), and IDS, a lysosomal enzyme (E).

The blood brain barrier (BBB) is a severe impediment to the delivery of systemically administered IDS (e.g., recombinant IDS) to the central nervous system. The present disclosure provides methods and compositions for delivering therapeutically significant levels of IDS activity across the BBB to the CNS. In some embodiments, the IDS is modified to allow it to cross the BBB. In some embodiments, the amount and rate of uptake of systemically administered modified IDS into the CNS is provided. In some embodiments, the IDS retains a certain activity after being modified or after crossing the BBB. The present disclosure provides, inter alia: (1) IDS fusion antibodies comprising an IDS fused, with or without intervening sequence, to an immunoglobulin (heavy chain or light chain) capable of crossing the BBB, and related methods and compositions. (2) human insulin receptor (HIR) antibody (Ab)-IDS fusion antibodies comprising an IDS fused, with or without intervening sequence, to an immunoglobulin (heavy chain or light chain) directed against the extracellular domain of a human insulin receptor, and related methods and compositions; (3) methods of treating an IDS deficiency; and (4) methods of establishing therapeutically effective systemic doses of the fusion antibodies based on a characterization of their uptake in the CNS and their specific activity. In some embodiments, the invention provides compositions and methods for treating a nIDS deficiency in the central nervous system by systemically administering to a subject in need thereof a therapeutically effective dose of a bifunctional IDS fusion antibody (e.g., HIR Ab-IDS) having IDS activity and selectively binding to the receptor-mediated BBB transport system (e.g., the extracellular domain of a human insulin receptor).

Some Definitions

"Treatment" or "treating" as used herein includes achieving a therapeutic benefit and/or a prophylactic benefit. By therapeutic benefit is meant eradication or amelioration of the underlying disorder or condition being treated. For example, in an individual with Hunter's syndrome, therapeutic benefit includes partial or complete halting of the progression of the disorder, or partial or complete reversal of the disorder. Also, a therapeutic benefit is achieved with the eradication or amelioration of one or more of the physiological or psychological symptoms associated with the underlying condition such that an improvement is observed in the patient, notwithstanding the fact that the patient may still be affected by the condition. A prophylactic benefit of treatment includes prevention of a condition, retarding the progress of a condition (e.g., slowing the progression of a lysosomal storage disorder), or decreasing the likelihood of occurrence of a condition. As used herein, "treating" or "treatment" includes prophylaxis.

As used herein, the term "effective amount" can be an amount, which when administered systemically, is sufficient to effect beneficial or desired results in the CNS, such as beneficial or desired clinical results, or enhanced cognition, memory, mood, or other desired CNS results. An effective amount is also an amount that produces a prophylactic effect, e.g., an amount that delays, reduces, or eliminates the appearance of a pathological or undesired condition. Such conditions include, but are not limited to, mental retardation, hearing loss, and neurodegeneration. An effective amount can be administered in one or more administrations. In terms of treatment, an "effective amount" of a composition of the invention is an amount that is sufficient to palliate, ameliorate, stabilize, reverse or slow the progression of a disorder, e.g., a neurological disorder. An "effective amount" may be of any of the compositions of the invention used alone or in conjunction with one or more agents used to treat a disease or disorder. An "effective amount" of a therapeutic agent within the meaning of the present invention is determined by a patient's attending physician or veterinarian. Such amounts are readily ascertained by one of ordinary skill in the art and will a therapeutic effect when administered in accordance with the present invention. Factors which influence what a therapeutically effective amount will be include, the IDS specific activity of the IDS fusion antibody (e.g., HIR Ab-IDS) administered, its absorption profile (e.g., its rate of uptake into the brain), time elapsed since the initiation of the disorder, and the age, physical condition, existence of other disease states, and nutritional status of the individual being treated. Additionally, other medication the patient may be receiving will affect the determination of the therapeutically effective amount of the therapeutic agent to administer.

A "subject" or an "individual," as used herein, is an animal, for example, a mammal. In some embodiments a "subject" or an "individual" is a human. In some embodiments, the subject suffers from Mucopolysaccharidosis Type II ("Hunter's Syndrome").

In some embodiments, a pharmacological composition comprising an IDS fusion antibody (e.g., HIR Ab-IDS) fusion antibody is "administered peripherally" or "peripherally administered." As used herein, these terms refer to any form of administration of an agent, e.g., a therapeutic agent, to an individual that is not direct administration to the CNS, i.e., that brings the agent in contact with the non-brain side of the blood-brain barrier. "Peripheral administration," as used herein, includes intravenous, intra-arterial, subcutaneous, intramuscular, intraperitoneal, transdermal, by inhalation, transbuccal, intranasal, rectal, oral, parenteral, sublingual, or trans-nasal.

A "pharmaceutically acceptable carrier" or "pharmaceutically acceptable excipient" herein refers to any carrier that does not itself induce the production of antibodies harmful to the individual receiving the composition. Such carriers are well known to those of ordinary skill in the art. A thorough discussion of pharmaceutically acceptable carriers/excipients can be found in *Remington's Pharmaceutical Sciences*, Gennaro, A R, ed., 20th edition, 2000: Williams and Wilkins Pa., USA. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)).

The terms "isolated" and "purified" refer to a material that is substantially or essentially removed from or concentrated in its natural environment. For example, an isolated nucleic acid may be one that is separated from the nucleic acids that normally flank it or other nucleic acids or components (proteins, lipids, etc . . . ) in a sample. In another example, a polypeptide is purified if it is substantially removed from or concentrated in its natural environment. Methods for purification and isolation of nucleic acids and proteins are well known in the art.

The Blood Brain Barrier

In some embodiments, the invention provides compositions and methods that utilize an IDS fusion antibody (e.g., HIR Ab-IDS) capable of crossing the blood brain barrier (BBB). The compositions and methods are useful in transporting IDS from the peripheral blood and across the blood brain barrier into the CNS. As used herein, the "blood-brain barrier" refers to the barrier between the peripheral circulation and the brain and spinal cord which is formed by tight junctions within the brain capillary endothelial plasma membranes and creates an extremely tight barrier that restricts the transport of molecules into the brain; the BBB is so tight that it is capable of restricting even molecules as small as urea, molecular weight of 60 Da. The blood-brain barrier within the brain, the blood-spinal cord barrier within the spinal cord, and the blood-retinal barrier within the retina, are contiguous capillary barriers within the central nervous system (CNS), and are collectively referred to as the blood-brain barrier or BBB.

The BBB limits the development of new neurotherapeutics, diagnostics, and research tools for the brain and CNS. Most large molecule therapeutics such as recombinant proteins, antisense drugs, gene medicines, purified antibodies, or RNA interference (RNAi)-based drugs, do not cross the BBB in pharmacologically significant amounts. While it is generally assumed that small molecule drugs can cross the BBB, in fact, <2% of all small molecule drugs are active in the brain owing to the lack transport across the BBB. A molecule must be lipid soluble and have a molecular weight less than 400 Daltons (Da) in order to cross the BBB in pharmacologically significant amounts, and the vast majority of small molecules do not have these dual molecular characteristics. Therefore, most potentially therapeutic, diagnostic, or research molecules do not cross the BBB in pharmacologically active amounts. So as to bypass the BBB, invasive transcranial drug delivery strategies are used, such as intracerebro-ventricular (ICV) infusion, intracerebral (IC) administration, and convection enhanced diffusion (CED). Transcranial drug delivery to the brain is expensive, invasive, and largely ineffective. The ICV route delivers IDS only to the ependymal surface of the brain, not into brain parenchyma, which is typical for drugs given by the ICV route. The IC administration of an enzyme such as IDS, only provides local delivery, owing to the very low efficiency of protein diffusion within the brain. The CED results in preferential fluid flow through the white matter tracts of brain, which causes demyelination, and astrogliosis.

The methods described herein offer an alternative to these highly invasive and generally unsatisfactory methods for bypassing the BBB, allowing a functional IDS to cross the BBB from the peripheral blood into the CNS following systemic administration of an the IDS fusion antibody (e.g., HIR Ab-IDS) fusion antibody composition described herein. The methods described herein exploit the expression of insulin receptors (e.g., human insulin receptors) or other receptor on the BBB to shuttle a desired bifunctional IDS fusion antibody (e.g., HIR Ab-IDS) from peripheral blood into the CNS.

Endogenous BBB Receptor-Mediated Transport Systems

The BBB has been shown to have specific receptors that allow the transport from the blood to the brain of several macromolecules; these transporters are suitable as transporters for compositions of the invention. Endogenous BBB receptor-mediated transport systems useful in the invention include those that transport insulin, transferrin, insulin-like growth factors 1 and 2 (IGF1 and IGF2), leptin, and lipoproteins. In some embodiments, the invention utilizes a structure (e.g., immunoglobulin, antibody) that is capable of crossing the BBB via the endogenous insulin BBB receptor-mediated transport system, e.g., the human endogenous insulin BBB receptor-mediated transport system. In some embodiments, the structure (e.g., immunoglobulin, antibody) that is capable of crossing the BBB, crosses the BBB by binding a receptor for one or more of the following:

insulin, transferrin, insulin-like growth factors 1 and 2 (IGF1 and IGF2), leptin, and/or lipoproteins.

The BBB has been shown to have specific receptors, including insulin receptors, that allow the transport from the blood to the brain of several macromolecules. In particular, insulin receptors are suitable as transporters for the IDS fusion antibodies described herein (e.g., HIR Ab-IDS). The HIR-IDS fusion antibodies described herein bind to the extracellular domain (ECD) of the human insulin receptor.

Insulin receptors and their extracellular, insulin binding domain (ECD) have been extensively characterized in the art both structurally and functionally. See, e.g., Yip et al (2003), *J Biol. Chem,* 278(30):27329-27332; and Whittaker et al. (2005), *J Biol Chem,* 280(22):20932-20936. The amino acid and nucleotide sequences of the human insulin receptor can be found under GenBank accession No. NM_000208.

Structures that Bind to a BBB Receptor-Mediated Transport System

One noninvasive approach for the delivery of drugs to the CNS is to attach the agent of interest to a structure, e.g., molecule that binds with receptors on the BBB. The structure then serves as a vector for transport of the agent across the BBB. Such structures are referred to herein as "molecular Trojan horses (MTH)." Typically, though not necessarily, a MTH is an exogenous peptide or peptidomimetic moiety (e.g., a MAb) capable of binding to an endogenous BBB receptor mediated transport system that traverses the BBB on the endogenous BBB receptor-mediated transport system. In certain embodiments, the MTH can be an antibody to a receptor of the transport system, e.g., the insulin receptor. In some embodiments, the antibody is a monoclonal antibody (MAb). In some embodiments, the MAb is a chimeric MAb. Thus, despite the fact that Abs normally are excluded from the brain, they can be an effective vehicle for the delivery of molecules into the brain parenchyma if they have specificity for receptors on the BBB.

In some embodiments, the method comprises a method of transporting IDS across the BBB, by using a fusion antibody comprising IDS fused to an antibody capable of binding to a BBB receptor-mediated transport system. In some embodiments, the method comprises a method of transporting IDS across the BBB, by using a fusion antibody comprising IDS fused to an antibody capable of selectively binding to the a BBB receptor-mediated transport system (e.g., a receptor for one or more of the following: insulin, transferrin, insulin-like growth factors 1 and 2 (IGF1 and IGF2), leptin, and/or lipoproteins).

Figure 7:
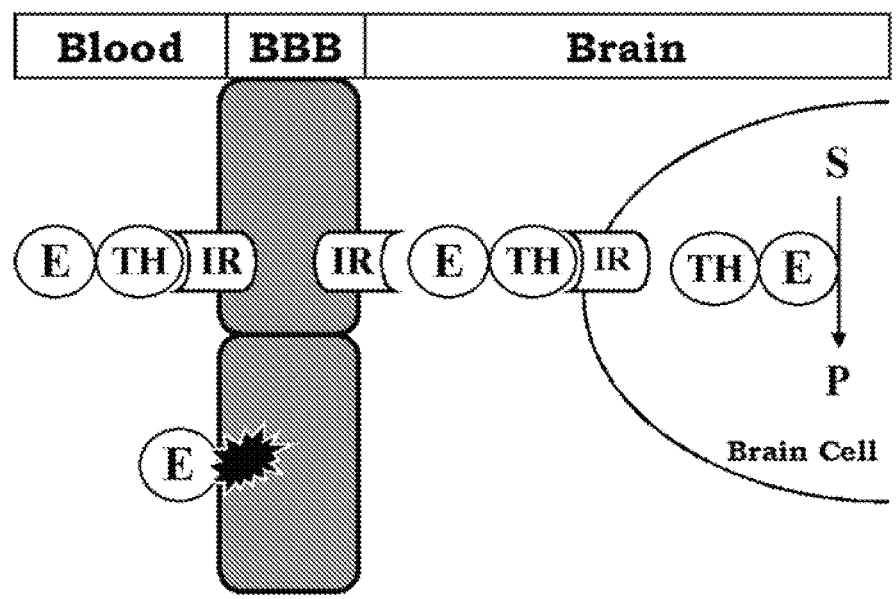

In some embodiments, the method comprises a method of transporting IDS across the BBB, by using a fusion antibody comprising IDS fused to an antibody capable of selectively binding to the ECD of the insulin receptor. Insulin receptors expressed on the BBB can thereby serve as a vector for transport of the IDS across the BBB. Certain ECD-specific antibodies may mimic the endogenous ligand and thereby traverse a plasma membrane barrier via transport on the specific receptor system. Such insulin receptor antibodies act as molecular "Trojan horses," or "TH" as depicted schematically in FIG. 7. By itself, IDS normally does not cross the blood-brain barrier (BBB). However, following fusion of the IDS to the TH, the enzyme is able to cross the BBB, and the brain cell membrane, by trafficking on the IR, which is expressed at both membranes in the brain.

Thus, despite the fact that antibodies and other macromolecules are normally excluded from the brain, they can be an effective vehicle for the delivery of molecules into the brain parenchyma if they have specificity for the extracellular domain of a receptor expressed on the BBB, e.g., the insulin receptor. In certain embodiments, an HIR Ab-IDS fusion antibody binds an exofacial epitope on the human BBB HIR and this binding enables the fusion antibody to traverse the BBB via a transport reaction that is mediated by the human BBB insulin receptor.

The term "antibody" describes an immunoglobulin whether natural or partly or wholly synthetically produced. The term also covers any polypeptide or protein having a binding domain which is, or is homologous to, an antigen-binding domain. CDR grafted antibodies are also contemplated by this term.

"Native antibodies" and "native immunoglobulins" are usually heterotetrameric glycoproteins of about 150,000 daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("VH") followed by a number of constant domains ("CH"). Each light chain has a variable domain at one end ("VL") and a constant domain ("CL") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable domain" refers to protein domains that differ extensively in sequence among family members (i.e., among different isoforms, or in different species). With respect to antibodies, the term "variable domain" refers to the variable domains of antibodies that are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the "framework region" or "FR". The variable domains of unmodified heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from three "complementarity determining regions" or "CDRs", which directly bind, in a complementary manner, to an antigen and are known as CDR1, CDR2, and CDR3 respectively.

In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3); Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, J. Mol. Biol. 196:901 917 (1987)).

As used herein, "variable framework region" or "VFR" refers to framework residues that form a part of the antigen binding pocket or groove and/or that may contact antigen. In some embodiments, the framework residues form a loop that is a part of the antigen binding pocket or groove. The amino acids residues in the loop may or may not contact the antigen. In an embodiment, the loop amino acids of a VFR are determined by inspection of the three-dimensional structure of an antibody, antibody heavy chain, or antibody light chain. The three-dimensional structure can be analyzed for solvent accessible amino acid positions as such positions are likely to form a loop and/or provide antigen contact in an antibody variable domain Some of the solvent accessible positions can tolerate amino acid sequence diversity and others (e.g. structural positions) can be less diversified. The three dimensional structure of the antibody variable domain can be derived from a crystal structure or protein modeling. In some embodiments, the VFR comprises, consist essentially of, or consists of amino acid positions corresponding to amino acid positions 71 to 78 of the heavy chain variable domain, the positions defined according to Kabat et al., 1991. In some embodiments, VFR forms a portion of Framework Region 3 located between CDRH2 and CDRH3. The VFR can form a loop that is well positioned to make contact with a target antigen or form a part of the antigen binding pocket.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA, and IgA2. The heavy-chain constant domains (Fc) that correspond to the different classes of immunoglobulins are called $\alpha$, $\delta$, $\epsilon$, $\gamma$, and $\mu$, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("$\kappa$") and lambda or ("$\lambda$"), based on the amino acid sequences of their constant domains.

In referring to an antibody or fusion antibody described herein, the terms "selectively bind," "selectively binding," "specifically binds," or "specifically binding" refer to binding to the antibody or fusion antibody to its target antigen for which the dissociation constant (Kd) is about $10^{-6}$ M or lower, i.e., $10^{-7}$, $10^{-8}$, $10^{-9}$, $10^{-10}$, $10^{-11}$, or $10^{-12}$M.

The term antibody as used herein will also be understood to mean one or more fragments of an antibody that retain the ability to specifically bind to an antigen, (see generally, Holliger et al., Nature Biotech. 23 (9) 1126-1129 (2005)). Non-limiting examples of such antibodies include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544 546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423 426; and Huston et al. (1988) Proc. Natl. Acad. Sci. USA 85:5879 5883; and Osbourn et al. (1998) Nat. Biotechnol. 16:778). Such single chain antibodies are also intended to be encompassed within the term antibody. Any VH and VL sequences of specific scFv can be linked to human immunoglobulin constant region cDNA or genomic sequences, in order to generate expression vectors encoding complete IgG molecules or other isotypes. VH and VL can also be used in the generation of Fab, Fv or other fragments of immunoglobulins using either protein chemistry or recombinant DNA technology. Other forms of single chain antibodies, such as diabodies are also encompassed.

"F(ab')2" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of VL (L chain variable region) and CL (L chain constant region), and an H chain fragment composed of VH (H chain variable region) and CHγ1 (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise a VH, a VL, or both a VH and VL domain of an antibody, wherein both domains are present in a single polypeptide chain. In some embodiments, the Fv polypeptide further comprises a polypeptide linker between the VH and VL domains which enables the sFv to form the desired structure for antigen binding. For a review of sFv see, e.g., Pluckthun in The Pharmacology of Monoclonal Antibodies, Vol. 113, Rosenburg and Moore eds. Springer-Verlag, New York, pp. 269 315 (1994).

A "chimeric" antibody includes an antibody derived from a combination of different mammals. The mammal may be, for example, a rabbit, a mouse, a rat, a goat, or a human. The combination of different mammals includes combinations of fragments from human and mouse sources.

In some embodiments, an antibody of the present invention is a monoclonal antibody (MAb), typically a chimeric human-mouse antibody derived by humanization of a mouse monoclonal antibody. Such antibodies are obtained from, e.g., transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas.

For use in humans, a chimeric antibody (e.g., HIR Ab, other antibodies capable of crossing the BBB) is preferred that contains enough human sequence that it is not significantly immunogenic when administered to humans, e.g., about 80% human and about 20% mouse, or about 85% human and about 15% mouse, or about 90% human and about 10% mouse, or about 95% human and 5% mouse, or greater than about 95% human and less than about 5% mouse. A more highly humanized form of the antibody(e.g., HIR Ab, other antibodies capable of crossing the BBB) can also be engineered, and the humanized antibody (e.g. HIR Ab) has activity comparable to the murine HIR Ab and can be used in embodiments of the invention. See, e.g., U.S. Patent Application Publication Nos. 20040101904, filed Nov. 27, 2002 and 20050142141, filed Feb. 17, 2005. Humanized antibodies to the human BBB insulin receptor with sufficient human sequences for use in the invention are described in, e.g., Boado et al. (2007), *Biotechnol Bioeng,* 96(2):381-391.

In exemplary embodiments, the HIR antibodies or HIR-IDS fusion antibodies derived therefrom contain an immunoglobulin heavy chain comprising CDRs corresponding to the sequence of at least one of the HC CDRs listed in FIG. 3 (SEQ ID NOs 1-3) or a variant thereof. For example, a HC CDR1 corresponding to the amino acid sequence of SEQ ID NO:1 with up to 1, 2, 3, 4, 5, or 6 single amino acid mutations, a HC CDR2 corresponding to the amino acid sequence of SEQ ID NO:2 with up to 1, 2, 3, 4, 5, 6, 7, 8, 9, or 10 single amino acid mutations, or a HC CDR3 corresponding to the amino acid sequence of SEQ ID NO:3 with up to 1, or 2 single amino acid mutations, where the single amino acid mutations are substitutions, deletions, or insertions.

In other embodiments, the HIR Abs or HIR Ab-IDS fusion Abs contain an immunoglobulin HC the amino acid sequence of which is at least 50% identical (i.e., at least, 55, 60, 65, 70, 75, 80, 85, 90, 95, or any other percent up to 100% identical) to SEQ ID NO:7 (shown in FIG. 1).

In some embodiments, the HIR Abs or HIR Ab-IDS fusion Abs include an immunoglobulin light chain comprising CDRs corresponding to the sequence of at least one of the LC CDRs listed in FIG. 3 (SEQ ID NOs: 4-6) or a variant thereof. For example, a LC CDR1 corresponding to the amino acid sequence of SEQ ID NO:4 with up to 1, 2, 3, 4, or 5 single amino acid mutations, a LC CDR2 corresponding to the amino acid sequence of SEQ ID NO:5 with up to 1, 2, 3, or 4 single amino acid mutations, or a LC CDR3 corresponding to the amino acid sequence of SEQ ID NO:6 with up to 1, 2, 3, 4, or 5 single amino acid mutations.

In other embodiments, the HIR Abs or HIR Ab-IDS fusion Abs contain an immunoglobulin LC the amino acid sequence of which is at least 50% identical (i.e., at least, 55, 60, 65, 70, 75, 80, 85, 90, 95, or any other percent up to 100% identical) to SEQ ID NO:8 (shown in FIG. 2).

In yet other embodiments, the HIR Abs or HIR Ab-IDS fusion Abs contain both a heavy chain and a light chain corresponding to any of the above-mentioned HIR heavy chains and HIR light chains.

HIR antibodies used in the invention may be glycosylated or non-glycosylated. If the antibody is glycosylated, any pattern of glycosylation that does not significantly affect the function of the antibody may be used. Glycosylation can occur in the pattern typical of the cell in which the antibody is made, and may vary from cell type to cell type. For example, the glycosylation pattern of a monoclonal antibody produced by a mouse myeloma cell can be different than the glycosylation pattern of a monoclonal antibody produced by a transfected Chinese hamster ovary (CHO) cell. In some embodiments, the antibody is glycosylated in the pattern produced by a transfected Chinese hamster ovary (CHO) cell.

One of ordinary skill in the art will appreciate that current technologies permit a vast number of sequence variants of candidate antibodies (e.g., HIR Ab, other antibodies capable of crossing the BBB) can be generated be (e.g., in vitro) and screened for binding to a target antigen such as the ECD of the human insulin receptor or an isolated epitope thereof. See, e.g., Fukuda et al. (2006) "In vitro evolution of single-chain antibodies using mRNA display," *Nuc. Acid Res.,* 34(19) (published online) for an example of ultra high throughput screening of antibody sequence variants. See also, Chen et al. (1999), "In vitro scanning saturation mutagenesis of all the specificity determining residues in an antibody binding site," *Prot Eng,* 12(4): 349-356. An insulin receptor ECD can be purified as described in, e.g., Coloma et al. (2000) *Pharm Res,* 17:266-274, and used to screen for HIR Abs and HIR Ab sequence variants of known HIR Abs.

Accordingly, in some embodiments, a genetically engineered HIR Ab, with the desired level of human sequences, is fused to an IDS, to produce a recombinant fusion antibody that is a bi-functional molecule. The HIR Ab-IDS fusion antibody: (i) binds to an extracellular domain of the human insulin receptor; (ii) catalyzes hydrolysis of linkages in dermatan and/or heparan sulfate; and (iii) is able to cross the BBB, via transport on the BBB HIR, and retain IDS activity once inside the brain, following peripheral administration.

Iduronate 2-Sulfatase (IDS)

Systemic administration (e.g., by intravenous injection) of recombinant IDS (e.g., Elaprase®) fails to rescue a deficiency of IDS in the CNS of patients suffering from Hunter's syndrome. IDS does not cross the BBB, and the lack of transport of the enzyme across the BBB prevents it from having a significant therapeutic effect in the CNS following peripheral administration. However, in some embodiments of the present invention, when the IDS is fused to an antibody capable of crossing the BBB (e.g., HIR Ab), the IDS is able to enter the CNS from blood following a non-invasive peripheral route of administration such as intravenous, intra-arterial, intramuscular, subcutaneous, intraperitoneal, or even oral administration, or other route described herein. Administration of a IDS fusion antibody (e.g., HIR Ab-IDS) enables delivery of IDS activity into the brain from peripheral blood. Described herein is the determination of a systemic dose of a IDS fusion antibody (e.g., HIR Ab-IDS) that is therapeutically effective for treating an IDS deficiency in the CNS. As described herein, appropriate systemic doses of an IDS fusion antibody (e.g., HIR Ab-IDS) are established based on a quantitative determination of CNS uptake characteristics and enzymatic activity of an HIR Ab-enzyme fusion antibody.

Dermatan sulfate, heparan sulfate and heparin are variably sulfated glycosaminoglycans, which are long, unbranched polysaccharides made up of a repeating disaccharide unit. L-iduronate (or L-iduronic acid) is a major component of dermatan sulfate and heparin. It is also present in heparan sulfate. As used herein, IDS (e.g., the human IDS sequence listed under GenBank Accession No. NP_000193) refers to any naturally occurring or artificial enzyme that can catalyze the hydrolysis or removal of 2-sulfate groups of the L-iduronate 2-sulfate units of dermatan sulfate, heparan sulfate and heparin.

IDS is a member of a family of sulfatases that requires a specific post-translational modification for expression of IDS enzyme activity. The activity of the IDS enzyme is activated following the conversion of Cys-59 to a formylglycine residue by a sulfatase modifying factor type 1 (SUMF1), which is also called the formylglycine generating enzyme (FGE). In some embodiments, the fusion antibody comprising IDS is post-translationally modified by a sulfatase modifying factor type 1 (SUMF1). In some embodiments, the post-translational modification comprises a cysteine to formylglycine conversion. In some embodiments, the fusion antibody comprises an IDS that comprises a formylglycine residue.

In some embodiments, the subject composition (or method) comprises an IDS has an amino acid sequence that is at least 50% identical (i.e., at least, 55, 60, 65, 70, 75, 80, 85, 90, 95, or any other percent up to 100% identical) to the amino acid sequence of human IDS, a 550 amino acid protein listed under GenBank Accession No. NP_000193, or a 525 amino acid subsequence thereof, which lacks a 25 amino acid signal peptide, and corresponds to SEQ ID NO:9 (FIG. 4). The structure-function relationship of human IDS is well established, as described in, e.g., Sukegawa-Hayasaka et al. (2006), "Effect of Hunter disease (mucopolysaccharidosis type II) mutations on molecular phenotypes of iduronate-2-sulfatase: enzymatic activity, protein processing and structural analysis," *J. Inherit. Metab. Dis.,* 29: 755-761. In particular, residues that are critical to the function of IDS include, e.g., Arg 48, Ala 85, Pro 86, Ser 333, Trp 337, Ser 349, Arg 468, and Gln 531.

In some embodiments, IDS has an amino acid sequence at least 50% identical (i.e., at least, 55, 60, 65, 70, 75, 80, 85, 90, 95, or any other percent up to 100% identical) to SEQ ID NO:9 (shown in FIG. 4). Sequence variants of a canonical IDS sequence such as SEQ ID NO:9 can be generated, e.g., by random mutagenesis of the entire sequence or specific subsequences corresponding to particular domains. Alternatively, site directed mutagenesis can be performed reiteratively while avoiding mutations to residues known to be critical to IDS function such as those given above. Further, in generating multiple variants of an IDS sequence, mutation tolerance prediction programs can be used to greatly reduce the number of non-functional sequence variants that would be generated by strictly random mutagenesis. Various programs) for predicting the effects of amino acid substitutions in a protein sequence on protein function (e.g., SIFT, Poly-Phen, PANTHER PSEC, PMUT, and TopoSNP) are described in, e.g., Henikoff et al. (2006), "Predicting the Effects of Amino Acid Substitutions on Protein Function," *Annu. Rev. Genomics Hum. Genet.,* 7:61-80. IDS sequence variants can be screened for of IDS activity/retention of IDS activity by, e.g., 4-methylumbelliferyl α-L-iduronide-2-sulphate (4-MUS) flurometric IDS assays known in the art. See, e.g., Voznyi et al. (2001), *J. Inherit. Metab. Dis.* 24: 675-680. One unit of IDS activity is defined as the hydrolysis of 1 nmole substrate/hour. Accordingly, one of ordinary skill in the art will appreciate that a very large number of operable IDS sequence variants can be obtained by generating and screening extremely diverse "libraries" of IDS sequence variants by methods that are routine in the art, as described above.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson and Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO:9 or SEQ ID NO: 16) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, SIAM *J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

The present invention also includes proteins having a conservative amino acid change, compared with an amino acid sequence disclosed herein. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods of the invention.

Compositions

Compositions of the invention are useful for multiple reasons including being useful for: transporting IDS across the BBB, delivering a therapeutic effective dose of IDS, and/or retaining activity of the IDS once transported across the BBB, or once fused to a targeting antibody. Compositions of the invention are also useful in that the IDS and/or the structure it is bound to (e.g., immunogloblulin, antibody) within the fusion antibody each retains a certain amount of its activity compared to its activity as a separate entity.

In some embodiments, the invention provides compositions containing an IDS covalently linked to a structure (e.g., immunoglobulin, antibody) that is capable of crossing the blood brain barrier (BBB), where the IDS retains at least about 10, 20, 30, 40, 50, 60, 70, 80, 90, 95, 99, or 100% of its activity, compared to its activity as a separate entity. In some embodiments, the invention provides compositions containing an IDS covalently linked to a structure (e.g., immunoglobulin, antibody) that is capable of crossing the blood brain barrier (BBB), where the structure retains at least about 10, 20, 30, 40, 50, 60, 70, 80, 90, 95, 99, or 100% of its activity, compared to its activity as a separate entity. In some embodiments, the invention provides compositions containing an IDS covalently linked to a structure (e.g., immunoglobulin, antibody) that is capable of crossing the blood brain barrier (BBB), where the structure and the IDS each retains at least about 10, 20, 30, 40, 50, 60, 70, 80, 90, 95, 99, or 100% of its activity, compared to its activity as a separate entity. In some embodiments, the IDS retains at least about 10% of its activity compared to its activity as a separate entity. In some embodiments, the IDS retains at least 20% of its activity, compared to its activity as a separate entity. In some embodiments, the IDS retains at least 30% of its activity, compared to its activity as a separate entity. In some embodiments, the IDS retains at least 40% of its activity, compared to its activity as a separate entity. In some embodiments, the IDS retains at least 50% of its activity, compared to its activity as a separate entity. In some embodiments, the IDS retains at least 60% of its activity, compared to its activity as a separate entity.

The invention also provides compositions containing an IDS that is covalently linked to a chimeric MAb to the human BBB insulin receptor. The invention also provides pharmaceutical compositions that contain one or more compositions of the invention and a pharmaceutically acceptable excipient.

In some embodiments, the subject composition comprises a IDS fusion antibody where at least about 0.3% (i.e., about 0.32%), 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered IDS fusion antibody is capable of being delivered to the brain as a result of its uptake from peripheral blood across the BBB. In some embodiments, the composition comprises an IDS fusion antibody wherein at least 0.5%, (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered dose of the IDS fusion antibody is delivered to the brain within two hours or less, i.e., 1.8, 1.7, 1.5, 1.4, 1.3, 1.2, 1.1, 0.9, 0.8, 0.6, 0.5 or any other period from about 0.5 to about two hours after systemic administration.

In some embodiments, the present IDS fusion antibodies can cross the BBB, and thereby provide at least 0.125 units of IDS activity/mg protein in the subject's brain, e.g., 0.14, 0.15, 0.16, 0.17, 0.18, 0.19, 0.2, 0.21, 0.22, 0.23, 0.24, 0.25, 0.3, 0.4, 0.5, 0.75, 1.0, 1.5, 2, or any other value from 0.125 to 2.5 of units of IDS activity/mg protein in the subject's brain. In some embodiments, the total number of units of IDS activity delivered to a subject's brain is at least, 12,500 units, e.g., at least 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, 250,000 or any other total number of IDS units from about 12,500 to 250,000 units of IDS activity. In some embodiments, the total number of units of IDS activity delivered to a subject's brain is at least, 10,000 units, e.g., at least 10,000, 12,500, 25,000, 30,000, 35,000, 40,000, 45,000, 50,000, 60,000, 70,000, 80,000, 90,000, 110,000, 120,000, 130,000, 140, 000, 150,000, 160,000, 170,000, 180,000, 190,000, 200,000, 210,000, 220,000, 230,000, 250,000, 300,000, 5000,000 any other total number of IDS units from about 10,000 to 500,000 units of IDS activity. In some embodiments, at least about 25,000 units of iduronate-2-sulfatase activity is delivered to the brain, normalized per 50 kg body weight. In some embodiments, at least about 10,000, 15,000, 25,000, 30,000, 35,000, 40,000, 45,000, 50,000, 60,000, 70,000, 80,000, 90,000, 110,000, 120,000, 130,000, 140,000, 150,000, 160, 000, 170,000, 180,000, 190,000, 200,000, 210,000, 220,000, 230,000, 250,000 units of iduronate-2-sulfatase activity is delivered to the brain, normalized per 50 kg body weight. In some embodiments, at least about 25,000 000 units of iduronate-2-sulfatase activity is delivered to the brain, normalized per 50 kg body weight. In some embodiments, a therapeutically effective systemic dose comprises at least $5\times10^5$, $1\times10^6$, $2\times10^6$, $3\times10^6$, 4, $10^6$, $5\times10^6$, $6\times10^6$, $7\times10^6$, $8\times10^6$, $9\times10^6$, $1\times10^7$, $1.1\times10^7$, $1.2\times10^7$, $1.5\times10^7$, $1.6\times10^7$, $1.7\times10^7$, $1.8\times10^7$, $1.9\times10^7$, $2\times10^7$, $2.1\times10^7$, $3\times10^7$, or any other systemic dose from about $5\times10^5$ to $3\times10^7$ units of IDS activity. In other embodiments, a therapeutically effective systemic dose is at least about 20,000 units, or at least about 10,000 units of IDS activity/kg body weight, at least about 10,000, 15,000, 20,000, 22,000, 24,000, 25,000, 30,000, 40,000, 50,000, 60,000, 70,000, 80,000, 90,000, 100,000, 125,000, 150,000, 200,000, or 500,000 units/kg body weight.

One of ordinary skill in the art may appreciate that the mass amount of a therapeutically effective systemic dose of an IDS fusion antibody (e.g., HIR Ab-IDS) will depend, in part, on its IDS specific activity. In some embodiments, the IDS specific activity of the IDS fusion antibody is at least 10,000 U/mg of protein, at least about 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, 50,000, or any other specific activity value from about 10,000 units/mg to about 50,000 units/mg.

In some embodiments, the structure that is capable of crossing the BBB utilizes an endogenous BBB receptor mediated transport system, such as a system that utilizes the insulin receptor, transferrin receptor, leptin receptor, LDL receptor, or IGF receptor. In some embodiments, the endogenous BBB receptor mediated transport system is the insulin BBB receptor mediated transport system. In some embodiments, the structure that is capable of crossing the BBB is an antibody, e.g., a monoclonal antibody (MAb) such as a chimeric MAb. The antibody can be a chimeric antibody with sufficient human sequence that it is suitable for administration to a human. In embodiments of the above fusion proteins, the structure capable of crossing the blood brain barrier crosses the BBB on an endogenous BBB receptor-mediated transporter, such as a transporter selected from the group consisting of the insulin transporter, the transferrin transporter, the leptin transporter, the LDL transporter, and the IGF receptor. In some embodiments, the endogenous BBB receptor-mediated transporter is selected from the group consisting of the insulin transporter and the transferrin transporter. In some embodiments, the endogenous BBB receptor-mediated transporter is the insulin transporter, e.g., the human insulin transporter. The structure capable of crossing the BBB can be an antibody, e.g., a MAb such as a chimeric MAb. The antibody can be an antibody to an endogenous BBB receptor-mediated transporter, as described herein.

The antibody can be glycosylated or nonglycosylated; in some embodiments, the antibody is glycosylated, e.g., in a glycosylation pattern produced by its synthesis in a CHO cell. In embodiments in which the structure is an antibody, the covalent linkage between the antibody and the IDS may be a linkage between any suitable portion of the antibody and the IDS, as long as it allows the IDS fusion antibody to cross the blood brain barrier and/or the IDS to retain a therapeutically useful portion of its activity within the CNS. In certain embodiments, the covalent link is between one or more light chains of the antibody and the IDS. The IDS can be covalently linked by its carboxy or amino terminus to the carboxy or amino terminus of the light chain (LC) or heavy chain (HC) of the antibody. Any suitable linkage may be used, e.g., carboxy terminus of light chain to amino terminus of peptide, carboxy terminus of heavy chain to amino terminus of peptide, amino terminus of light chain to amino terminus of peptide, amino terminus of heavy chain to amino terminus of peptide, carboxy terminus of light chain to carboxy terminus of peptide, carboxy terminus of heavy chain to carboxy terminus of peptide, amino terminus of light chain to carboxy terminus of peptide, or amino terminus of heavy chain to carboxy terminus of peptide. In some embodiments, the linkage is from the carboxy terminus of the HC to the amino terminus of the peptide. It will be appreciated that a linkage between terminal amino acids is not required, and any linkage which meets the requirements of the invention may be used; such linkages between non-terminal amino acids of peptides are readily accomplished by those of skill in the art.

In some embodiments, more than one molecule of the IDS is attached to the structure that crosses the BBB. In some embodiments, 2, 3, 4, 5, 6, 7, 8, 9, 10, or more than 10 IDS molecules (or fraction thereof) may be attached to the structure that is capable of crossing the blood brain barrier.

The bifunctional IDS fusion antibody (e.g., HIR Ab-IDS) described herein, may retain a high proportion of the activity of their separate constituent proteins, e.g., binding of the HIR Ab to the IR ECD, and the enzymatic activity of IDS. Construction of cDNAs and expression vectors encoding any of the proteins described herein, as well as their expression and purification are well within those of ordinary skill in the art, and are described in detail herein in, e.g., Examples 1-3, and, in Boado et al (2007), *Biotechnol Bioeng* 96:381-391, U.S. patent application Ser. No. 11/061,956, and U.S. patent application Ser. No. 11/245,710.

Described herein are bifunctional IDS fusion antibodies (e.g., HIR Ab-IDS) containing a targeting antibody (e.g., HIR Ab), as described herein, capable of crossing the BBB fused to IDS, where the targeting antibody (e.g., HIR Ab) capable of crossing the blood brain barrier and the IDS each retain an average of at least about 10, 20, 30, 40, 50, 60, 70, 80, 90, 95, 99, or 100% of their activities, compared to their activities as separate entities. In some embodiments, the invention provides a HIR Ab-IDS fusion antibody where the HIR Ab and IDS each retain an average of at least about 50% of their activities, compared to their activities as separate entities. In some embodiments, the invention provides a HIR Ab-IDS fusion antibody where the HIR Ab and IDS each retain an average of at least about 60% of their activities, compared to their activities as separate entities. In some embodiments, the invention provides a HIR Ab-IDS fusion antibody where the HIR Ab and IDS each retain an average of at least about 70% of their activities, compared to their activities as separate entities. In some embodiments, the invention provides a HIR Ab-IDS fusion antibody where the HIR Ab and IDS each retain an average of at least about 80% of their activities, compared to their activities as separate entities. In some embodiments, the invention provides a fusion HIR Ab-IDS fusion antibody where the HIR Ab and IDS each retain an average of at least about 90% of their activities, compared to their activities as separate entities. In some embodiments, the HIR Ab retains at least about 10, 20, 30, 40, 50, 60, 70, 80, 90, 95, 99, or 100% of its activity, compared to its activity as a separate entity, and the IDS retains at least about 10, 20, 30, 40, 50, 60, 70, 80, 90, 95, 99, or 100% of its activity, compared to its activity as a separate entity. Accordingly, described herein are compositions containing a bifunctional IDS fusion antibody (e.g., HIR Ab-IDS) capable of crossing the BBB, where the constituent antibody (e.g., HIR Ab) and IDS each retain, as part of the fusion antibody, an average of at least about 10, 20, 30, 40, 50, 60, 70, 80, 90, 95, 99, or 100% of their activities, e.g., HIR binding and IDS activity, respectively, compared to their activities as separate proteins. An HIR Ab IDS fusion antibody refers to a fusion protein comprising any of the HIR antibodies and IDSs described herein.

In some embodiments, the IDS fusion antibodies (e.g., HIR Ab-IDS) described herein, comprise a covalent linkage between the carboxy terminus of the antibody (e.g., HIR Ab) and the amino terminus of the IDS (or, between the amino terminus of the antibody and the carboxy terminus of the IDS), wherein the IDS fusion antibody (e.g., HIR Ab-IDS) binds to the receptor-mediated BBB transport system (e.g., to the ECD of the IR) and crosses the blood brain barrier. In some embodiments, the IDS retains a therapeutically useful portion of its activity. In some embodiments of the invention comprising an IDS fusion antibody (e.g., HIR Ab-IDS) described herein, the covalent linkage between the antibody and the IDS may be to the carboxy or amino terminal of the targeting antibody (e.g., HIR antibody) and the amino or carboxy terminal of the IDS and linkage allows the HIR Ab-IDS fusion antibody to bind to the ECD of the IR and cross the blood brain barrier, and allows the IDS to retain a therapeutically useful portion of its activity. In certain embodiments, the covalent link is between an HC of the antibody and the IDS or a LC of the antibody and the IDS. Any suitable linkage may be used, e.g., carboxy terminus of light chain to amino terminus of IDS, carboxy terminus of heavy chain to amino terminus of IDS, amino terminus of light chain to amino terminus of IDS, amino terminus of heavy chain to amino terminus of IDS, carboxy terminus of light chain to carboxy terminus of IDS, carboxy terminus of heavy chain to carboxy terminus of IDS, amino terminus of light chain to carboxy terminus of IDS, or amino terminus of heavy chain to carboxy terminus of IDS. In some embodiments, the linkage is from the carboxy terminus of the HC to the amino terminus of the IDS.

The IDS may be fused, or covalently linked, to the targeting antibody (e.g., MAb, HIR-MAb) through a linker. A linkage between terminal amino acids can be accomplished by an intervening peptide linker sequence that forms part of the fused amino acid sequence. The peptide sequence linker may be 0, 1, 2, 3, 4, 5, 6, 7, 8, 9, 10, or more than 10 amino acids in length. In some embodiments, including some preferred embodiments, the peptide linker is less than 20, 15, 14, 13, 12, 11, 10, 9, 8, 7, 6, 5, 4, 3, 2, or 1 amino acids in length. In some embodiments, including preferred embodiments, the peptide linker is at least 0, 1, 2, 3, 4, 5, 6, 7, 8, 9, 10 amino acids in length. In some embodiments, the IDS is directly linked to the targeting antibody, and is therefore 0 amino acids in length. In some embodiments, there is no linker linking the IDS to the targeting antibody. In some embodiments, the amino terminus of the IDS is fused directly to the carboxyl terminal of the targeting antibody (e.g., HIR MAb), and therefore there is no linker linking the IDS to the targeting antibody (e.g., HIR MAb). In some embodiments, the carboxy terminus of the IDS is fused directly to the amino terminus of the targeting antibody (e.g., HIR MAb), and therefore there is no linker linking the IDS to the targeting antibody (e.g., HIR MAb). In some embodiments, the amino terminus of the IDS is fused directly to the carboxyl terminus of the HC of the to the targeting antibody (e.g., HIR MAb). In some embodiments, the amino terminus of the IDS is fused to the carboxyl terminal of the targeting antibody (e.g., HIR MAb) through a linker (e.g., any linker described herein). In some embodiments, the carboxy terminus of the IDS is fused to the amino terminus of the targeting antibody (e.g., HIR MAb) through a linker (e.g., any linker described herein). In some embodiments, the amino terminus of the IDS is fused to the carboxyl terminus of the HC of the HIR through a linker (e.g., any linker described herein).

In some embodiments, the linker comprises glycine, serine, and/or alanine residues in any combination or order. In some cases, the combined percentage of glycine, serine, and alanine residues in the linker is at least 5%, 10%, 15%, 20%, 25%, 30%, 40%, 50%, 60%, 70%, 75%, 80%, 90%, or 95% of the total number of residues in the linker. In some preferred embodiments, the combined percentage of glycine, serine, and alanine residues in the linker is at least 50%, 60%, 70%, 75%, 80%, 90%, or 95% of the total number of residues in the linker. In some embodiments, any number of combinations of amino acids (including natural or synthetic amino acids) can be used for the linker. In some embodiments, a two amino acid linker is used. In some embodiments, the linker has the sequence Ser-Ser. In some embodiments, a two amino acid linker comprises glycine, serine, and/or alanine residues in any combination or order (e.g., Gly-Gly, Ser-Gly, Gly-Ser, Ser-Ser, Ala-Ala, Ser-Ala, or Ala-Ser linker). In some embodiments, a two amino acid linker consists of one glycine, serine, and/or alanine residue along with another amino acid (e.g., Ser-X, where X is any known amino acid). In still other embodiments, the two-amino acid linker consists of any two amino acids (e.g., X-X), except gly, ser, or ala.

As described herein, in some embodiments, a linker for use in the present disclosure, is greater than two amino acids in length. Such linker may also comprise glycine, serine, and/or alanine residues in any combination or order, as described further herein. In some embodiments, the linker consists of one glycine, serine, and/or alanine residue along with other amino acids (e.g., Ser-nX, where X is any known amino acid, and n is the number of amino acids). In still other embodiments, the linker consists of any two amino acids (e.g., X-X). In some embodiments, said any two amino acids are Gly, Ser, or Ala, in any combination or order, and within a variable number of amino acids intervening between them. In an example of an embodiment, the linker consists of at least one Gly. In an example of an embodiment, the linker consists of at least one Ser. In an example of an embodiment, the linker consists of at least one Ala. In some embodiments, the linker consists of at least 1, 2, 3, 4, 5, 6, 7, 8, 9, or 10 Gly, Ser, and/or Ala residues. In preferred embodiments, the linker comprises Gly and Ser in repeating sequences, in any combination or number, such as (Gly$_4$Ser)$_3$ (SEQ ID NO: 19), or other variations.

A linker for use in the present invention may be designed by using any method known in the art. For example, there are multiple publicly-available programs for determining optimal amino acid linkers in the engineering of fusion proteins. Publicly-available computer programs (such as the LINKER program) that automatically generate the amino acid sequence of optimal linkers based on the user's input of the sequence of the protein and the desired length of the linker may be used for the present methods and compositions. Often, such programs may use observed trends of naturally-occurring linkers joining protein subdomains to predict optimal protein linkers for use in protein engineering. In some cases, such programs use other methods of predicting optimal linkers. Examples of some programs suitable for predicting a linker for the present invention are described in the art, see, e.g., Xue et al. (2004) Nucleic Acids Res. 32, W562-W565 (Web Server issue providing internet link to LINKER program to assist the design of linker sequences for constructing functional fusion proteins); George and Heringa, (2003), Protein Engineering, 15(11): 871-879 (providing an internet link to a linker program and describing the rational design of protein linkers); Argos, (1990), J. Mol. Biol. 211:943-958; Arai et al. (2001) Protein Engineering, 14(8):529-532; Crasto and Feng, (2000) Protein Engineering 13(5):309-312.

The peptide linker sequence may include a protease cleavage site, however this is not a requirement for activity of the IDS; indeed, an advantage of these embodiments of the present invention is that the bifunctional IDS fusion antibody (e.g., HIR Ab-IDS) described herein, without cleavage, is partially or fully active both for transport and for activity once across the BBB. FIG. 5 shows an exemplary embodiment of the amino acid sequence of a HIR Ab-IDS fusion antibody (SEQ ID NO:10) in which the HC is fused through its carboxy terminus via a two amino acid "ser-ser" linker to the amino terminus of the IDS. In some embodiments, the fused IDS sequence is devoid of its 25 amino acid signal peptide, as shown in FIG. 4.

In some embodiments, an IDS fusion antibody (e.g., HIR Ab-IDS) described herein comprises both a HC and a LC. In some embodiments, an IDS fusion antibody (e.g., HIR Ab-IDS) described herein is a monovalent antibody. In other embodiments, the IDS fusion antibody (e.g., HIR Ab-IDS) described herein is a divalent antibody, as described herein in the Example section.

The targeting antibody (e.g., HIR Ab) used as part of the IDS fusion antibody can be glycosylated or nonglycosylated; in some embodiments, the antibody is glycosylated, e.g., in a glycosylation pattern produced by its synthesis in a CHO cell.

As used herein, "activity" includes physiological activity (e.g., ability to cross the BBB and/or therapeutic activity), binding affinity (including binding affinity of the targeting antibody (e.g., HIR MAb) for the receptor-mediated BBB transport system), or the enzymatic activity of IDS.

Transport of the IDS fusion antibody (e.g., HIR Ab-IDS) across the BBB may be compared to transport across the BBB of the targeting antibody (e.g., HIR Ab) alone by standard methods. For example, pharmacokinetics and brain uptake of the HIR Ab-IDS fusion antibody by a model animal, e.g., a mammal such as a primate, may be used. Similarly, standard models for determining IDS activity may also be used to compare the function of the IDS alone and as part of a HIR Ab-IDS fusion antibody. See, e.g., Example 3, which demonstrates the enzymatic activity of IDS versus HIR Ab-IDS fusion antibody. Binding affinity for the IR ECD can be compared for the HIR Ab-IDS fusion antibody versus the HIR Ab alone. See, e.g., Example 3 herein.

Also included herein are pharmaceutical compositions that contain one or more IDS fusion antibodies (e.g., HIR Ab-IDS) described herein and a pharmaceutically acceptable excipient. A thorough discussion of pharmaceutically acceptable carriers/excipients can be found in Remington's Pharmaceutical Sciences, Gennaro, A R, ed., 20th edition, 2000: Williams and Wilkins Pa., USA. Pharmaceutical compositions of the invention include compositions suitable for administration via any peripheral route, including intravenous, subcutaneous, intramuscular, intraperitoneal injection; oral, rectal, transbuccal, pulmonary, transdermal, intranasal, or any other suitable route of peripheral administration.

The compositions of the invention are particular suited for injection, e.g., as a pharmaceutical composition for intravenous, subcutaneous, intramuscular, or intraperitoneal administration. Aqueous compositions of the present invention comprise an effective amount of a composition of the present invention, which may be dissolved or dispersed in a pharmaceutically acceptable carrier or aqueous medium. The phrases "pharmaceutically or pharmacologically accept-able" refer to molecular entities and compositions that do not produce an adverse, allergic or other untoward reaction when administered to an animal, e.g., a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include salts, for example, mineral acid salts such as hydrochlorides, hydrobromides, phosphates, sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be systemically administered in a manner compatible with the dosage formulation and in such amount as is therapeutically effective based on the criteria described herein. The formulations are easily administered in a variety of dosage forms, such as the type of injectable solutions described above, but drug release capsules and the like can also be employed The appropriate quantity of a pharmaceutical composition to be administered, the number of treatments, and unit dose will vary according to the CNS uptake characteristics of the IDS fusion antibody (e.g., HIR Ab-IDS) as described herein, and according to the subject to be treated, the state of the subject and the effect desired. The person responsible for administration will, in any event, determine the appropriate dose for the individual subject.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284, 262), transdermal administration (See U.S. Pat. Nos. 6,348, 210; and 6,322,808) and transmucosal administration (See U.S. Pat. No. 5,656,284). Such methods of administration are well known in the art. One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

Methods

Described herein are methods for delivering an effective dose of IDS to the CNS across the BBB by systemically administering a therapeutically effective amount of a HIR Ab-IDS fusion antibody, as described herein. Suitable systemic doses for delivery of a IDS fusion antibody (e.g., HIR MAb) is based on its CNS uptake characteristics and IDS specific activity as described herein. Systemic administration of a IDS fusion antibody (e.g., HIR MAb) to a subject suffering from an IDS deficiency is an effective approach to the non-invasive delivery of IDS to the CNS.

The amount of a IDS fusion antibody (e.g., HIR MAb) fusion antibody that is a therapeutically effective systemic dose depends, in part, on the CNS uptake characteristics of the of a IDS fusion antibody (e.g., HIR MAb) to be administered, as described herein., e.g., the percentage of the systemically administered dose to be taken up in the CNS, In some embodiments, 0.3% (i.e., about 0.32%), 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered of the IDS fusion antibody (e.g., HIR MAb) is delivered to the brain as a result of its uptake from peripheral blood across the BBB. In some embodiments, at least 0.5%, (i.e., about 0.32%, 0.4%, 0.48%, 0.6%, 0.74%, 0.8%, 0.9%, 1.05, 1.1, 1.2, 1.3%, 1.5%, 2%, 2.5%, 5%, or any % from about 0.3% to about 12%) of the systemically administered dose of a IDS fusion antibody (e.g., HIR MAb) is delivered to the brain within two hours or less, i.e., 1.8, 1.7, 1.5, 1.4, 1.3, 1.2, 1.1, 0.9, 0.8, 0.6, 0.5 or any other period from about 0.5 to about two hours after systemic administration.

Accordingly, in some embodiments the invention provides methods of administering a therapeutically effective amount of a IDS fusion antibody (e.g., HIR MAb) systemically, such that the amount of the IDS fusion antibody (e.g., HIR MAb) to cross the BBB provides at least 0.125 units of IDS activity/mg protein in the subject's brain, e.g., 0.14, 0.15, 0.16, 0.17, 0.18, 0.19, 0.2, 0.21, 0.22, 0.23, 0.24, 0.25, 0.3, 0.4, 0.5, 0.75, 1.0, 1.5, 2, or any other value from 0.125 to 2.5 of units of IDS activity/mg protein in the subject's brain.

In some embodiments, the total number of units of IDS activity delivered to a subject's brain is at least, 12,500 units, e.g., at least 12,500, 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, 250,000 or any other total number of IDS units from about 12,500 to 250,000 units of IDS activity.

In some embodiments, a therapeutically effective systemic dose comprises at least $5\times10^5$, $1\times10^6$, $2\times10^6$, $3\times10^6$, 4, $10^6$, $5\times10^6$, $6\times10^6$, $7\times10^6$, $8\times10^6$, $9\times10^6$, $1\times10^7$, $1.1\times10^7$, $1.2\times10^7$, $1.5\times10^7$, $1.6\times10^7$, $1.7\times10^7$, $1.8\times10^7$, $1.9\times10^7$, $2\times10^7$, $2.1\times10^7$, $3\times10^7$, or any other systemic dose from about $5\times10^5$ to $3\times10^7$ units of IDS activity.

In other embodiments, a therapeutically effective systemic dose is at least about 20,000 units of IDS activity/kg body weight, at least about 22,000, 24,000, 25,000, 30,000, 40,000, 50,000, 60,000, 70,000, 80,000, 90,000, 100,000, 125,000, 150,000, 200,000 or any other number of IDS units from about 20,000 to 200,000 units of IDS activity/kg of body weight. In some embodiments, at least about 10,000, 15,000, 25,000, 30,000, 35,000, 40,000, 45,000, 50,000, 60,000, 70,000, 80,000, 90,000, 110,000, 120,000, 130,000, 140,000, 150,000, 160,000, 170,000, 180,000, 190,000, 200,000, 210,000, 220,000, 230,000, 250,000 units of iduronate-2-sulfatase activity is delivered to the brain, normalized per 50 kg body weight. In some embodiments, at least about 25,000 000 units of iduronate-2-sulfatase activity is delivered to the brain, normalized per 50 kg body weight.

One of ordinary skill in the art will appreciate that the mass amount of a therapeutically effective systemic dose of a IDS fusion antibody (e.g., HIR MAb) will depend, in part, on its IDS specific activity. In some embodiments, the IDS specific activity of a IDS fusion antibody (e.g., HIR MAb) is at least 10,000 U/mg of protein, at least about 11,000, 12,000, 13,000, 14,000, 20,000, 21,000, 22,000, 23,000, 24,000, 25,000, 26,000, 27,000, 28,000, 30,000, 32,000, 34,000, 35,000, 36,000, 37,000, 40,000, 45,000, 50,000, or any other specific activity value from about 10,000 units/mg to about 50,000 units/mg.

Thus, with due consideration of the specific activity of a IDS fusion antibody (e.g., HIR MAb) and the body weight of a subject to be treated, a systemic dose of a IDS fusion antibody (e.g., HIR MAb) can be at least 2 mg, e.g., 5, 10, 15, 20, 25, 30, 35, 40, 45, 50, 55, 60, 65, 70, 75, 100, or any other value from about 2 mg to about 100 mg of a IDS fusion antibody (e.g., HIR MAb).

The term "systemic administration" or "peripheral administration," as used herein, includes any method of administration that is not direct administration into the CNS, i.e., that does not involve physical penetration or disruption of the BBB. "Systemic administration" includes, but is not limited to, intravenous, intra-arterial intramuscular, subcutaneous, intraperitoneal, intranasal, transbuccal, transdermal, rectal, transalveolar (inhalation), or oral administration.

Any suitable IDS fusion antibody (e.g., HIR MAb), as described herein, may be used.

An IDS deficiency as referred to herein includes, one or more conditions known as Hunter's syndrome, Hunter's disease, and mucopolysaccharidosis type II. The IDS deficiency is characterized by the buildup of heparan sulfate and dermatan sulfate that occurs in the body (the heart, liver, brain etc.).

The compositions of the invention, e.g., an HIR Ab-IDS fusion antibody, may be administered as part of a combination therapy. The combination therapy involves the administration of a composition of the invention in combination with another therapy for treatment or relief of symptoms typically found in a patient suffering from an IDS deficiency. If the composition of the invention is used in combination with another CNS disorder method or composition, any combination of the composition of the invention and the additional method or composition may be used. Thus, for example, if use of a composition of the invention is in combination with another CNS disorder treatment agent, the two may be administered simultaneously, consecutively, in overlapping durations, in similar, the same, or different frequencies, etc. In some cases a composition will be used that contains a composition of the invention in combination with one or more other CNS disorder treatment agents.

In some embodiments, the composition, e.g., an HIR Ab-IDS fusion antibody is co-administered to the patient with another medication, either within the same formulation or as a separate composition. For example, the HIR Ab-IDS fusion antibody may be formulated with another fusion protein that is also designed to deliver across the human blood-brain barrier a recombinant protein other than IDS. Further, the fusion HIR Ab-IDS fusion antibody may be formulated in combination with other large or small molecules.

TABLE 1

| GUSB enzyme activity in COS cells following transfection | | |
|---|---|---|
| Experiment | Treatment | Medium GUSB activity (nmol/hour/mL) |
| A | Lipofectamine 2000 | 65 ± 1 |
|   | pCD-GUSB | 6892 ± 631 |
| B | Lipofectamine 2000 | 76 ± 3 |
|   | pCD-HC-GUSB, pCD-LC | 72 ± 3 |
| C | Lipofectamine 2000 | 162 ± 7 |
|   | pCD-HC-GUSB, pCD-LC | 155 ± 2 |
|   | pCD-GUSB-HC, pCD-LC | 1119 ± 54 |

Mean ± SE (n = 3 dishes per point).

TABLE 2

Oligodeoxynucleotide primers used in the RT-PCR cloning of human iduronate 2-sulfatase (IDS) minus signal peptide and in the engineering of the HIRMAb-IDS expression vector.

| | | |
|---|---|---|
| IDS FWD: | phosphate-CCTCCGAAACGCAGGCCAACTCG | (SEQ ID NO. 11) |
| IDS REV: | phosphate-TCAAGGCATCAACAACTGGAAAAGATC | (SEQ ID NO. 12) |
| IDS FWD2: | phosphate-CCACAGATGCTCTGAACGTTCTTC | (SEQ ID NO. 18) |

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

Example 1. Expression and Functional Analysis of HIR Ab-GUSB Fusion Protein

The lysosomal enzyme mutated in MPS-VII, also called Sly syndrome, is β-glucuronidase (GUSB). MPS-VII results in accumulation of glycosoaminoglycans in the brain. Enzyme replacement therapy (ERT) of MPS-VII would not likely be effective for treatment of the brain because the GUSB enzyme does not cross the BBB. In an effort to re-engineer human GUSB to cross the BBB, a HIR Ab-GUSB fusion protein project was initiated.

Human GUSB cDNA corresponding to amino acids $Met_1$-$Thr_{651}$ of the human GUSB protein (NP_000172), including the 22 amino acid signal peptide, and the 18 amino acid carboxyl terminal propeptide, was cloned by reverse transcription (RT) polymerase chain reaction (PCR) and custom oligodexoynucleotides (ODNs). PCR products were resolved in 1% agarose gel electrophoresis, and the expected major single band of ~2.0 kb corresponding to the human GUSB cDNA was isolated. The cloned human GUSB was inserted into a eukaryotic expression plasmid, and this GUSB expression plasmid was designated pCD-GUSB. The entire expression cassette of the plasmid was confirmed by bi-directional DNA sequencing. Transfection of COS cells in a 6-well format with the pCD-GSUB resulted in high GUSB enzyme activity in the conditioned medium at 7 days (Table 1, Experiment A), which validated the successful engineering of a functional human GUSB cDNA. The GUSB enzyme activity was determined with a fluorometric assay using 4-methylumbelliferyl beta-L-glucuronide (MUGlcU), which is commercially available. This substrate is hydolyzed to 4-methylumbelliferone (4-MU) by GUSB, and the 4-MU is detected fluorometrically with a fluorometer using an emission wavelength of 450 nm and an excitation wavelength of 365 nm. A standard curve was constructed with known amounts of 4-MU. The assay was performed at 37 C with 60 min incubations at pH=4.8, and was terminated by the addition of glycine-carbonate buffer (pH=10.5).

A new pCD-HC-GUSB plasmid expression plasmid was engineered, which expresses the fusion protein wherein the carboxyl terminus of the heavy chain (HC) of the HIR Ab is fused to the amino terminus of human GUSB, minus the 22 amino acid GUSB signal peptide, and minus the 18 amino acid carboxyl terminal GUSB propeptide. The GUSB cDNA was cloned by PCR using the pCD-GUSB as template. The forward PCR primer introduces "CA" nucleotides to maintain the open reading frame and to introduce a Ser-Ser linker between the carboxyl terminus of the CH3 region of the HIR Ab HC and the amino terminus of the GUSB minus the 22 amino acid signal peptide of the enzyme. The GUSB reverse PCR primer introduces a stop codon, "TGA," immediately after the terminal Thr of the mature human GUSB protein. DNA sequencing of the expression cassette of the pCD-HC-GUSB encompassed 4,321 nucleotides (nt), including a 714 nt cytomegalovirus (CMV) promoter, a 9 nt Kozak site (GCCGCCACC), a 3,228 nt HC-GUSB fusion protein open reading frame, and a 370 nt bovine growth hormone (BGH) transcription termination sequence. The plasmid encoded for a 1,075 amino acid protein, comprised of a 19 amino acid IgG signal peptide, the 443 amino acid HIRMAb HC, a 2 amino acid linker (Ser-Ser), and the 611 amino acid human GUSB minus the enzyme signal peptide and carboxyl terminal propeptide. The GUSB sequence was 100% identical to $Leu^{23}$-$Thr^{633}$ of human GUSB (NP_000172). The predicted molecular weight of the heavy chain fusion protein, minus glycosylation, is 119,306 Da, with a predicted isoelectric point (pI) of 7.83.

COS cells were plated in 6-well cluster dishes, and were dual transfected with pCD-LC and pCD-HC-GUSB, where pCD-LC is the expression plasmid encoding the light chain (LC) of the chimeric HIR Ab. Transfection was performed using Lipofectamine 2000, with a ratio of 1:2.5, ug DNA:uL Lipofectamine 2000, and conditioned serum free medium was collected at 3 and 7 days. However, there was no specific increase in GUSB enzyme activity following dual transfection of COS cells with the pCD-HC-GUSB and pCD-LC expression plasmids (Table 1, Experiment B). However, the low GUSB activity in the medium could be attributed to the low secretion of the HIRMAb-GUSB fusion protein, as the medium IgG was only 23±2 ng/mL, as determined by a human IgG-specific ELISA. Therefore, COS cell transfection was scaled up to 10×T500 plates, and the HIRMAb-GUSB fusion protein was purified by protein A affinity chromatography. IgG Western blotting demonstrated the expected increase in size of the fusion protein heavy chain. However, the GUSB enzyme activity of the HIRMAb-GUSB fusion protein was low at 6.1±0.1 nmol/hr/ug protein. In contrast, the specific activity of human recombinant GUSB is 2,000 nmol/hr/ug protein [Sands et al (1994) Enzyme replacement therapy for murine mucopolysaccharidosis type VII. *J Clin Invest* 93, 2324-2331]. These results demonstrated the GUSB enzyme activity of the HIR Ab-GUSB fusion protein was >95% lost following fusion of the GUSB to the carboxyl terminus of the HC of the HIR Ab. The affinity of HIR Ab-GUSB fusion protein binding to the extracellular domain (ECD) of the HIR was examined with an ELISA. CHO cells permanently transfected with the HIR ECD were grown in serum free media (SFM), and the HIR ECD was purified with a wheat germ agglutinin affinity column. The HIR ECD was plated on 96-well dishes and the binding of the HIR Ab, and the HIR Ab-GUSB fusion protein to the HIR ECD was detected with a biotinylated goat anti-human IgG (H+L) secondary antibody, followed by avidin and biotinylated peroxidase. The concentration of protein that gave 50% maximal binding, $ED_{50}$, was determined with a non-linear regression analysis. The HIR receptor assay showed there was no decrease in affinity for the HIR following fusion of the 611 amino acid GUSB to the carboxyl terminus of the HIRMAb heavy chain. The ED50 of the HIR Ab binding to the HIR ECD was 0.77±0.10 nM and the ED50 of binding of the HIR Ab-GUSB fusion protein was 0.81±0.04 nM.

In summary, fusion of the GUSB to the carboxyl terminus of the HIR Ab HC resulted in no loss in affinity of binding of the fusion protein to the HIR. However, the GUSB enzyme activity of the fusion protein was decreased by >95%.

In an effort to successfully produce a fusion protein of the HIR Ab and GUSB, a new approach was undertaken, in which the carboxyl terminus of the mature human GUSB, including the GUSB signal peptide, was fused to the amino terminus of the HC of the HIR Ab. This fusion protein was designated GUSB-HIR Ab. The first step was to engineer a new expression plasmid encoding this new fusion protein, and this plasmid was designated pCD-GUSB-HC. The pCD-GUSB-HC plasmid expresses the fusion protein wherein the amino terminus of the heavy chain (HC) of the HIRMAb, minus its 19 amino acid signal peptide, is fused to the carboxyl terminus of human GUSB, including the 22 amino acid GUSB signal peptide, but minus the 18 amino acid carboxyl terminal GUSB propeptide. The pCD-GUSB vector was used as template for PCR amplification of the GUSB cDNA expressing a GUSB protein that contained the 22 amino acid GUSB signal peptide, but lacking the 18 amino acid propeptide at the GUSB carboxyl terminus. The GUSB 18 amino acid carboxyl terminal propeptide in pCD-GUSB was deleted by site-directed mutagenesis (SDM). The latter created an AfeI site on the 3'-flanking region of the $Thr^{633}$ residue of GUSB, and it was designated pCD-GUSB-AfeI. The carboxyl terminal propeptide was then deleted with AfeI and HindIII (located on the 3'-non coding region of GUSB). The HIRMAb HC open reading frame, minus the 19 amino acid IgG signal peptide and including the HIRMAb HC stop codon, was generated by PCR using the HIRMAb HC cDNA as template. The PCR generated HIRMAb HC cDNA was inserted at the AfeI-HindIII sites of pCD-GUSB-AfeI to form the pCD-GUSB-HC. A Ser-Ser linker between the carboxyl terminus of GUSB and amino terminus of the HIRMAb HC was introduced within the AfeI site by the PCR primer used for the cloning of the HIRMAb HC cDNA. DNA sequencing of the pCD-GUSB-HC expression cassette showed the plasmid expressed 1,078 amino acid protein, comprised of a 22 amino acid GUSB signal peptide, the 611 amino acid GUSB, a 2 amino acid linker (Ser-Ser), and the 443 amino acid HIRMAb HC. The GUSB sequence was 100% identical to $Met^1$-$Thr^{633}$ of human GUSB (NP_000172).

Dual transfection of COS cells in a 6-well format with the pCD-LC and pCD-GUSB-HC expression plasmids resulted in higher GUSB enzyme activity in the conditioned medium at 7 days, as compared to dual transfection with the pCD-LC and pCD-HC-GUSB plasmids (Table 1, Experiment C). However, the GUSB-HIRMAb fusion protein was also secreted poorly by the COS cells, as the medium human IgG concentration in the 7 day conditioned medium was only 13±2 ng/mL, as determined by ELISA. COS cell transfection was scaled up to 10×T500 plates, and the GUSB-HIRMAb fusion protein was purified by protein A affinity chromatography. SDS-PAGE demonstrated the expected increase in size of the fusion protein heavy chain. The GUSB enzyme activity of the purified GUSB-HIRMAb fusion protein was high at 226±8 nmol/hr/ug protein, which is 37-fold higher than the specific GUSB enzyme activity of the HIRMAb-GUSB fusion protein. However, the HIR receptor assay showed there was a marked decrease in affinity for the HIR following fusion of the GUSB to the amino terminus of the HIRMAb heavy chain, which resulted in a 95% reduction in receptor binding affinity. The ED50 of the HIR Ab binding to the HIR ECD was 0.25±0.03 nM and the ED50 of binding of the HIR Ab-GUSB fusion protein was 4.8±0.4 nM.

In summary, fusion of the GUSB to the amino terminus of the HIR Ab HC resulted in retention of GUSB enzyme activity of the fusion protein, but caused a 95% reduction in binding of the GUSB-HIR Ab fusion protein to the HIR. In contrast, fusion of the GUSB to the carboxyl terminus of the HIR Ab HC resulted in no loss in affinity of binding of the HIR Ab-GUSB fusion protein to the HIR. However, the GUSB enzyme activity of this fusion protein was decreased by >95%.

Example 2. Construction of Human HIR Ab Heavy Chain-IDS Fusion Protein Expression Vector The lysosomal enzyme mutated in MPS-II, also called Hunter's syndrome, is iduronate 2-sulfatase (IDS). MPS-II results in accumulation of glycosoaminoglycans in the brain. Enzyme replacement therapy of MPS-II would likely not be effective for treatment of the brain because the IDS enzyme does not cross the BBB. IDS was fused to the HIR Ab in order to develop a bifunctional molecule capable of both crossing the BBB and exhibiting enzymatic activity.

It was unclear whether the enzymatic activity of the IDS would be retained when it was fused to the HIR Ab. This is because IDS undergoes a post-translational modification within the endoplasmic reticulum, and it was not known whether that process would be compromised when IDS was fused to HIR Ab. IDS is a member of a family of sulfatases, wherein the activity of the enzyme is activated following the conversion of Cys-59 to a formylglycine residue by a sulfatase modifying factor in the endoplasmic reticulum [Zito et al, Sulphatase activities are regulated by the interaction of sulphatase-modifying factor 1 with SUMF2. *EMBO Rep* 6 (2005) 655-660]. Without this conversion of the internal cysteine into a formylglycine residue, the enzyme has no activity. If the IDS was fused to the carboxyl terminus of the HC of the HIR Ab, e.g. in an effort to retain high affinity binding of the fusion protein to the HIR, then the IgG heavy chain would fold into the 3-dimensional structure following translation within the host cell, followed by folding of the IDS part of the fusion protein. It was uncertain as to whether the IDS part of the HIR Ab HC-IDS fusion protein would fold into a 3-dimensional structure that would be recognized by, and activated by, the IDS-modifying factors in the endoplasmic reticulum, resulting in expression of full IDS enzyme activity in the HIR Ab-IDS fusion protein.

Figure 8:
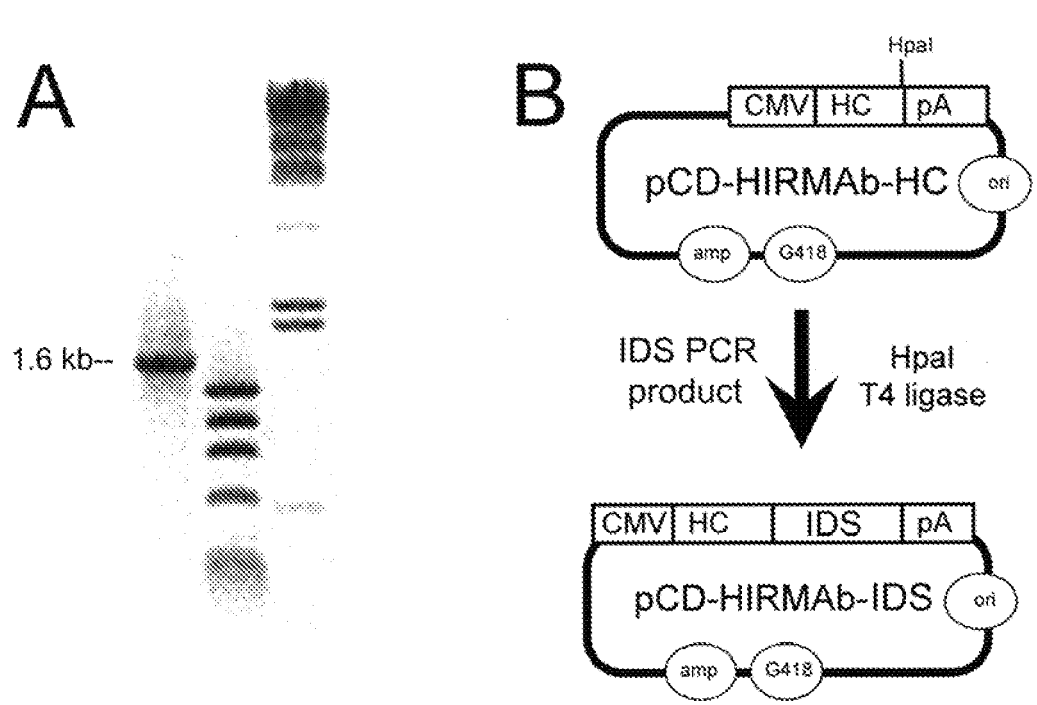
FIG. 8. (A) Ethidium bromide stain of agarose gel of human IDS cDNA (lane 1), which was produced by PCR from human liver cDNA, and IDS-specific primers (Table 2). Lanes 2 and 3: PhiX174 HaeIII digested DNA standard, and Lambda HindIII digested DNA standard. (B) The heavy chain of the HIRMAb-IDS fusion protein is expressed by the pCD-HIRMAb-IDS plasmid, which is generated by subcloning the IDS cDNA into the HpaI site of the pCD-HIRMAb-HC plasmid.

The human IDS cDNA, encoding $Ser^{26}$-$Pro^{550}$, minus the 25 amino acid signal peptide (Genbank NP_000193) was produced by reverse transcription and PCR, starting with human liver polyA+RNA (Clontech). Human liver cDNA was prepared using the SuperScript first-strand synthesis kit (Invitrogen, San Diego, Calif.) and oligodeoxythymidine priming. The IDS cDNA was cloned using 2 μl liver cDNA reverse transcription reaction, 0.2 μM IDS forward and reverse ODN primers (Table 2), 0.2 mM deoxynucleotide-triphosphates and 2.5 U PfuUltra DNA polymerase (Stratagene, San Diego, Calif.) in a 50 μl Pfu buffer (Stratagene). The amplification was performed in a Mastercycler temperature cycler (Eppendorf, Hamburg, Germany) with an initial denaturing step of 95° C. for 2 min followed by 30 cycles of denaturing at 95° C. for 30 sec, annealing at 55° C. for 30 sec and amplification at 72° C. for 1 min. PCR products were resolved in 1% agarose gel electrophoresis, and the expected major single band of ~1.6 kb corresponding to the human IDS cDNA was isolated (FIG. 8A). The cloned human IDS was inserted into the pCD-HIRMAb HC eukaryotic expression plasmid at the HpaI site, and this expression plasmid was designated pCD-HIRMAb-IDS, as outlined in FIG. 8B; the pCD-HIRMAb-HC expression plasmid encodes the heavy chain (HC) of the chimeric HIRMAb. The entire expression cassette of the plasmid was confirmed by bi-directional DNA sequencing. The IDS forward PCR primer (SEQ ID NO:11) was a 23-mer coding for the 7 amino acids at the beginning of the mature IDS protein. This primer introduces "CC" nucleotides to maintain the open reading frame and to introduce a Ser-Ser linker between the carboxyl terminus of the CH3 region of the HIRMAb HC and the amino terminus of the IDS minus the 25 amino acid signal peptide of the enzyme. The IDS reverse PCR primer (SEQ ID NO:12) was a 27-mer complementary to the end of the IDS cDNA including the stop codon, "TGA," immediately after the terminal Pro of the mature human IDS protein. The fusion of the IDS monomer to the carboxyl terminus of each HC is depicted in FIG. 6. The entire expression cassette of the plasmid was confirmed by sequencing both strands.

DNA sequencing of the expression cassette of the pCD-HIRMAb-IDS plasmid encompassed 4,063 nucleotides (nt), including a 714 nt cytomegalovirus promoter, a 9 nt full Kozak site (GCCGCCACC), a 2,970 nt HIRMAb HC-IDS fusion protein open reading frame, and a 370 nt bovine growth hormone polyA sequence. The plasmid encoded for a 989 amino acid protein (SEQ ID NO:10), comprised of a 19 amino acid IgG signal peptide, the 443 amino acid HIRMAb HC, a 2 amino acid linker (Ser-Ser), and the 525 amino acid human IDS minus the enzyme signal peptide. The predicted molecular weight of the heavy chain fusion protein, minus glycosylation, is 108,029 Da, with a predicted isoelectric point (pI) of 6.03.

Example 3. Expression Analysis of HIR Ab-IDS Fusion Protein in COS Cells

COS cells were plated in 6-well cluster dishes, and were dually transfected with the pCD-HC-IDS, and pCD-LC, where pCD-LC is the expression plasmid encoding the light chain (LC) of the chimeric HIRMAb, which is also used by the HIR Ab-IDS fusion protein. Expression of the fusion protein was screened with an ELISA specific for human IgG. For production of larger amounts of fusion protein, COS cells were transfected in 10×T500 flasks. The 3 day and 7 day medium was pooled, and the 2 L of serum free conditioned medium was concentrated to 400 mL with tangential flow filtration (Millipore) followed by purification with protein A affinity chromatography.

Figure 9:
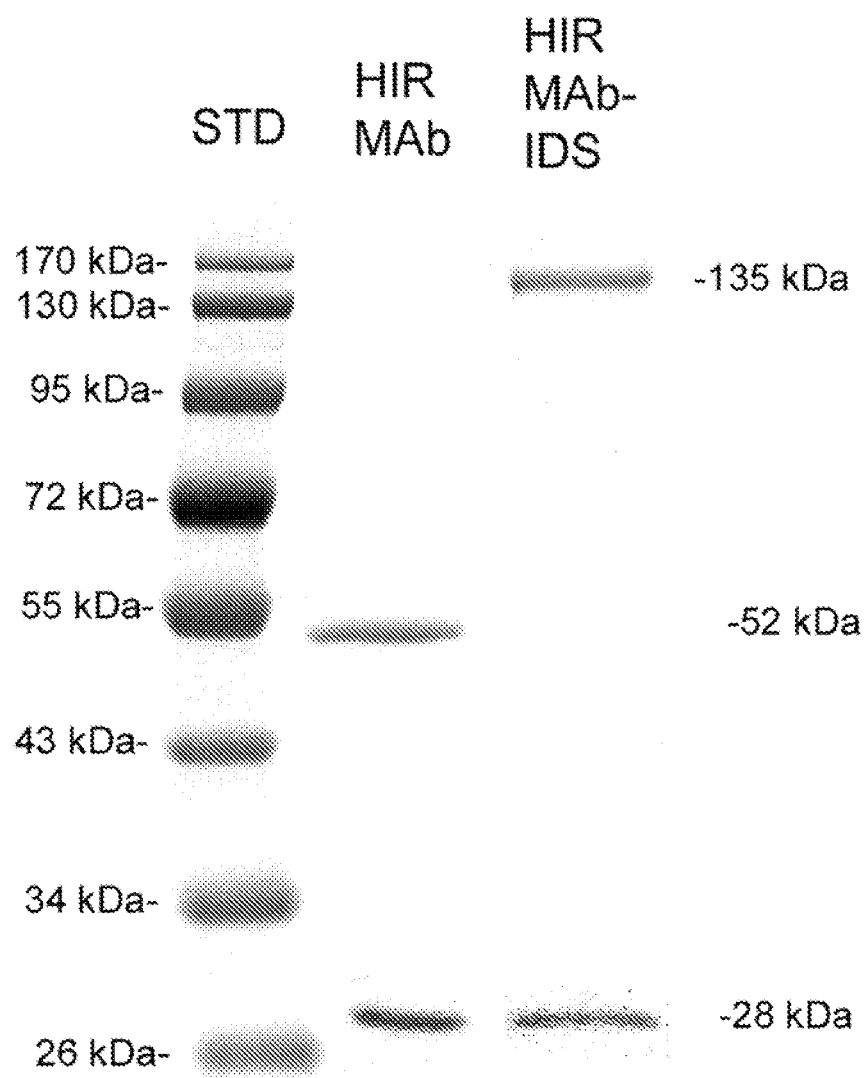
FIG. 9. SDS-PAGE of molecular weight standards (STD), the purified HIRMAb, and the purified HIRMAb-IDS fusion protein.

The purity of protein A purified fusion protein produced by COS cells was evaluated with 12% sodium dodecyl sulfate polyacrylamide gel electrophoresis (SDSPAGE) with 5% β-mercaptoethanol, and shown to have a homogeneity comparable to the purified HIR Ab (FIG. 9) Immunoreactivity was tested with a goat antibody to human IDS, or a primary goat antiserum against human IgG heavy and light chains.

Figure 10:
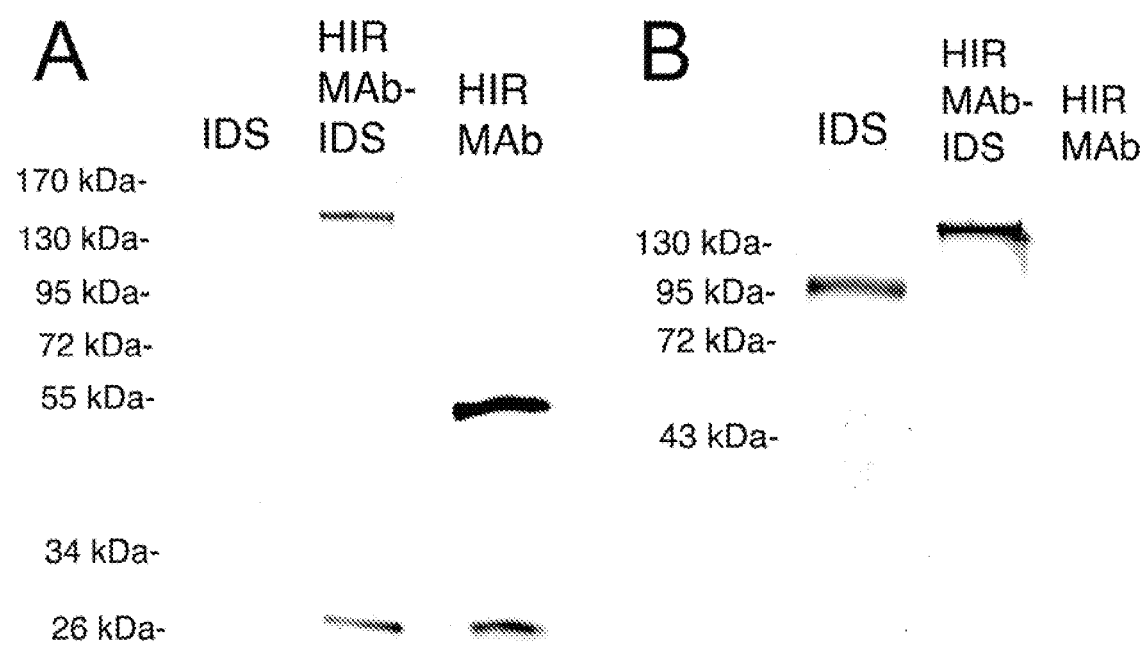
FIG. 10. Western blot with either anti-human (h) IgG primary antibody (A) or anti-human IDS primary antiserum (B). The immunoreactivity of the HIRMAb-IDS fusion protein is compared to the chimeric HIRMAb and recombinant human IDS. Both the HIRMAb-IDS fusion protein and the HIRMAb have identical light chains on the anti-hIgG Western. The HIRMAb-IDS fusion heavy chain reacts with both the anti-hIgG and the anti-human IDS antibody, whereas the HIRMAb heavy chain only reacts with the anti-hIgG antibody. The size of the HIRMAb-IDS fusion heavy chain, 130 kDa, is about 80 kDa larger than the size of the heavy chain of the HIRMAb, owing to the fusion of the 80 kDa IDS to the 50 kDa HIRMAb heavy chain.

On Western blotting of the purified HIR Ab-IDS fusion protein, the anti-human IgG antibody reacts with a 135 kDa HC for the fusion protein, and a 50 kDa HC for the chimeric HIR Ab, and the difference in size, 85 kDa, is due to the fusion of IDS (FIG. 10A). The anti-human IgG antibody reacts equally with the light chain of either the HIR Ab-IDS fusion protein or the HIR Ab, since both proteins are comprised of the same light chain. The anti-IDS antibody reacts with the 135 kDa HC of the fusion protein, but not with the HC of the chimeric HIR Ab (FIG. 10B).

Example 4. Analysis of HIR Binding and IDS Activity

Figure 11:
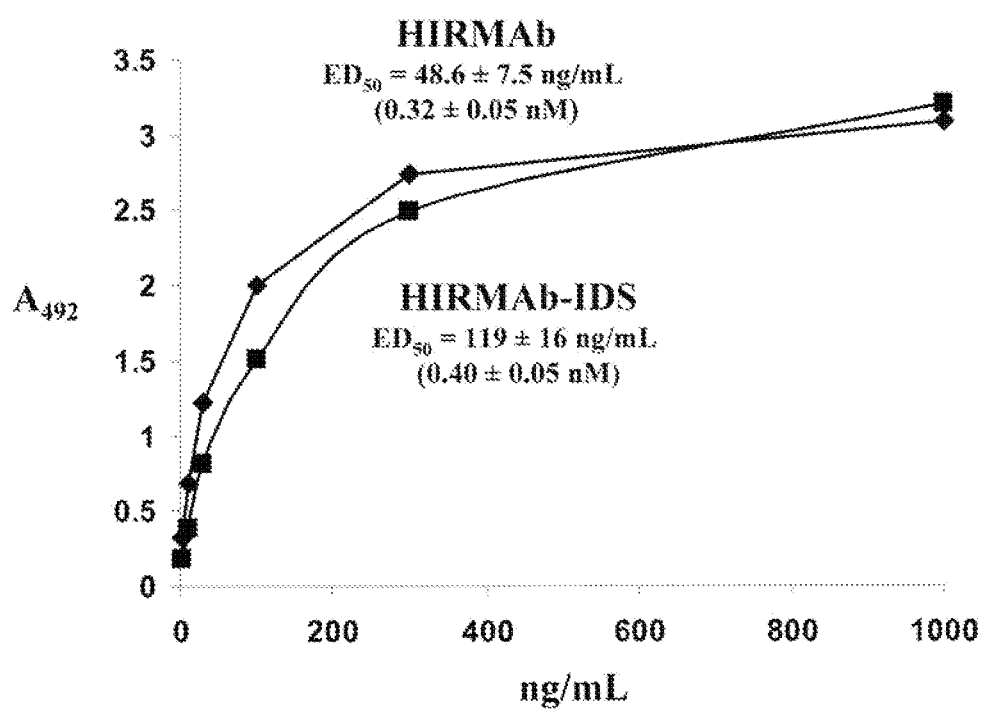
FIG. 11. Binding of either the chimeric HIRMAb or the HIRMAb-IDS fusion protein to the HIR extracellular domain (ECD) is saturable. The $ED_{50}$ of HIRMAb-IDS binding to the HIR ECD is comparable to the $ED_{50}$ of the binding of the chimeric HIRMAb.

The affinity of the fusion protein for the HIR extracellular domain (ECD) was determined with an ELISA. CHO cells permanently transfected with the HIR ECD were grown in serum free media (SFM), and the HIR ECD was purified with a wheat germ agglutinin affinity column, as previously described in Coloma et al. (2000) *Pharm Res*, 17:266-274. The HIR ECD was plated on Nunc-Maxisorb 96 well dishes and the binding of the HIR Ab, or the HIR Ab-IDS fusion protein, to the HIR ECD was detected with a biotinylated goat anti-human IgG (H+L) secondary antibody, followed by avidin and biotinylated peroxidase (Vector Labs, Burlingame, Calif.). The concentration of either HIR Ab or HIR Ab-IDS fusion protein that gave 50% maximal binding was determined with a non-linear regression analysis. As shown in FIG. 11 there was comparable binding of either the chimeric HIR Ab or the HIR Ab-IDS fusion protein for the HIR ECD with ED50 of 0.32±0.05 nM and 0.40±0.05 nM, respectively.

The IDS enzyme activity was determined with a fluorometric assay using 4-methylumbelliferyl a-L-iduronide-2-sulphate (4-MUS), which was purchased from Moscerdam Substrates (Rotterdam, The Netherlands). This substrate is hydrolyzed by IDS to 4-methylumbelliferyl a-L-iduronide (MUBI), and the MUBI is hydrolyzed by iduronidase (IDUA, Aldurazyme, Genzyme, Boston, Mass.) to 4-methylumbelliferone (4-MU), which is detected fluorometrically with a Farrand filter fluorometer using an emission wavelength of 450 nm and an excitation wavelength of 365 nm. A standard curve was constructed with known amounts of 4-MU (Sigma-Aldrich, St. Louis, Mo.). The assay was performed by incubation at 37 C at pH=4.5 for 4 hours in McIlvaine's buffer, followed by the addition of 12 ug of IDUA and an additional 24 incubation at 37 C. The incubation was terminated by the addition of 0.2 mL of 0.5 M sodium carbonate (pH=10.3). One unit=1 nmol/hr. The 2-step enzymatic fluorometric assay is outlined in FIG. 12A. The fluorometric units were proportional to the mass of purified HIRMAb-IDS fusion protein and the enzymatic activity of the fusion protein was 51±7 nmol/hr/ug protein (FIG. 12B), which is comparable to the IDS enzyme activity reported for human recombinant Idursulfase (G. Zareba, Idursulfase in Hunter syndrome treatment. *Drugs Today* (Barc) 43 (2007) 759-767).

Example 5. HIR Ab-IDS Fusion Protein Uptake and Biological Activity in MPS Type II Fibroblasts Type II MPS Hunter fibroblasts (GM000298) and healthy human fibroblasts (GM000497) were obtained from the Coriell Institute for Medical Research (Camden, New Jersey), and grown in 6-well cluster dishes to confluency. The medium was aspirated, wells washed with phosphate buffered saline (PBS), and incubated with 1 mL of Dulbecco's modified Eagle medium without serum, along with a range of concentrations of the HIRMAb-IDS fusion protein, for 2 hr at 37 C. The medium was aspirated, and the wells were washed extensively (1 mL/well, 5 washes) with PBS, and the monolayer was extracted in 0.3 mL/well of lysis buffer (5 mM sodium formate, 0.2% Triton X-100, pH=4.0), followed by 4 freeze/thaw cycles, and microfuged 10 min 4° C. The supernatant was removed for IDS enzyme activity and bicinchoninic acid protein (BCA) assay. The uptake of the fusion protein was expressed as nmol/hr of IDS enzyme activity per mg cell protein.

Figure 13:
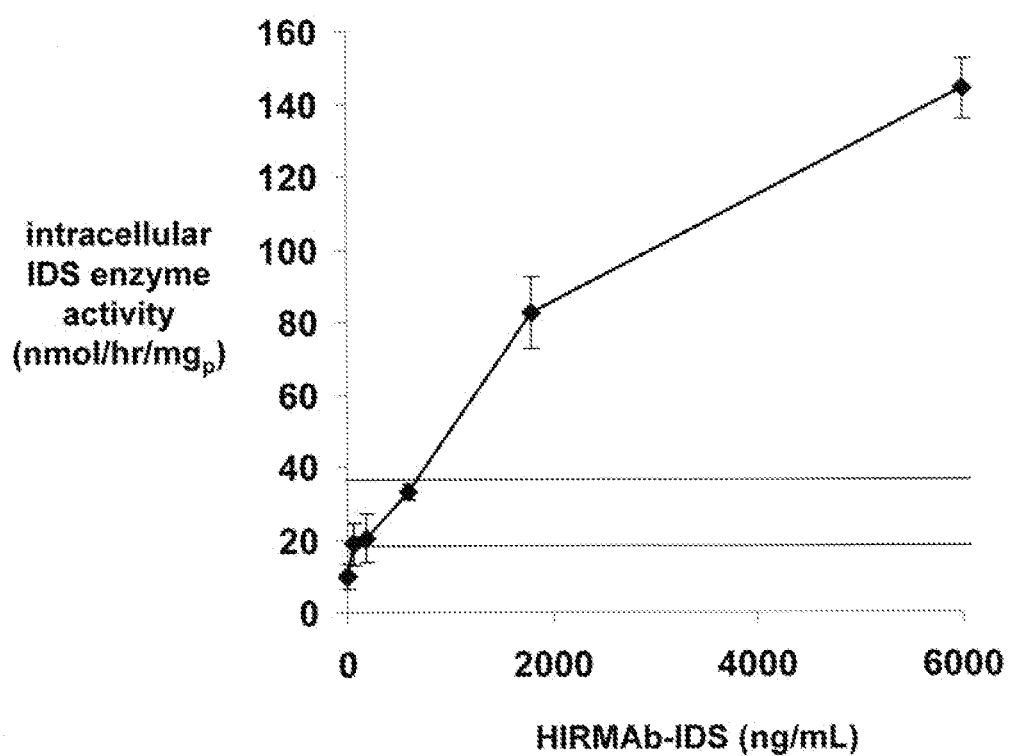
FIG. 13. Intracellular IDS enzyme activity is increased in Hunter fibroblasts in proportion to the concentration of medium HIRMAb-IDS fusion protein. Data are mean±SE (n=3 dishes/point). The horizontal bar is the IDS enzyme activity in healthy human fibroblasts (mean±SD).

The HIRMAb-IDS fusion protein was taken up by MPS Type II fibroblasts (FIG. 13). The basal IDS activity in these cells without treatment is very low, <10 nmol/hr/mg$_p$. The intracellular IDS enzyme activity increases in proportion to the concentration of medium HIRMAb-IDS (FIG. 13). The normal IDS enzymatic activity in healthy human fibroblasts is shown by the horizontal bar in FIG. 13.

The effect of the HIRMAb-IDS fusion protein on cell glycosoaminoglycan (GAG) accumulation was assessed with a $^{35}$S incorporation assay. Type II MPS or healthy human fibroblasts were plated in 6-well cluster dishes at 250,000 cells/well and grown for 4 days in DMEM with 10% fetal bovine serum. The medium was discarded, the wells were washed with PBS, and 1 mL/well of low sulfate F12 medium with 10% dialyzed fetal bovine serum was added, along with 5 mM CaCl2, the HIRMAb-IDS fusion protein (0.3 ug/mL), and 10 uCi/mL of $^{35}$S-sodium sulfate (Perkin Elmer, Boston, Mass.). Following a 24 hr incubation at 37 C, the medium was aspirated, the wells were washed with cold PBS (1 mL, 5 washes), and the cells were lysed with 0.4 mL/well of 1 N NaOH. The lysate was heated 60° C. 60 min to solubilize protein, an aliquot was removed for BCA protein assay, and the sample was counted for radioactivity with a Perkin Elmer Tri-Carb 2100 liquid scintillation counter. The data were expressed as $^{35}$S counts per minute (CPM) per ug protein. The percent normalization of GAG accumulation was computed from [(A−B/(A−C)]× 100, where A=the $^{35}$S radioactivity incorporated in untreated Hunter fibroblasts, B=the $^{35}$S radioactivity incorporated in Hunter fibroblasts treated with the HIRMAb-IDS fusion protein, and C=the $^{35}$S radioactivity incorporated in healthy human fibroblasts.

Figure 14:
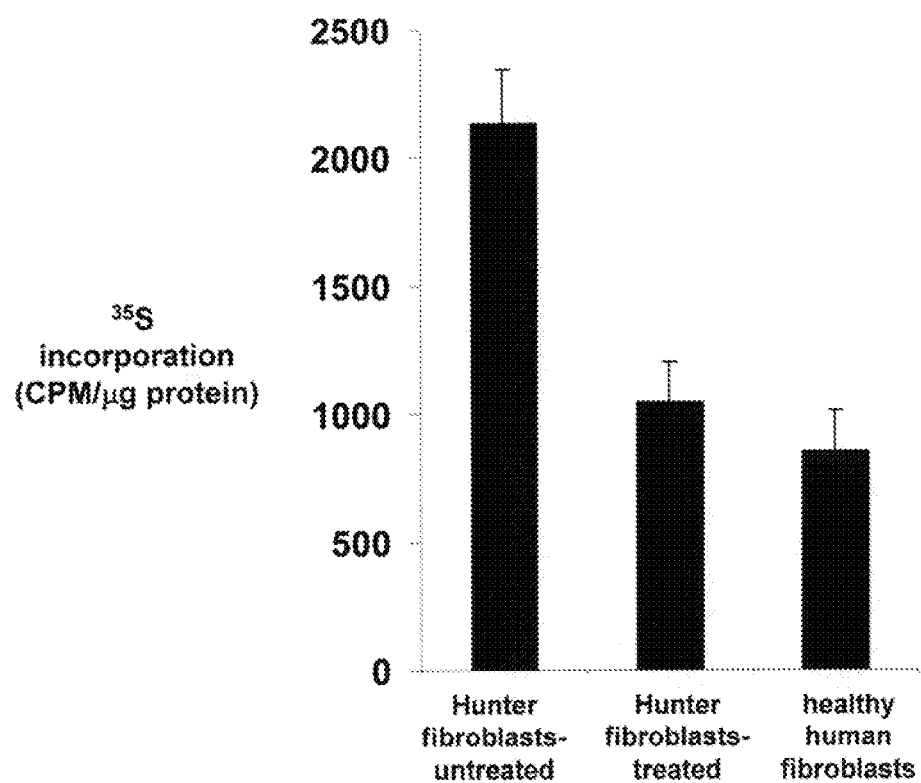
FIG. 14. Reversal of glycosaminoglycan (GAG) accumulation in Hunter fibroblasts with a single treatment of 0.3 ug/mL of HIRMAb-IDS fusion protein in the medium. There is an 84% reduction in GAG accumulation, as compared to the $^{35}S$ incorporation in healthy human fibroblasts (p<0.0005). Data are mean±SE (n=4 dishes/point).

The Hunter fibroblasts, with or without treatment with 0.3 ug/mL HIRMAb-IDS fusion protein in the medium, and the healthy human fibroblasts, were incubated 24 hrs in the presence of $^{35}$S-sodium sulfate, which is incorporated into intracellular GAGs. Treatment with the HIRMAb-IDS fusion protein reduces GAG accumulation in Hunter fibroblasts by 84% as compared to healthy fibroblasts (p<0.0005) (FIG. 14). The prevention of GAG accumulation in Hunter fibroblasts (FIG. 14) indicates the HIR Ab-IDS fusion antibody was directed to the lysosomal compartment of the cell, where GAG accumulates.

Example 6. Expression Vectors for Permanent Transfection of Host Cell

Figure 15:
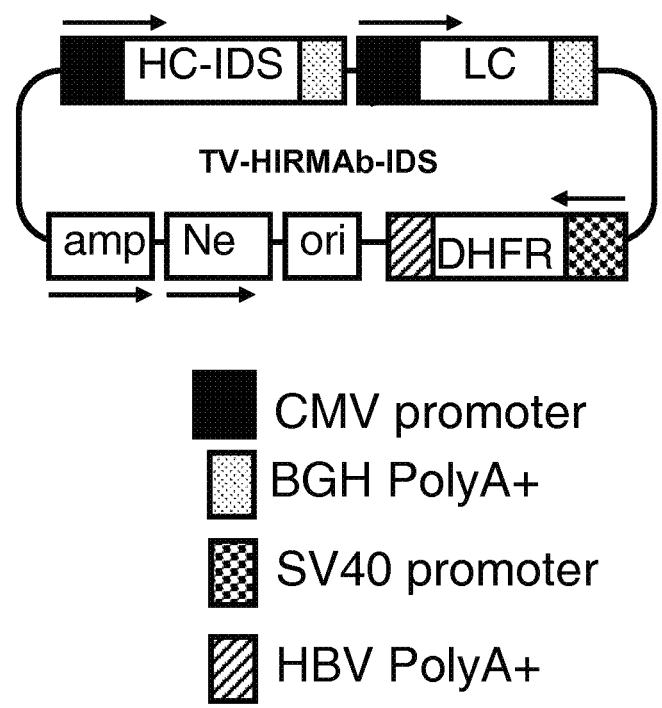
FIG. 15. Genetically engineered tandem vector (TV-HIRMAb-IDS) encoding 4 separate and tandem expression cassettes encoding the heavy chain (HC) fusion gene, the light chain (LC) gene, the DHFR gene, and the neo gene.

The HIRAb-IDS fusion protein is a hetero-tetrameric protein comprised of 2 heavy chains (HC) and 2 light chains (LC) (FIG. 6), wherein the separate HC and LC proteins are produced from separate HC and LC genes. Therefore, in order to insure high production of the entire fusion protein by a permanently transfected host cell, it is necessary to achieve equally high expression of both the HC and the LC within the host cell. In addition, the host cell must be permanently transfected with a marker gene that allows for selective amplification of the host genome around the site of insertion of the transgene. For example, persistent exposure of host cells to a drug such as methotrexate (MTX) will select for clones with high gene expression of the target enzyme, which is dihydrofolate reductase (DHFR). So as to insure equally high expression of the HC fusion gene, the LC gene, and the DHFR gene, the expression cassettes encoding these 3 genes were all placed on a single strand of DNA, called a tandem vector, which is outlined in FIG. 15. The HC fusion gene and the LC gene are 5'-flanked by a cytomegalovirus (CMV)-derived promoter and 5'-flanked by the polyA+ sequence from the bovine growth hormone (BGH) gene. The DHFR gene was 5'-flanked by the SV40 promoter and 3'-flanked by the polyA sequence from the hepatitis B virus (HBV) genome. The TV-HIRMAb-IDS also included the expression cassette encoding neo, the neomycin resistance gene, to enable selection with G418 (FIG. 15)

The engineering of the TV was validated by (a) agarose gel electrophoresis, (b) IgG expression in COS cells, and (c) by bi-directional DNA sequencing.

The nucleotide (nt) sequence encoding the open reading frame of the LC, the HC fusion protein, and the DHFR is given in SEQ ID NO:13, SEQ ID NO:14, and SEQ ID NO:15, respectively (FIGS. 16, 17, 18 respectively). The amino acid (AA) sequences encoded by the HC fusion gene, the LC gene, and the DHFR gene on the tandem vector are given in SEQ ID NO:10, SEQ ID NO:16, and SEQ ID NO:17, respectively (FIGS. 5, 19, and 20, respectively).

Example 7. Permanent Transfection of Chinese Hamster Ovary Cells with TV-HIRMAb-IDS Chinese hamster ovary (CHO) cells were grown in serum free HyQ SFM4CHO utility medium (HyClone), containing 1×HT supplement (hypoxanthine and thymidine). CHO cells ($5 \times 10^6$ viable cells) were electroporated with 5 μg PvuI-linearized TV-HIRMAb-IDS plasmid DNA. The cell-DNA suspension was then incubated for 10 min on ice. Cells were electroporated with BioRad pre-set protocol for CHO cells, i.e. square wave with pulse of 15 msec and 160 volts. After electroporation, cells were incubated for 10 min on ice. The cell suspension was transferred to 50 ml culture medium and plated at 125 μl per well in 4×96-well plates (10,000 cells per well). A total of 10 electroporations and 4,000 wells were performed per study.

Following electroporation (EP), the CHO cells were placed in the incubator at 37 C and 8% CO2. Owing to the presence of the neo gene in the TV, transfected cell lines were initially selected with G418. The TV-HIRMAb-IDS also contains the gene for DHFR (FIG. 15), so the transfected cells were also selected with 20 nM methotrexate (MTX) and HT deficient medium. Once visible colonies were detected at about 21 days after EP, the conditioned medium was sampled for human IgG by ELISA. Wells with high human IgG signals in the ELISA were transferred from the 96-well plate to a 24-well plate with 1 mL of HyQ SFM4CHO-Utility. The 24-well plates were returned to the incubator at 37 C and 8% CO2. The following week IgG ELISA was performed on the clones in the 24-well plates. This was repeated through the 6-well plates to T75 flasks and finally to 60 mL and 125 mL square plastic bottles on an orbital shaker. At this stage, the final MTX concentration was 80 nM, and the medium IgG concentration, which was a measure of HIRMAb-IDS fusion protein in the medium is >10 mg/L at a cell density of $10^6$/mL.

Clones selected for dilutional cloning (DC) were removed from the orbital shaker in the incubator and transferred to the sterile hood. The cells were diluted to 500 mL in F-12K medium with 5% dialyzed fetal bovine serum (d-FBS) and Penicillin/Streptomycin, and the final dilution is 8 cells per mL, so that 4,000 wells in 40×96-well plates can be plated at a cell density of 1 cell per well (CPW). Once the cell suspension was prepared, within the sterile hood, a 125 uL aliquot was dispensed into each well of a 96-well plate using an 8-channel pipettor or a precision pipettor system. The plates were returned to the incubator at 37 C and 8% CO2. The cells diluted to 1 cell/well cannot survive without serum. On day 6 or 7, DC plates were removed from the incubator and transferred to the sterile hood where 125 μl of F-12K medium with 5% dialyzed fetal bovine serum (d-FBS) was added to each well. This selection media now contained 5% d-FBS, 30 nM MTX and 0.25 mg/mL Geneticin. On day 21 after the initial 1 CPW plating, aliquots from each of the 4,000 wells were removed for human IgG ELISA, using robotics equipment. DC plates were removed from the incubator and transferred to the sterile hood, where 100 µl of media was removed per well of the 96-well plate and transferred into a new, sterile sample 96-well plate using an 8-channel pipettor or the precision pipettor system.

On day 20 after the initial 1 CPW plating, 40×96-well Immunoassay plates were plated with 100 uL of 1 µg/mL solution of Primary antibody, a mouse anti-human IgG in 0.1M NaHCO3. Plates are incubated overnight in the 4 C refrigerator. The following day, the ELISA plates were washed with 1× TBST 5 times, and 100 uL of 1 ug/mL solution of secondary antibody and blocking buffer were added. Plates are washed with 1× TBST 5 times. 100 uL of 1 mg/mL of 4-nitrophenyl phosphate di(2-amino-2-ethyl-1, 3-propanediol) salt in 0.1M glycine buffer are added to the 96-well immunoassay plates. Plates were read on a microplate reader. The assay produced IgG output data for 4,000 wells/experiment. The highest producing 24-48 wells were selected for further propagation.

The highest producing 24-well plates from the 1 CPW DC were transferred to the sterile hood and gradually subcloned through 6-well dishes, T75 flasks, and 125 mL square plastic bottles on an orbital shaker. During this process the serum was reduced to zero, at the final stage of centrifugation of the cells and resuspension in SFM.

The above procedures were repeated with a second round of dilutional cloning, at 0.5 cells/well (CPW). At this stage, approximately 40% of the wells showed any cell growth, and all wells showing growth also secreted human IgG. These results confirmed that on average only 1 cell is plated per well with these procedures, and that the CHO cell line originates from a single cell.

Figure 12:
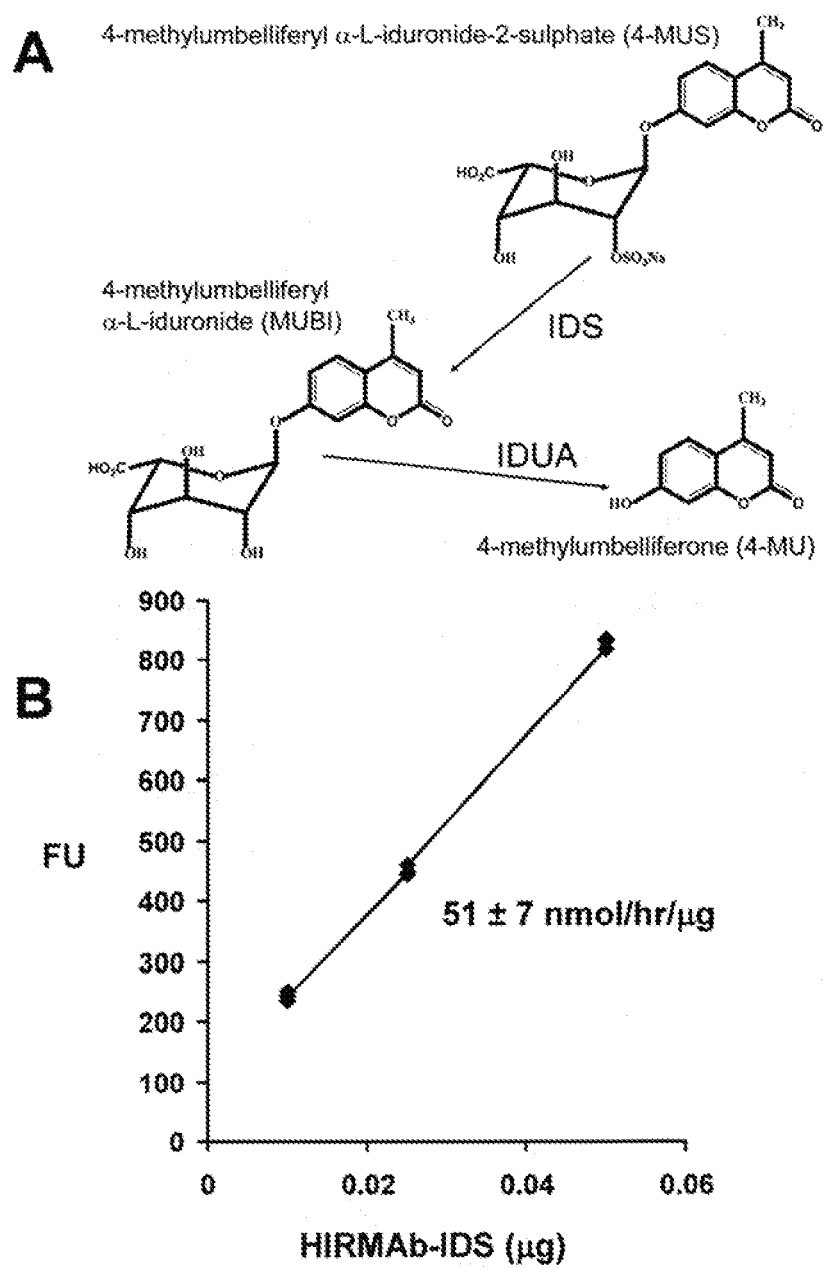
FIG. 12. (A) Substrate (4-MUS), intermediate (MUBI), and product (4-MU) of the 2-step enzymatic fluorometric assay of IDS enzyme activity. (B) The fluorometric units (FU) are proportional to the mass of purified HIRMAb-IDS fusion protein, and the average enzyme specific activity of the fusion protein is 51±7 nmol/hr/ug protein, which is equivalent to 51 units/ug protein, or 51,000 units/mg protein.

The HIR Ab-IDS fusion protein was secreted to the medium by the stably transfected CHO cells in high amounts at medium concentrations of 10-20 mg/L at a cell density of 1-2 million cells/mL. The CHO-derived HIRMAb was purified by protein A affinity chromatography, and the patterns of migration of the fusion protein on SDS-PAGE and on IgG or IDS Western blotting was identical to that shown in FIGS. 9 and 10 for the HIR Ab-IDS fusion protein produced by transiently transfected COS cells. The CHO-derived fusion protein migrated as a single peak, without aggregation, on size exclusion HPLC. The CHO-derived fusion protein retained high affinity binding to the HIR. Using the same methods as performed for the study in FIG. 11, the CHO-derived fusion protein was shown to have a high affinity for binding to the HIR, with an EC50 of 0.36±0.04 nM, which was not significantly different from the EC50, 0.41±0.09 nM, for the HIR Ab without the fused IDS. The CHO-derived HIR Ab-IDS fusion protein retained high IDS enzyme activity despite fusion of the IDS to the HIR Ab. Using the IDS enzyme assay described in FIG. 12, the IDS enzyme specific activity of the CHO-derived HIR Ab-IDS fusion protein is 115±7 nmol/ug protein/hour, which is even higher than the IDS specific activity of the COS-derived fusion protein (FIG. 12B).

The high IDS enzyme activity of the CHO-derived HIR Ab-IDS fusion protein is surprising, because IDS is a member of a family of sulfatases that requires a specific post-translational modification for expression of IDS enzyme activity. The activity of the IDS enzyme is activated following the conversion of Cys-59 to a formylglycine residue by a sulfatase modifying factor type 1 (SUMF1), which is also called the formylglycine generating enzyme (FGE). The retention of IDS enzyme activity in the HIRMAb-IDS fusion protein produced by the stably transfected CHO cells indicates the IDS enzyme is activated within the host cell despite fusion to the HIRMAb heavy chain.

Example 8. Removal of IDS Propeptide From Fusion Protein

The first 8 amino acids of IDS following the 25 amino acid signal peptide constitute a propeptide (Flomen et al, Determination of the organization of coding sequences within the iduronate sulphate sulphatase (IDS) gene, *Hum. Mol. Genet.* 2, 5-10, 1993), which may be subject to cleavage by endoproteases. Such cleavage could result in the separation of the IDS from the HIR Ab, in which case the IDS could not be carried across the BBB by the HIR Ab Trojan horse. In this event, the IDS cDNA would be re-amplified by PCR using the new forward ODN listed in Table 2 (SEQ ID NO: 18). PCR with the IDS FWD2 ODN and IDS REV ODN listed in Table 2 will amplify an IDS cDNA that encodes for the IDS enzyme minus the 25 amino acid signal peptide, from Met-1 to Gly-25, and minus the 8 amino acid propeptide, from Ser-26 to Thr-33, and beginning with Thr-34 and ending in Pro-550 of the human IDS sequence (NP_000193). The IDS FWD2 ODN has 'CC' on the 5'-end to maintain the open reading frame with the carboxyl terminus of the CH3 region of the HC of the HIR Ab, and the Ser-Ser linker placed between the carboxyl terminus of the HIR Ab HC and the amino terminus of the IDS.

Example 9 Amino Acid Linker Joining the IDS and the Targeting Antibody

The mature human IDS is fused to the carboxyl terminus of the HC of the HIR Ab with a 2-amino acid linker, Ser-Ser (underlined in FIG. 5). Any number of variations of linkers are used as substitutions for the Ser-Ser linker. The 2-amino acid linker may be retained, but the amino acid sequence is changed to alternative amino acids, such as Gly-Gly, or Ser-Gly, or Ala-Ser, or any number of combinations of the 20 natural amino acids. Or, the linker is reduced to a single amino acid, or zero amino acids. In the case of a zero amino acid linker, the amino terminus of the IDS is fused directly to the carboxyl terminus of the HC of the HIR Ab. Alternatively, the length of the linker is expanded to 3,4,5,6,7,8, 9,10,11,12,13,14,15 amino acids. Such linkers are well known in the art, as there are multiple publicly available programs for determining optimal amino acid linkers in the engineering of fusion proteins. A frequently used linker includes various combinations of Gly and Ser in repeating sequences, such as $(Gly_4Ser)_3$ (SEQ ID NO: 19), or other variations.

Example 10. (Prophetic Example) Receptor-Mediated Delivery of IDS to the Human Brain Mucopolysaccharidosis (MPS) Type II (MPS-II), or Hunter's syndrome, is a lysosomal storage disorder caused by defects in the gene encoding the lysosomal enzyme, iduronate-2-sulfatase (IDS). MPS-II is treated with recombinant human IDS in enzyme replacement therapy (ERT) [Muenzer, et al, A phase II/III clinical study of enzyme replacement therapy with idurosulfase in mucopolysaccharidosis II (Hunter syndrome). *Genet. Med.* 8 (2006) 465-

473]. However, many cases of MPS-II affect the central nervous system [Al Sawaf, et al, Neurological findings in Hunter disease: pathology and possible therapeutic effects reviewed. *J Inherit Metab Dis* 31 (2008) 473-480]. ERT is not effective for the brain, because the IDS does not cross the BBB, and in MPS-II cases that do affect the brain, the use of ERT is considered optional [Wraith, et al, Mucopolysaccharidosis type II (Hunter syndrome): a clinical review and recommendations for treatment in the era of enzyme replacement therapy. *Eur J Pediatr* 167 (2008) 267-77]. It is currently not possible to treat the brain of subjects with MPS-II, and new treatments are needed to prevent the inexorable neurologic deterioration and death associated with MPS-II.

IDS is made to cross the human BBB following the re-engineering of the enzyme as a fusion protein with a BBB molecular Trojan horse such as the HIR Ab (FIG. 6). The brain uptake of the HIR Ab in the Rhesus monkey is about 1% of injected dose (ID) per 100 gram brain [Boado et al. (2007), *Biotechnol Bioeng*, 96(2):381-391.]. The size of the Rhesus monkey brain is approximately 100 grams; therefore, about 1% of the injected dose is distributed to the primate brain. Given a dose of intravenous recombinant HIR Ab-IDS in Hunter's syndrome of about 1.0 mg/kg, then 50 mg of fusion protein would be injected in a 50 kg patient, which is equivalent to $5 \times 10^7$ ng fusion protein. The uptake of the fusion protein by brain, expressed as a % of ID/gram, in the human is expected to be reduced, as compared to the primate, in proportion to body weight. Therefore, the expected brain uptake of the fusion protein in the human brain is about 1% of the injected dose per human brain, or about 1% of the ID per 1000 g human brain. One gram of brain contains about 100 mg brain protein. The brain uptake of the fusion protein is about $10^{-2}$/human brain, or about $10^{-5}$/gram brain, or about $10^{-7}$/mg brain protein. Therefore, the brain concentration of the HIR Ab-IDS fusion protein is about $[(10^{-7}/\text{mg protein}) \times (5 \times 10^7$ ng of fusion protein injected)] or about 5 ng fusion protein per mg brain protein. Given an IDS enzyme specific activity of 115 units/ug fusion protein for the HIR Ab-IDS fusion protein (FIG. 12B), which is 0.12 units/ng of fusion protein, then the IDS activity in brain is about 0.6 units/mg brain protein, where 1 unit=1 nmol/hr. Given $10^5$ mg protein per human brain, the IDS activity delivered to the human brain is expected to be about 60,000 units. The normal IDS enzyme activity in brain is about 2.5 units/mg protein (Tomatsu et al, Murine model of MPS IVA with missense mutation at the active site cysteine conserved among sulfatase proteins. *Molec. Genet. Metab.* 91, 251-258, 2007).

Therefore, the administration of the HIR Ab-IDS fusion protein, at a dose of 1 mg/kg, and a body weight of 50 kg, is expected to produce a 20% replacement of the normal brain IDS enzyme activity. Therapeutic effects in lysosomal storage disorders are achieved with the replacement of <5% of normal tissue enzyme activity [Muenzer and Fisher, Advances in the treatment of mucopolysaccharidosis type I. N Engl J Med 350 (2004) 1932-1934]. Higher degrees of replacement of IDS enzyme activity in the human brain would be possible by increasing the dosage of the HIR Ab-IDS fusion protein.

What is claimed:

1. A method for increasing iduronate-2-sulfatase (IDS) activity in a central nervous system of a subject with Hunter's syndrome, comprising systemically administering to the subject with Hunter's syndrome a therapeutically effective dose of a fusion antibody comprising:
   (a) an immunoglobulin that crosses a blood brain barrier (BBB), wherein the immunoglobulin comprises an immunoglobulin heavy chain; and
   (b) an iduronate-2-sulfatase, wherein the amino acid sequence of the iduronate-2-sulfatase is covalently linked to the amino terminus of the amino acid sequence of the immunoglobulin heavy chain, thereby forming a fusion protein;
   wherein the fusion antibody crosses the blood brain barrier (BBB) and catalyzes hydrolysis of 2-sulfate groups of the L-iduronate 2-sulfate units of dermatan sulfate, heparan sulfate or heparin, wherein the iduronate-2-sulfatase retains at least 20% of its activity compared to its activity as a separate entity after crossing a BBB of the subject with Hunter's syndrome and entering a lysosomal compartment of a cell in a central nervous system of the subject with Hunter's syndrome, and wherein the iduronate-2-sulfatase specific activity of the fusion antibody is at least 10,000 units/mg.

2. The method of claim 1, wherein the fusion antibody further comprises an immunoglobulin light chain.

3. The method of claim 1, wherein the fusion antibody is post-translationally modified by a sulfatase modifying factor type 1 (SUMF1).

4. The method of claim 1, wherein the fusion antibody reduces glycosoaminoglycan (GAG) accumulation in Hunter fibroblasts when administered to a medium comprising said Hunter fibroblasts.

5. The method of claim 1, wherein the immunoglobulin retains at least 20% of its activity compared to its activity as a separate entity.

6. The method of claim 1, wherein the immunoglobulin heavy chain is an immunoglobulin heavy chain of IgG.

7. The method of claim 2, wherein the immunoglobulin light chain is an immunoglobulin light chain of lambda class.

8. The method of claim 2, wherein the immunoglobulin light chain is an immunoglobulin light chain of kappa class.

9. The method of claim 1, wherein the fusion antibody crosses the BBB by binding to an endogenous BBB receptor-mediated transport system.

10. The method of claim 1, wherein the fusion antibody crosses the BBB via an endogenous BBB receptor selected from the group consisting of an insulin receptor, a transferrin receptor, a leptin receptor, a lipoprotein receptor, and an IGF receptor.

11. The method of claim 1, wherein the fusion antibody crosses the BBB by binding an insulin receptor.

12. The method of claim 1, wherein the iduronate-2-sulfatase is at least 90% identical to SEQ ID NO:9.

13. The method of claim 1, wherein the fusion antibody comprises a formylglycine.

14. The method of claim 1, wherein the fusion protein further comprises a linker between the amino acid sequence of the iduronate-2-sulfatase and the amino terminus of the amino acid sequence of the immunoglobulin heavy chain.

\* \* \* \* \*